US010959986B2

(12) United States Patent
Balog et al.

(10) Patent No.: US 10,959,986 B2
(45) Date of Patent: Mar. 30, 2021

(54) INHIBITORS OF INDOLEAMINE 2,3-DIOXYGENASE AND METHODS OF THEIR USE

(71) Applicant: BRISTOL-MYERS SQUIBB COMPANY, Princeton, NJ (US)

(72) Inventors: James Aaron Balog, Lambertville, NJ (US); Steven P. Seitz, Swarthmore, PA (US); Susheel Jethanand Nara, Mumbai (IN); Saumya Roy, Bangalore (IN); Srinivasan Thangathirupathy, Hosur (IN); Soodamani Thangavel, Krishnagiri (IN); Ramesh Kumar Sistla, Bangalore (IN)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 16/555,634

(22) Filed: Aug. 29, 2019

(65) Prior Publication Data

US 2020/0069646 A1 Mar. 5, 2020

Related U.S. Application Data

(60) Provisional application No. 62/724,434, filed on Aug. 29, 2018.

(51) Int. Cl.
| | |
|---|---|
| *A61K 31/415* | (2006.01) |
| *A61K 31/5377* | (2006.01) |
| *C07D 231/12* | (2006.01) |
| *C07D 401/12* | (2006.01) |
| *C07D 403/12* | (2006.01) |
| *C07D 261/08* | (2006.01) |
| *C07D 277/22* | (2006.01) |
| *C07D 285/08* | (2006.01) |
| *C07D 211/60* | (2006.01) |
| *C07D 317/50* | (2006.01) |
| *C07D 307/36* | (2006.01) |
| *C07D 333/54* | (2006.01) |
| *C07D 231/56* | (2006.01) |
| *C07D 221/22* | (2006.01) |
| *C07D 471/04* | (2006.01) |
| *C07D 487/04* | (2006.01) |
| *A61K 31/17* | (2006.01) |
| *A61K 31/4439* | (2006.01) |
| *A61K 31/506* | (2006.01) |
| *A61K 31/42* | (2006.01) |
| *A61K 31/426* | (2006.01) |
| *A61K 31/433* | (2006.01) |
| *A61K 31/357* | (2006.01) |
| *A61K 31/341* | (2006.01) |
| *A61K 31/381* | (2006.01) |
| *C07C 275/42* | (2006.01) |

(52) U.S. Cl.
CPC ............ *A61K 31/415* (2013.01); *A61K 31/17* (2013.01); *A61K 31/341* (2013.01); *A61K 31/357* (2013.01); *A61K 31/381* (2013.01); *A61K 31/42* (2013.01); *A61K 31/426* (2013.01); *A61K 31/433* (2013.01); *A61K 31/4439* (2013.01); *A61K 31/506* (2013.01); *A61K 31/5377* (2013.01); *C07C 275/42* (2013.01); *C07D 211/60* (2013.01); *C07D 221/22* (2013.01); *C07D 231/12* (2013.01); *C07D 231/56* (2013.01); *C07D 261/08* (2013.01); *C07D 277/22* (2013.01); *C07D 285/08* (2013.01); *C07D 307/36* (2013.01); *C07D 317/50* (2013.01); *C07D 333/54* (2013.01); *C07D 401/12* (2013.01); *C07D 403/12* (2013.01); *C07D 471/04* (2013.01); *C07D 487/04* (2013.01)

(58) Field of Classification Search
CPC .. C07D 231/12; C07D 277/28; C07D 401/12; C07D 285/08; C07D 403/12; C07D 211/26; C07D 261/08; C07D 307/52; C07D 333/58; C07D 311/58; C07D 239/26; C07D 405/12; C07D 413/12; C07D 417/12; C07D 487/04; C07D 471/04
See application file for complete search history.

(56) References Cited

U.S. PATENT DOCUMENTS

| | | | |
|---|---|---|---|
| 9,598,422 B2 | 3/2017 | Beck et al. | |
| 2007/0167426 A1 | 7/2007 | Siddiqui et al. | |
| 2009/0155311 A1 | 6/2009 | Chen et al. | |

FOREIGN PATENT DOCUMENTS

| | | |
|---|---|---|
| WO | 2004/094409 A1 | 11/2004 |
| WO | 2006/029879 | 3/2006 |
| WO | 2006/105021 A2 | 10/2006 |
| WO | 2006/122150 A1 | 11/2006 |
| WO | 2007/005874 A2 | 1/2007 |
| WO | 2007/075598 A2 | 7/2007 |

(Continued)

OTHER PUBLICATIONS

Vacchelli. OncoImmunology, 2014, 3:10, e957994-1 to e957994-10 (Year: 2014).*

(Continued)

*Primary Examiner* — Noble E Jarrell
(74) *Attorney, Agent, or Firm* — BakerHostetler

(57) ABSTRACT

There are disclosed compounds that modulate or inhibit the enzymatic activity of indoleamine 2,3-dioxygenase (IDO), pharmaceutical compositions containing said compounds and methods of treating proliferative disorders, such as cancer, viral infections and/or inflammatory disorders utilizing the compounds of the disclosure.

42 Claims, No Drawings

(56) References Cited

FOREIGN PATENT DOCUMENTS

| | | | |
|---|---|---|---|
| WO | 2008/036642 A2 | 3/2008 | |
| WO | 2008/036653 A2 | 3/2008 | |
| WO | 2009/009116 | 1/2009 | |
| WO | 2009/044273 | 4/2009 | |
| WO | 2009/073620 A2 | 6/2009 | |
| WO | 2010/019570 | 2/2010 | |
| WO | 2010/077634 A1 | 7/2010 | |
| WO | 2011/028683 | 3/2011 | |
| WO | 2011/056652 | 5/2011 | |
| WO | 2011/070024 | 6/2011 | |
| WO | 2011/107553 A1 | 9/2011 | |
| WO | 2011/131407 A1 | 10/2011 | |
| WO | 2011/140249 A2 | 11/2011 | |
| WO | 2012/032433 | 3/2012 | |
| WO | 2012/142237 A1 | 10/2012 | |
| WO | 2012/145493 A1 | 10/2012 | |
| WO | 2013/079174 | 6/2013 | |
| WO | 2013/087699 | 6/2013 | |
| WO | 2013/119716 A1 | 8/2013 | |
| WO | 2013/132044 A1 | 9/2013 | |
| WO | 2013/169264 A1 | 11/2013 | |
| WO | 2014/008218 | 1/2014 | |
| WO | 2014/036357 A1 | 3/2014 | |
| WO | 2016/073738 A2 | 5/2016 | |
| WO | 2016/073770 A1 | 5/2016 | |
| WO | 2016/073774 A2 | 5/2016 | |

OTHER PUBLICATIONS

Gaspari et al. "Structure-Activity Study of Brassinin Derivatives as Indoleamlne 2,3-Dioxygenase Inhibitors", J Med Chem. 2006. vol. 49(2), pp. 684-692.

Ball et al, Characterization of an indoleamine 2, 3-dioxygenase-like protein found in humans and mice, Gene, Jul. 1, 2007;396(1):203-213.

Brandacher et al, Prognostic value of indoleamine 2, 3-dioxygenase expression in colorectal cancer: effect on tumor-infiltrating T cells, Clinical cancer research, Feb. 15, 2006;12(4):1144-1151.

Bundgaard H. (C) Means to enhance penetration:(1) Prodrugs as a means to improve the delivery of peptide drugs, Advanced Drug Delivery Reviews, Jan. 1, 1992;8(1):1-38.

Bundgaard, H., Chapter 5: "Design and Application of Prodrugs", A Textbook of Drug Design and Development, pp. 113-191, Krogsgaard-Larsen, P., et al., eds., Harwood Academic Publishers, 1991.

Evans et al., Asymmetric alkylation reactions of chiral imide enolates. A practical approach to the enantioselective synthesis of. alpha.-substituted carboxylic acid derivatives, Journal of the American Chemical Society, Mar. 1982;104(6):1737-1739.

Goldstein et al., Biological efficacy of a chimeric antibody to the epidermal growth factor receptor in a human tumor xenograft model. Clinical Cancer Research, Nov. 1, 1995;1(11):1311-1318.

Ishiyama et al., Palladium (0)-catalyzed cross-coupling reaction of alkoxydiboron with haloarenes: a direct procedure for arylboronic esters, The Journal of Organic Chemistry, Nov. 1995;60(23):7508-7510.

Kakeya et al., Studies on Prodrugs of Cephalosporins. I. Synthesis and Biological Properties of Glycyloxybenzoyloxymethyl and Glycylaminobenzoyloxymethyl Esters of 7ß[2-(2-Aminothiazol-4-yl)-(Z)-2-methoxyiminoacetamido]-3-methyl-3-cephem-4-carboxylic Acid, Chemical and pharmaceutical bulletin, Feb. 25, 1984;32(2):692-698.

Kohl et al., Inhibition of farnesyltransferase induces regression of mammary and salivary carcinomas in ras transgenic mice, Nature medicine. Aug. 1995;1(8):792-797.

Littlejohn et al., Expression and purification of recombinant human indoleamine 2, 3-dioxygenase, Protein expression and purification, Jun. 1, 2000;19(1):22-29.

Nielsen et al., Glycolamide esters as biolabile prodrugs of carboxylic acid agents: synthesis, stability, bioconversion, and physicochemical properties, Journal of Pharmaceutical Sciences, Apr. 1988;77(4):285-298.

Pubchem, Substance Record for SID 111585117. Create Date: Mar. 7, 2011. Retrieved on Jun. 22, 2017. Retrieved from the Internet: https://pubchem.ncbi.nlm.nih.gov/substance/111585117, entire document.

Pubchem, Substance Record for SID 121181436. Create Date: May 5, 2011. Retrieved on Jun. 22, 2017. Retrieved from the Internet: https://pubchem.ncbi.nlm.nih.gov/substance/121181436. entire document.

Sarkar et al., Induction of indoleamine 2, 3-dioxygenase by interferon-? in human islets, Diabetes, Jan. 1, 2007;56(1):72-79.

Sausville et al., Cyclin-dependent kinase modulators studied at the NCI: pre-clinical and clinical studies, Current Medicinal Chemistry-Anti-Cancer Agents, Jan. 1, 2003;3(1):47-56.

Scheller et al., Paclitaxel balloon coating, a novel method for prevention and therapy of restenosis, Circulation, Aug. 17, 2004;110(7):810-814.

Sekulic et al., A direct linkage between the phosphoinositide 3-kinase-AKT signaling pathway and the mammalian target of rapamycin in mitogen-stimulated and transformed cells, Cancer research, Jul. 1, 2000;60(13):3504-3513.

Serafini et al., Myeloid suppressor cells in cancer: recruitment, phenotype, properties, and mechanisms of immune suppression, in Seminars in cancer biology Feb. 1, 2006 (vol. 16, No. 1, pp. 53-65). Academic Press.

Surry et al., "Dialkylbiaryl Phosphines in PD-Catalyzed Amination: A User's Guide", Chem. Sci., 2011, 2, 27-50.

Vlahos et al., A specific inhibitor of phosphatidylinositol 3-kinase, 2-(4-morpholinyl)-8-phenyl-4H-1-benzopyran-4-one (LY294002), Journal of Biological Chemistry, J. Biol. Chem, 1994, 269, 5241-5248.

Widder, K., et al., eds., Methods of Enzymology, Academic Press, 1985, 112, 309-396.

Zou et al., "Fleck-type coupling vs. conjugate addition in phosphine—rhodium catalyzed reactions of aryl boronic acids with a,ß-unsaturated carbonyl compounds: a systematic investigation", Dalton Trans., 2007, 28, 3055-3064.

\* cited by examiner

INHIBITORS OF INDOLEAMINE 2,3-DIOXYGENASE AND METHODS OF THEIR USE

CROSS-REFERENCE TO RELATED APPLICATION

This application claims the benefit of priority to U.S. provisional patent application No. 62/724,434, filed on Aug. 29, 2018, the entirety of which is incorporated by reference herein.

FIELD OF THE DISCLOSURE

The disclosure relates generally to compounds that modulate or inhibit the enzymatic activity of indoleamine 2,3-dioxygenase (IDO), pharmaceutical compositions containing said compounds and methods of treating proliferative disorders, such as cancer, viral infections and/or autoimmune diseases utilizing the compounds of the disclosure.

BACKGROUND OF THE DISCLOSURE

Indoleamine 2,3-dioxygenase (IDO; also known as IDO1) is an IFN-γ target gene that plays a role in immunomodulation. IDO is an oxidoreductase and one of two enzymes that catalyze the first and rate-limiting step in the conversion of tryptophan to N-formylkynurenine. It exists as a 41 kD monomer that is found in several cell populations, including immune cells, endothelial cells, and fibroblasts. IDO is relatively well-conserved between species, with mouse and human sharing 63% sequence identity at the amino acid level. Data derived from its crystal structure and site-directed mutagenesis show that both substrate binding and the relationship between the substrate and iron-bound dioxygenase are necessary for activity. A homolog to IDO (IDO2) has been identified that shares 44% amino acid sequence homology with IDO, but its function is largely distinct from that of IDO. (See, e.g., Serafini, P. et al., *Semin. Cancer Biol.*, 16(1):53-65 (February 2006) and Ball, H. J. et al., *Gene*, 396(1):203-213 (Jul. 1, 2007)).

IDO plays a major role in immune regulation, and its immunosuppressive function manifests in several manners. Importantly, IDO regulates immunity at the T cell level, and a nexus exists between IDO and cytokine production. In addition, tumors frequently manipulate immune function by upregulation of IDO. Thus, modulation of IDO can have a therapeutic impact on a number of diseases, disorders and conditions.

A pathophysiological link exists between IDO and cancer. Disruption of immune homeostasis is intimately involved with tumor growth and progression, and the production of IDO in the tumor microenvironment appears to aid in tumor growth and metastasis. Moreover, increased levels of IDO activity are associated with a variety of different tumors (Brandacher, G. et al., *Clin. Cancer Res.*, 12(4):1144-1151 (Feb. 15, 2006)).

Treatment of cancer commonly entails surgical resection followed by chemotherapy and radiotherapy. The standard treatment regimens show highly variable degrees of long-term success because of the ability of tumor cells to essentially escape by regenerating primary tumor growth and, often more importantly, seeding distant metastasis. Recent advances in the treatment of cancer and cancer-related diseases, disorders and conditions comprise the use of combination therapy incorporating immunotherapy with more traditional chemotherapy and radiotherapy. Under most scenarios, immunotherapy is associated with less toxicity than traditional chemotherapy because it utilizes the patient's own immune system to identify and eliminate tumor cells.

In addition to cancer, IDO has been implicated in, among other conditions, immunosuppression, chronic infections, and autoimmune diseases or disorders (e.g., rheumatoid arthritis). Thus, suppression of tryptophan degradation by inhibition of IDO activity has tremendous therapeutic value. Moreover, inhibitors of IDO can be used to enhance T cell activation when the T cells are suppressed by pregnancy, malignancy, or a virus (e.g., HIV). Although their roles are not as well defined, IDO inhibitors may also find use in the treatment of patients with neurological or neuropsychiatric diseases or disorders (e.g., depression).

Small molecule inhibitors of IDO have been developed to treat or prevent IDO-related diseases. For example, the IDO inhibitors 1-methyl-DL-tryptophan; p-(3-benzofuranyl)-DL-alanine; p-[3-benzo(b)thienyl]-DL-alanine; and 6-nitro-L-tryptophan have been used to modulate T cell-mediated immunity by altering local extracellular concentrations of tryptophan and tryptophan metabolites (WO 99/29310). Compounds having IDO inhibitory activity are further reported in PCT Publication No. WO 2004/094409.

In view of the role played by indoleamine 2,3-dioxygenase in a diverse array of diseases, disorders and conditions, and the limitations (e.g., efficacy) of current IDO inhibitors, new IDO modulators, and compositions and methods associated therewith, are needed.

SUMMARY OF THE DISCLOSURE

The disclosure is directed to compounds of formula I or II

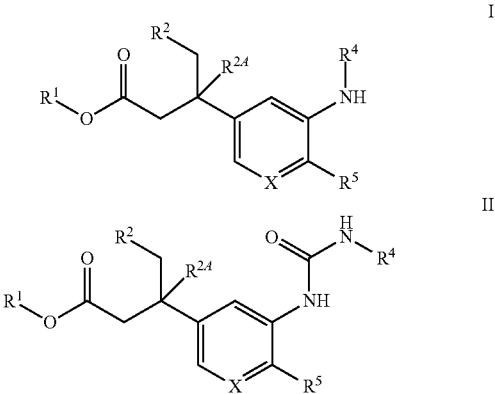

wherein
X is CH or N;
$R^1$ is H or $C_{1-6}$alkyl;
$R^2$ is H, $C_{1-6}$alkyl, or $C_{0-6}$alk-O$C_{1-6}$alkyl;
$R^{2A}$ is H or $C_{1-6}$alkyl;
$R^5$ is
  phenyl optionally substituted with one, two or three substituents independently selected from halogen, $C_{0-6}$alk-O—$C_{1-6}$alkyl, or —CN;
  heteroaryl optionally substituted with one, two or three substituents independently selected from halogen, optionally substituted phenyl, optionally substituted benzyl, optionally substituted $C_{1-6}$alkyl, $C_{1-6}$haloalkyl, $C_{0-6}$alk-O—$C_{1-6}$alkyl, heterocyclyl, or —CN;

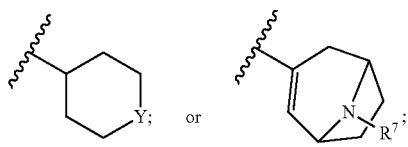

Y is O, CHR$^6$, or NR$^7$;

R$^6$ is H or phenyl;

R$^7$ is H, pyridyl, pyrazinyl, pyridazinyl, pyrimidyl, —COOH, —COOC$_{1-6}$alkyl, or COR$^{7A}$
  wherein R$^{7A}$ is H, C$_{1-6}$alkyl, pyridyl optionally substituted with OC$_{1-6}$alkyl, pyrazinyl optionally substituted with OC$_{1-6}$alkyl, pyridazinyl optionally substituted with OC$_{1-6}$alkyl, or pyrimidyl optionally substituted with OC$_{1-6}$alkyl; and R$^4$ is phenyl, pyridyl, pyrazinyl, pyridazinyl, pyrimidyl, or benzothiazolyl, optionally substituted with one, two or three substituents independently selected from halogen, C$_{1-6}$alkyl, C$_{1-6}$haloalkyl, OC$_{1-6}$haloalkyl, C$_{0-6}$alk-O—C$_{1-6}$alkyl, —CN, —COOH, and —COOC$_{1-6}$alkyl, or a pharmaceutically acceptable salt thereof or solvate thereof. Compositions comprising these compounds, as well as methods of using these compounds, are also described.

DETAILED DESCRIPTION

Compounds of the Disclosure

The disclosure is directed to compounds of formula I and formula II:

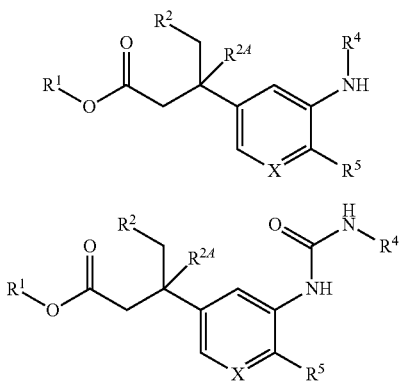

Some embodiments of the disclosure are directed to compounds of formula I. Other embodiments of the disclosure are directed to compounds of formula II.

According to the disclosure, X is CH or N. In some embodiments, X is CH. In other embodiments, X is N.

According to the disclosure, R$^1$ is H or C$_{1-6}$alkyl. In some aspects, R$^1$ is H. In other aspects, R$^1$ is C$_{1-6}$alkyl, for example, C$_6$alkyl (e.g., hexyl, methylpentanyl), C$_5$alkyl (e.g., pentyl, isopentyl), C$_4$alkyl (e.g., butyl, t-butyl), C$_3$alkyl (e.g., propyl, isopropyl), ethyl (C$_2$alkyl), or methyl (C$_1$alkyl). In preferred embodiments, R$^1$ is H.

According to the disclosure, R$^2$ is H, C$_{1-6}$alkyl, or C$_{0-6}$alk-OC$_{1-6}$alkyl. In some aspects, R$^2$ is H. In other aspects, R$^2$ is C$_{1-6}$alkyl, for example, C$_6$alkyl (e.g., hexyl, methylpentanyl), C$_5$alkyl (e.g., pentyl, isopentyl), C$_4$alkyl (e.g., butyl, t-butyl), C$_3$alkyl (e.g., propyl, isopropyl), ethyl (C$_2$alkyl), or methyl (C$_1$alkyl). In some aspects, R$^2$ is C$_{0-6}$alk-OC$_{1-6}$alkyl, for example, C$_{1-6}$alk-OC$_{1-6}$alkyl, C$_{0-5}$alk-OC$_{1-6}$alkyl, C$_{0-4}$alk-OC$_{1-6}$alkyl, C$_{0-3}$alk-OC$_{1-6}$alkyl, C$_{0-2}$alk-OC$_{1-6}$alkyl, C$_2$alk-OC$_{1-6}$alkyl, C$_1$alk-OC$_{1-6}$alkyl, C$_0$alk-OC$_{1-6}$alkyl, C$_{0-6}$alk-OC$_{1-5}$alkyl, C$_{1-6}$alk-OC$_{1-5}$alkyl, C$_{0-6}$alk-OC$_{1-4}$alkyl, C$_{0-6}$alk-OC$_{1-3}$alkyl, C$_{0-6}$alk-OC$_{1-2}$alkyl, and C$_{0-6}$alk-OC$_1$alkyl.

According to the disclosure, R$^{2A}$ is H or C$_{1-6}$alkyl. In some aspects, R$^{2A}$ is H. Preferably, R$^{2A}$ is H when R$^2$ is C$_{1-6}$alkyl or C$_{0-6}$alk-OC$_{1-6}$alkyl. In other aspects, R$^{2A}$ is C$_1$-6alkyl, for example, C$_6$alkyl (e.g., hexyl, methylpentanyl), C$_5$alkyl (e.g., pentyl, isopentyl), C$_4$alkyl (e.g., butyl, t-butyl), C$_3$alkyl (e.g., propyl, isopropyl), ethyl (C$_2$alkyl), or methyl (C$_1$alkyl).

According to the disclosure, R$^5$ is phenyl optionally substituted with one, two or three substituents independently selected from halogen, C$_{0-6}$alk-O—C$_{1-6}$alkyl, or —CN; heteroaryl optionally substituted with one, two or three substituents independently selected from halogen, optionally substituted phenyl, optionally substituted benzyl, optionally substituted C$_{1-6}$alkyl, C$_{1-6}$haloalkyl, C$_{0-6}$alk-O—C$_{1-6}$alkyl, heterocyclyl, or —CN;

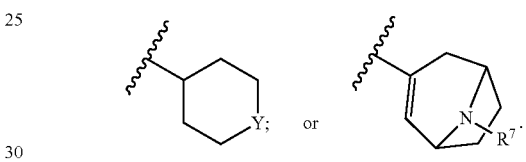

In some aspects, R$^5$ is optionally substituted phenyl. In some embodiments, R$^5$ is phenyl. In other embodiments, R$^5$ is phenyl substituted with one, two or three substituents independently selected from halogen, C$_{0-6}$alk-O—C$_{1-6}$alkyl, or —CN. In those embodiments wherein the phenyl is substituted with one or more halogen, the halogen may be independently selected from F, Cl, Br, or I, preferably F, Cl, or Br. In some embodiments, the phenyl is 4-chlorophenyl, 4-chloro-2-fluorophenyl, or 4-chloro-3-fluorophenyl. In those embodiments where the phenyl is substituted with one or more C$_{0-6}$alk-O—C$_{1-6}$alkyl, the C$_{0-6}$alk-O—C$_{1-6}$alkyl, is independently selected from, e.g., C$_{1-6}$alk-OC$_{1-6}$alkyl, C$_{1-5}$alk-OC$_{1-6}$alkyl, C$_{1-4}$alk-OC$_{1-6}$alkyl, C$_{1-3}$alk-OC$_{1-6}$alkyl, C$_{1-2}$alk-OC$_{1-6}$alkyl, C$_2$alk-OC$_{1-6}$alkyl, C$_1$alk-OC$_{1-6}$alkyl, C$_0$alk-OC$_{1-6}$alkyl, C$_{0-6}$alk-OC$_{1-5}$alkyl, C$_{0-6}$alk-OC$_{1-5}$alkyl, C$_{0-6}$alk-OC$_{1-4}$alkyl, C$_{0-6}$alk-OC$_{1-3}$alkyl, C$_{0-6}$alk-OC$_{1-2}$alkyl, or C$_{0-6}$alk-OC$_1$alkyl. In some embodiments, the phenyl is 3-fluoro-4-methoxyphenyl or 2-fluoro-4-methoxyphenyl. In some embodiments, the phenyl is substituted with one or more CN. In some embodiments, the phenyl is 4-cyano-3-methoxyphenyl.

In some aspects, R$^5$ is optionally substituted heteroaryl, wherein the heteroaryl is attached through any available carbon atom. In some embodiments, the heteroaryl is pyrazolyl, pyrazinyl, isoxazolyl, thiazolyl, benzodioxazolyl, furanyl, dihydrobenzofuranyl, benzofuranyl, benzothiophenyl, pyrimidinyl, indazolyl, pyridinyl, benzothiazolyl, imidazo[1,2-a]pyridinyl, imidazo[1,5-a]pyridinyl, benzo[c][1,2,5]oxadiazolyl, or pyrazolo[1,5-a]pyrimidinyl, wherein the heteroaryl is optionally substituted with one, two or three substituents independently selected from halogen, optionally substituted phenyl, optionally substituted benzyl, optionally substituted C$_{1-6}$alkyl, C$_{1-6}$haloalkyl, C$_{0-6}$alk-O—C$_{1-6}$alkyl, heterocyclyl, and —CN. In some aspects, the heteroaryl is substituted with one substituent that is halogen, optionally substituted phenyl, optionally substituted benzyl, optionally substituted $C_{1-6}$alkyl, $C_{1-6}$haloalkyl, $C_{0-6}$alk-O—$C_{1-6}$alkyl, heterocyclyl, or —CN. In some aspects, the heteroaryl is substituted with two substituents independently selected from halogen, optionally substituted phenyl, optionally substituted benzyl, optionally substituted $C_{1-6}$alkyl, $C_{1-6}$haloalkyl, $C_{0-6}$alk-O—$C_{1-6}$alkyl, heterocyclyl, and —CN. In other aspects, the heteroaryl is substituted with three substituents independently selected from halogen, optionally substituted phenyl, optionally substituted benzyl, optionally substituted $C_{1-6}$alkyl, $C_{1-6}$haloalkyl, $C_{0-6}$alk-O—$C_{1-6}$alkyl, heterocyclyl, and —CN.

In some aspects, the heteroaryl is unsubstituted. In some embodiments, the heteroaryl is 1H-pyrazol-4-yl, thiazol-2-yl, furan-3-yl, benzo[d][1,3]dioxol-5-yl, 2,3-dihydrobenzofuran-5-yl, benzofuran-5-yl, benzo[b]thiophen-5-yl, pyrimidin-5-yl, 1H-indazol-4-yl, 1H-pyrrolo[2,3-c]pyridin-3-yl, benzo[d]thiazol-2-yl, imidazo[1,2-a]pyridin-2-yl, benzo[c][1,2,5]oxadiazol-5-yl, pyrazolo[1,5-a]pyrimidin-5-yl, imidazo[1,5-a]pyridin-6-yl, or imidazo[1,2-a]pyridin-7-yl.

In those embodiments wherein the heteroaryl is substituted with one or more halogen, the halogen may be independently selected from F, Cl, Br, or I, preferably F, Cl, or Br. In some embodiments, the heteroaryl is 3-fluoropyridin-4-yl, 5-fluoropyrimidin-2-yl, or 2,2-difluorobenzo[d][1,3]dioxol-5-yl.

In some embodiments the heteroaryl is substituted with one or more phenyl groups wherein the phenyl groups are optionally substituted with one or more halogens (i.e., F, C1, Br, or I). In some embodiments, the heteroaryl is 4-phenylthiazol-2-yl, 1-(4-fluorophenyl)-1H-pyrazol-4-yl, 2-phenylthiazol-4-yl, or 4-phenylthiazol-2-yl.

In some embodiments, the heteroaryl is substituted with a benzyl group, wherein the benzyl group is optionally substituted with a $C_{0-6}$alk-O—$C_{1-6}$alkyl group. In some embodiments, the heteroaryl is 1-benzyl-1H-pyrazol-4-yl or 1-(4-methoxybenzyl)-1H-pyrazol-4-yl.

In those embodiments where the heteroaryl is substituted with one or more $C_{1-6}$alkyl, the $C_{1-6}$alkyl is independently selected from $C_6$alkyl, $C_5$alkyl, $C_4$alkyl, $C_3$alkyl, ethyl ($C_2$alkyl), or methyl ($C_1$alkyl). In some embodiments, the $C_{1-6}$alkyl is optionally substituted with a heterocyclyl group such as, e.g., morpholino. In some embodiments, the heteroaryl is 1-methyl-1H-pyrazol-4-yl, 3,5-dimethylisoxazol-4-yl, 4-methylthiazol-2-yl, 5-methyl-1,3,4-thiadiazol-2-yl, 1-isopropyl-1H-pyrazol-4-yl, 1-methyl-1H-indazol-5-yl, 3,5-dimethylisoxazol-4-yl, 2,4-dimethylthiazol-5-yl, 2-methylbenzo[d]oxazol-6-yl, 2-methylbenzo[d]thiazol-6-yl, 5-methylpyrimidin-2-yl, 3,5-dimethyl-1H-pyrazol-4-yl, 1,3,5-trimethyl-1H-pyrazol-4-yl, 4-methylthiazol-2-yl, 5-methyl-1,3,4-thiadiazol-2-yl, or 1-(2-morpholinoethyl)-1H-pyrazol-4-yl.

In those embodiments wherein the heteroaryl is substituted with one or more $C_{1-6}$haloalkyl, the $C_{1-6}$haloalkyl is independently selected from, e.g., $CF_3$ or $CHF_2$, preferably $CF_3$. In some embodiments, the heteroaryl is 6-(difluoromethyl)pyridin-2-yl.

In those embodiments where the heteroaryl is substituted with one or more $C_{0-6}$alk-O—$C_{1-6}$alkyl, the $C_{0-6}$alk-O—$C_{1-6}$alkyl, is independently selected from, e.g., $C_{1-6}$alk-OC_{1-6}$alkyl, $C_{1-5}$alk-OC_{1-6}$alkyl, $C_{1-4}$alk-OC_{1-6}$alkyl, $C_{1-3}$alk-OC_{1-6}$alkyl, $C_{1-2}$alk-OC_{1-6}$alkyl, $C_2$alk-OC_{1-6}$alkyl, $C_1$alk-OC_{1-6}$alkyl, $C_0$alk-OC_{1-6}$alkyl, $C_{0-6}$alk-OC_{1-5}$alkyl, $C_{0-6}$alk-OC_{1-5}$alkyl, $C_{0-6}$alk-OC_{1-4}$alkyl, $C_{0-6}$alk-OC_{1-3}$alkyl, $C_{0-6}$alk-OC_{1-2}$alkyl, or $C_{0-6}$alk-OC_1$alkyl. In some embodiments, the heteroaryl is 2-ethoxypyrimidin-5-yl or 5-ethoxypyrazin-2-yl.

In some embodiments, the heteroaryl is substituted with a heterocyclyl group such as, e.g., a morpholino group. In some embodiments, the heteroaryl is 2-morpholinopyrimidin-4-yl.

In some embodiments, the heteroaryl is substituted with one or more CN. In some embodiments, the heteroaryl is 5-cyanopyridin-2-yl.

In some aspects, $R^5$ is

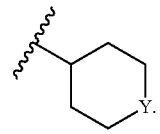

According to the disclosure, Y is O; $CHR^6$, or $NR^7$. In some embodiments, Y is O. In other embodiments, Y is $CHR^6$. In yet other embodiments, Y is $NR^7$.

According to the disclosure, $R^6$ is H or phenyl. In some embodiments, $R^6$ is H. In other embodiments, $R^6$ is phenyl. In some embodiments wherein Y is $CHR^6$, therefore, Y is —$CH_2$—. In other embodiments, Y is —CH-phenyl. Thus, in some embodiments, $R^5$ is 4-phenylcyclohexyl.

According to the disclosure, $R^7$ is H, pyridyl, pyrazinyl, pyridazinyl, pyrimidyl, —COOH, —COOC$_{1-6}$alkyl, or —COR$^{7A}$ wherein R$^{7A}$ is H, $C_{1-6}$alkyl, pyridyl optionally substituted with OC$_{1-6}$alkyl, pyrazinyl optionally substituted with OC$_{1-6}$alkyl, pyridazinyl optionally substituted with OC$_{1-6}$alkyl, or pyrimidyl optionally substituted with OC$_{1-6}$alkyl.

In some aspects, Y is $NR^7$ wherein $R^7$ is H, pyridyl, pyrazinyl, pyridazinyl, pyrimidyl, —COOH, —COOC$_{1-6}$alkyl, or —COR$^{7A}$ and wherein R$^{7A}$ is H, $C_{1-6}$alkyl, pyridyl optionally substituted with OC$_{1-6}$alkyl, pyrazinyl optionally substituted with OC$_{1-6}$alkyl, pyridazinyl optionally substituted with OC$_{1-6}$alkyl, or pyrimidyl optionally substituted with OC$_{1-6}$alkyl. In some embodiments, Y is —NH—. In other embodiments, Y is $NR^7$ wherein $R^7$ is pyridyl, pyrazinyl, pyridazinyl, pyrimidyl, —COOH, or —COOC$_{1-6}$alkyl (e.g., —COOC$_1$alkyl, —COOC$_2$alkyl, —COOC$_3$alkyl, —COOC$_4$alkyl, —COOC$_5$alkyl, or —COOC$_6$alkyl). In some embodiments, $R^7$ is pyridyl, pyrazinyl, pyridazinyl, or pyrimidyl. In still other embodiments, $R^7$ is —COOH or —COOC$_{1-6}$alkyl. In some embodiments wherein $R^7$ is —COOC$_{1-6}$alkyl, therefore, $R^5$ is 1-(tert-butoxycarbonyl)piperidin-4-yl. In other embodiments wherein $R^7$ is —COOC$_{1-6}$alkyl, $R^5$ is 1-(methoxycarbonyl)piperidin-4-yl. In other embodiments, Y is $NR^7$ wherein $R^7$ is —COR$^{7A}$ and wherein R$^{7A}$ is H, $C_{1-6}$alkyl, pyridyl optionally substituted with OC$_{1-6}$alkyl, pyrazinyl optionally substituted with OC$_{1-6}$alkyl, pyridazinyl optionally substituted with OC$_{1-6}$alkyl, or pyrimidyl optionally substituted with OC$_{1-6}$alkyl. For example, Y can be —N—CO—H, —N—CO—$C_{1-6}$alkyl, —N—CO-pyridyl, —N—CO-pyridyl wherein the pyridyl is substituted with —OC$_{1-6}$alkyl, —N—CO-pyrazinyl, —N—CO-pyrazinyl wherein the pyrazinyl is optionally substituted with —OC$_{1-6}$alkyl, —N—CO-pyridazinyl, —N—CO-pyridazinyl wherein the pyridazinyl is optionally substituted with —OC$_{1-6}$alkyl, —N—CO-pyrimidyl, or —N—CO-pyrimidyl wherein the pyrimidyl is optionally substituted with —OC$_{1-6}$alkyl.

In some aspects, $R^5$ is

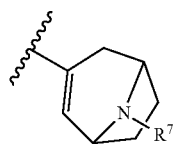

wherein $R^7$ is H, pyridyl, pyrazinyl, pyridazinyl, pyrimidyl, —COOH, —COOC$_{1-6}$alkyl, or —COR$^{7.4}$ wherein $R^{7.4}$ is H, C$_{1-6}$alkyl, pyridyl optionally substituted with OC$_{1-6}$alkyl, pyrazinyl optionally substituted with OC$_{1-6}$alkyl, pyridazinyl optionally substituted with OC$_{1-6}$alkyl, or pyrimidyl optionally substituted with OC$_{1-6}$alkyl. In some embodiments wherein $R^7$ is —COOC$_{1-6}$alkyl, $R^5$ is 8-(tert-butoxycarbonyl)-8-azabicyclo[3.2.1]oct-2-en-3-yl.

According to the disclosure, $R^4$ is phenyl, pyridyl, pyrazinyl, pyridazinyl, pyrimidyl, or benzothiazolyl, optionally substituted with one, two or three substituents independently selected from halogen, C$_{1-6}$alkyl, C$_{1-6}$haloalkyl, OC$_{1-6}$haloalkyl, C$_{0-6}$alk-O—C$_{1}$-6alkyl, —CN, —COOH, and —COOC$_{1-6}$alkyl.

In some aspects, $R^4$ is phenyl. In other aspects, $R^4$ is phenyl substituted with one, two or three substituents independently selected from halogen, C$_{1-6}$alkyl, C$_{1-6}$haloalkyl, OC$_{1-6}$haloalkyl, C$_{0-6}$alk-O—C$_{1-6}$alkyl, —CN, —COOH, and —COOC$_{1-6}$alkyl. In some aspects, the phenyl is substituted with one substituent that is halogen, C$_{1-6}$alkyl, C$_{1-6}$haloalkyl, OC$_{1-6}$haloalkyl, C$_{0-6}$alk-O—C$_{1-6}$alkyl, —CN, —COOH, and —COOC$_{1-6}$alkyl. In some aspects, the phenyl is substituted with two substituents independently selected from halogen, C$_{1-6}$alkyl, C$_{1-6}$haloalkyl, OC$_{1-6}$haloalkyl, C$_{0-6}$alk-O—C$_{1-6}$alkyl, —CN, —COOH, and —COOC$_{1-6}$alkyl. In other aspects, the phenyl is substituted with three substituents independently selected from halogen, C$_{1-6}$alkyl, C$_{1-6}$haloalkyl, OC$_{1-6}$haloalkyl, C$_{0-6}$alk-O—C$_{1-6}$alkyl, —CN, —COOH, and —COOC$_{1-6}$alkyl. In those embodiments wherein the phenyl is substituted with one or more halogen, the halogen may be independently selected from F, Cl, Br, or I, preferably F, Cl, or Br. In some embodiments, $R^4$ is 4-fluorophenyl, 4-chlorophenyl, 3-chlorophenyl, 3-fluorophenyl, 4-chloro-3-fluorophenyl, or 4-chloro-2-fluorophenyl. In those embodiments where the phenyl is substituted with one or more C$_{1-6}$alkyl, the C$_{1-6}$alkyl is independently selected from C$_6$alkyl, C$_5$alkyl, C$_4$alkyl, C$_3$alkyl, ethyl (C$_2$alkyl), or methyl (C$_1$alkyl). In some embodiments, $R^4$ is 4-methylphenyl (i.e., p-tolyl). In those embodiments wherein the phenyl is substituted with one or more C$_{1-6}$haloalkyl, the C$_{1-6}$haloalkyl is independently selected from, e.g., CF$_3$ or CHF$_2$, preferably CF$_3$. In some embodiments, $R^4$ is 4-(trifluoromethyl)phenyl. In those embodiments wherein the phenyl is substituted with one or more OC$_{1-6}$haloalkyl, the OC$_{1-6}$haloalkyl is independently selected from, e.g., OCF$_3$ or OCHF$_2$, preferably OCF$_3$. In those embodiments where the phenyl is substituted with one or more C$_{0-6}$alk-O—C$_{1-6}$alkyl, the C$_{0-6}$alk-O—C$_{1-6}$alkyl, is independently selected from, e.g., C$_{1-6}$alk-OC$_{1-6}$alkyl, C$_{1-5}$alk-OC$_{1-6}$alkyl, C$_{1-4}$alk-OC$_{1-6}$alkyl, C$_{1-3}$alk-OC$_{1-6}$alkyl, C$_{1-2}$alk-OC$_{1-6}$alkyl, C$_2$alk-OC$_{1-6}$alkyl, C$_1$alk-OC$_{1-6}$alkyl, C$_0$alk-OC$_{1-6}$alkyl, C$_{0-6}$alk-OC$_{1-5}$alkyl, C$_{0-6}$alk-OC$_{1-5}$alkyl, C$_{0-6}$alk-OC$_{1-4}$alkyl, C$_{0-6}$alk-OC$_{1-3}$alkyl, C$_{0-6}$alk-OC$_{1-2}$alkyl, or C$_{0-6}$alk-OC$_1$alkyl. In some embodiments, the phenyl is substituted with one or more CN. In some embodiments, $R^4$ is 4-cyanophenyl. In other embodiments, the phenyl is substituted with one or more COOH. In those embodiments wherein the phenyl is substituted with one or more —COOC$_{1-6}$alkyl, the —COOC$_{1-6}$alkyl is independently selected from —COOC$_6$alkyl, —COOC$_5$alkyl, —COOC$_4$alkyl, —COOC$_3$alkyl, —COOC$_2$alkyl, and —COOC$_1$alkyl.

In some aspects, $R^4$ is pyridyl. In some embodiments, $R^4$ is pyridin-3-yl or pyridin-2-yl. In other aspects, $R^4$ is pyridyl substituted with one, two or three substituents independently selected from halogen, C$_{1-6}$alkyl, C$_{1-6}$haloalkyl, OC$_{1-6}$haloalkyl, C$_{0-6}$alk-O—C$_{1-6}$alkyl, —CN, —COOH, and —COOC$_{1-6}$alkyl. In some aspects, the pyridyl is substituted with one substituent that is halogen, C$_{1-6}$alkyl, C$_{1-6}$haloalkyl, OC$_{1-6}$haloalkyl, C$_{0-6}$alk-O—C$_{1-6}$alkyl, —CN, —COOH, and —COOC$_{1-6}$alkyl. In some aspects, the pyridyl is substituted with two substituents independently selected from halogen, C$_{1-6}$alkyl, C$_{1-6}$haloalkyl, OC$_{1-6}$haloalkyl, C$_{0-6}$alk-O—C$_{1-6}$alkyl, —CN, —COOH, and —COOC$_{1-6}$alkyl. In other aspects, the pyridyl is substituted with three substituents independently selected from halogen, C$_{1-6}$alkyl, C$_{1-6}$haloalkyl, OC$_{1-6}$haloalkyl, C$_{0-6}$alk-O—C$_{1-6}$alkyl, —CN, —COOH, and —COOC$_{1-6}$alkyl. In those embodiments wherein the pyridyl is substituted with one or more halogen, the halogen may be independently selected from F, Cl, Br, or I, preferably F, Cl, or Br. In some embodiments, $R^4$ is 5-chloropyridin-2-yl. In those embodiments where the pyridyl is substituted with one or more C$_{1-6}$alkyl, the C$_{1-6}$alkyl is independently selected from C$_6$alkyl, C$_5$alkyl, C$_4$alkyl, C$_3$alkyl, ethyl (C$_2$alkyl), or methyl (C$_1$alkyl). In those embodiments wherein the pyridyl is substituted with one or more C$_{1-6}$haloalkyl, the C$_{1-6}$haloalkyl is independently selected from, e.g., CF$_3$ or CHF$_2$, preferably CF$_3$. In those embodiments wherein the pyridyl is substituted with one or more OC$_{1-6}$haloalkyl, the OC$_{1-6}$haloalkyl is independently selected from, e.g., OCF$_3$ or OCHF$_2$, preferably OCF$_3$. In those embodiments where the pyridyl is substituted with one or more C$_{0-6}$alk-O—C$_{1-6}$alkyl, the C$_{0-6}$alk-O—C$_{1-6}$alkyl, is independently selected from, e.g., C$_{1-6}$alk-OC$_{1-6}$alkyl, C$_{1-5}$alk-OC$_{1-6}$alkyl, C$_{1-4}$alk-OC$_{1-6}$alkyl, C$_{1-3}$alk-OC$_{1-6}$alkyl, C$_{1-2}$alk-OC$_{1-6}$alkyl, C$_2$alk-OC$_{1-6}$alkyl, C$_1$alk-OC$_{1-6}$alkyl, C$_0$alk-OC$_{1-6}$alkyl, C$_{0-6}$alk-OC$_{1-5}$alkyl, C$_{0-6}$alk-OC$_{1-5}$alkyl, C$_{0-6}$alk-OC$_{1-4}$alkyl, C$_{0-6}$alk-OC$_{1-3}$alkyl, C$_{0-6}$alk-OC$_{1-2}$alkyl, or C$_{0-6}$alk-OC$_1$alkyl. In some embodiments, the pyridyl is substituted with one or more CN. In some embodiments, $R^4$ is 5-cyanopyridin-2-yl. In other embodiments, the pyridyl is substituted with one or more COOH. In those embodiments wherein the pyridyl is substituted with one or more —COOC$_{1-6}$alkyl, the —COOC$_{1-6}$alkyl is independently selected from —COOC$_6$alkyl, —COOC$_5$alkyl, —COOC$_4$alkyl, —COOC$_3$alkyl, —COOC$_2$alkyl, and —COOC$_1$alkyl.

In some aspects, $R^4$ is pyrazinyl. In other aspects, $R^4$ is pyrazinyl substituted with one, two or three substituents independently selected from halogen, C$_{1-6}$alkyl, C$_{1-6}$haloalkyl, OC$_{1-6}$haloalkyl, C$_{0-6}$alk-O—C$_{1-6}$alkyl, —CN, —COOH, and —COOC$_{1-6}$alkyl. In some aspects, the pyrazinyl is substituted with one substituent that is halogen, C$_{1-6}$alkyl, C$_{1-6}$haloalkyl, OC$_{1-6}$haloalkyl, C$_{0-6}$alk-O—C$_{1-6}$alkyl, —CN, —COOH, and —COOC$_{1-6}$alkyl. In some aspects, the pyrazinyl is substituted with two substituents independently selected from halogen, C$_{1-6}$alkyl, C$_{1-6}$haloalkyl, OC$_{1-6}$haloalkyl, C$_{0-6}$alk-O—C$_{1-6}$alkyl, —CN, —COOH, and —COOC$_{1-6}$alkyl. In other aspects, the pyrazinyl is substituted with three substituents independently selected from halogen, C$_{1-6}$alkyl, C$_{1-6}$haloalkyl, OC$_{1-6}$haloalkyl, C$_{0-6}$alk-O—C$_{1-6}$alkyl, —CN, —COOH, and —COOC$_{1-6}$alkyl. In those embodiments wherein the pyrazinyl is substituted with one or more halogen, the halogen may be independently selected from F, Cl, Br, or I, preferably F, Cl, or Br. In those embodiments where the pyrazinyl is substituted with one or more $C_{1-6}$alkyl, the $C_{1-6}$alkyl is independently selected from $C_6$alkyl, $C_5$alkyl, $C_4$alkyl, $C_3$alkyl, ethyl ($C_2$alkyl), or methyl ($C_1$alkyl). In those embodiments wherein the pyrazinyl is substituted with one or more $C_{1-6}$haloalkyl, the $C_{1-6}$haloalkyl is independently selected from, e.g., $CF_3$ or $CHF_2$, preferably $CF_3$. In those embodiments wherein the pyrazinyl is substituted with one or more $OC_{1-6}$haloalkyl, the $OC_{1-6}$haloalkyl is independently selected from, e.g., $OCF_3$ or $OCHF_2$, preferably $OCF_3$. In those embodiments where the pyrazinyl is substituted with one or more $C_{0-6}$alk-O—$C_{1-6}$alkyl, the $C_{0-6}$alk-O—$C_{1-6}$alkyl, is independently selected from, e.g., $C_{1-6}$alk-$OC_{1-6}$alkyl, $C_{1-5}$alk-$OC_{1-6}$alkyl, $C_{1-4}$alk-$OC_{1-6}$alkyl, $C_{1-3}$alk-$OC_{1-6}$alkyl, $C_{1-2}$alk-$OC_{1-6}$alkyl, $C_2$alk-$OC_{1-6}$alkyl, $C_1$alk-$OC_{1-6}$alkyl, $C_0$alk-$OC_{1-6}$alkyl, $C_{0-6}$alk-$OC_{1-5}$alkyl, $C_{0-6}$alk-$OC_{1-5}$alkyl, $C_{0-6}$alk-$OC_{1-4}$alkyl, $C_{0-6}$alk-$OC_{1-3}$alkyl, $C_{0-6}$alk-$OC_{1-2}$alkyl, or $C_{0-6}$alk-$OC_1$alkyl. In some embodiments, the pyrazinyl is substituted with one or more CN. In other embodiments, the pyrazinyl is substituted with one or more COOH.

In those embodiments wherein the pyrazinyl is substituted with one or more —$COOC_{1-6}$alkyl, the —$COOC_{1-6}$alkyl is independently selected from —$COOC_6$alkyl, —$COOC_5$alkyl, —$COOC_4$alkyl, —$COOC_3$alkyl, —$COOC_2$alkyl, and —$COOC_1$alkyl.

In some aspects, $R^4$ is pyridazinyl. In other aspects, $R^4$ is pyridazinyl substituted with one, two or three substituents independently selected from halogen, $C_{1-6}$alkyl, $C_{1-6}$haloalkyl, $OC_{1-6}$haloalkyl, $C_{0-6}$alk-O—$C_{1-6}$alkyl, —CN, —COOH, and —$COOC_{1-6}$alkyl. In some aspects, the pyridazinyl is substituted with one substituent that is halogen, $C_{1-6}$alkyl, $C_{1-6}$haloalkyl, $OC_{1-6}$haloalkyl, $C_{0-6}$alk-O—$C_{1-6}$alkyl, —CN, —COOH, and —$COOC_{1-6}$alkyl. In some aspects, the pyridazinyl is substituted with two substituents independently selected from halogen, $C_{1-6}$alkyl, $C_{1-6}$haloalkyl, $OC_{1-6}$haloalkyl, $C_{0-6}$alk-O—$C_{1-6}$alkyl, —CN, —COOH, and —$COOC_{1-6}$alkyl. In other aspects, the pyridazinyl is substituted with three substituents independently selected from halogen, $C_{1-6}$alkyl, $C_{1-6}$haloalkyl, $OC_{1-6}$haloalkyl, $C_{0-6}$alk-O—$C_{1-6}$alkyl, —CN, —COOH, and —$COOC_{1-6}$alkyl. In those embodiments wherein the pyridazinyl is substituted with one or more halogen, the halogen may be independently selected from F, Cl, Br, or I, preferably F, Cl, or Br. In those embodiments where the pyridazinyl is substituted with one or more $C_{1-6}$alkyl, the $C_{1-6}$alkyl is independently selected from $C_6$alkyl, $C_5$alkyl, $C_4$alkyl, $C_3$alkyl, ethyl ($C_2$alkyl), or methyl ($C_1$alkyl). In those embodiments wherein the pyridazinyl is substituted with one or more $C_{1-6}$haloalkyl, the $C_{1-6}$haloalkyl is independently selected from, e.g., $CF_3$ or $CHF_2$, preferably $CF_3$. In those embodiments wherein the pyridazinyl is substituted with one or more $OC_{1-6}$haloalkyl, the $OC_{1-6}$haloalkyl is independently selected from, e.g., $OCF_3$ or $OCHF_2$, preferably $OCF_3$. In those embodiments where the pyridazinyl is substituted with one or more $C_{0-6}$alk-O—$C_{1-6}$alkyl, the $C_{0-6}$alk-O—$C_{1-6}$alkyl, is independently selected from, e.g., $C_{1-6}$alk-$OC_{1-6}$alkyl, $C_{1-5}$alk-$OC_{1-6}$alkyl, $C_{1-4}$alk-$OC_{1-6}$alkyl, $C_{1-3}$alk-$OC_{1-6}$alkyl, $C_{1-2}$alk-$OC_{1-6}$alkyl, $C_2$alk-$OC_{1-6}$alkyl, $C_1$alk-$OC_{1-6}$alkyl, $C_0$alk-$OC_{1-6}$alkyl, $C_{0-6}$alk-$OC_1$-alkyl, $C_{0-6}$alk-$OC_{1-5}$alkyl, $C_{0-6}$alk-$OC_{1-4}$alkyl, $C_{0-6}$alk-$OC_{1-3}$alkyl, $C_{0-6}$alk-$OC_{1-2}$alkyl, or $C_{0-6}$alk-$OC_1$alkyl. In some embodiments, the pyridazinyl is substituted with one or more CN. In other embodiments, the pyridazinyl is substituted with one or more COOH. In those embodiments wherein the pyridazinyl is substituted with one or more —$COOC_{1-6}$alkyl, the —$COOC_{1-6}$alkyl is independently selected from —$COOC_6$alkyl, —$COOC_5$alkyl, —$COOC_4$alkyl, —$COOC_3$alkyl, —$COOC_2$alkyl, and —$COOC_1$alkyl.

In some aspects, $R^4$ is pyrimidyl. In other aspects, $R^4$ is pyrimidyl substituted with one, two or three substituents independently selected from halogen, $C_{1-6}$alkyl, $C_{1-6}$haloalkyl, $OC_{1-6}$haloalkyl, $C_{0-6}$alk-O—$C_{1-6}$alkyl, —CN, —COOH, and —$COOC_{1-6}$alkyl. In some aspects, the pyrimidyl is substituted with one substituent that is halogen, $C_{1-6}$alkyl, $C_{1-6}$haloalkyl, $OC_{1-6}$haloalkyl, $C_{0-6}$alk-O—$C_{1-6}$alkyl, —CN, —COOH, and —$COOC_{1-6}$alkyl. In some aspects, the pyrimidyl is substituted with two substituents independently selected from halogen, $C_{1-6}$alkyl, $C_{1-6}$haloalkyl, $OC_{1-6}$haloalkyl, $C_{0-6}$alk-O—$C_{1-6}$alkyl, —CN, —COOH, and —$COOC_{1-6}$alkyl. In other aspects, the pyrimidyl is substituted with three substituents independently selected from halogen, $C_{1-6}$alkyl, $C_{1-6}$haloalkyl, $OC_{1-6}$haloalkyl, $C_{0-6}$alk-O—$C_{1-6}$alkyl, —CN, —COOH, and —$COOC_{1-6}$alkyl.

In those embodiments wherein the pyrimidyl is substituted with one or more halogen, the halogen may be independently selected from F, Cl, Br, or I, preferably F, Cl, or Br. In those embodiments where the pyrimidyl is substituted with one or more $C_{1-6}$alkyl, the $C_{1-6}$alkyl is independently selected from $C_6$alkyl, $C_5$alkyl, $C_4$alkyl, $C_3$alkyl, ethyl ($C_2$alkyl), or methyl ($C_1$alkyl). In some embodiments, $R^4$ is 2-methylpyrimidin-5-yl or 2-ethylpyrimidin-5-yl. In those embodiments wherein the pyrimidyl is substituted with one or more $C_{1-6}$haloalkyl, the $C_{1-6}$haloalkyl is independently selected from, e.g., $CF_3$ or $CHF_2$, preferably $CF_3$. In those embodiments wherein the pyrimidyl is substituted with one or more $OC_{1-6}$haloalkyl, the $OC_{1-6}$haloalkyl is independently selected from, e.g., $OCF_3$ or $OCHF_2$, preferably $OCF_3$. In those embodiments where the pyrimidyl is substituted with one or more $C_{0-6}$alk-O—$C_{1-6}$alkyl, the $C_{0-6}$alk-O—$C_{1-6}$alkyl, is independently selected from, e.g., $C_{1-6}$alk-$OC_{1-6}$alkyl, $C_{1-5}$alk-$OC_{1-6}$alkyl, $C_{1-4}$alk-$OC_{1-6}$alkyl, $C_{1-3}$alk-$OC_{1-6}$alkyl, $C_{1-2}$alk-$OC_{1-6}$alkyl, $C_2$alk-$OC_{1-6}$alkyl, $C_1$alk-$OC_{1-6}$alkyl, $C_0$alk-$OC_{1-6}$alkyl, $C_{0-6}$alk-$OC_{1-5}$alkyl, $C_{0-6}$alk-$OC_{1-5}$alkyl, $C_{0-6}$alk-$OC_{1-4}$alkyl, $C_{0-6}$alk-$OC_{1-3}$alkyl, $C_{0-6}$alk-$OC_{1-2}$alkyl, or $C_{0-6}$alk-$OC_1$alkyl. In some embodiments, $R^4$ is 2-ethoxypyrimidin-5-yl. In some embodiments, the pyrimidyl is substituted with one or more CN. In other embodiments, the pyrimidyl is substituted with one or more COOH. In those embodiments wherein the pyrimidyl is substituted with one or more —$COOC_{1-6}$alkyl, the —$COOC_{1-6}$alkyl is independently selected from —$COOC_6$alkyl, —$COOC_5$alkyl, —$COOC_4$alkyl, —$COOC_3$alkyl, —$COOC_2$alkyl, and —$COOC_1$alkyl.

In some aspects, $R^4$ is benzothiazolyl. In other aspects, $R^4$ is benzothiazolyl substituted with one, two or three substituents independently selected from halogen, $C_{1-6}$alkyl, $C_{1-6}$haloalkyl, $OC_{1-6}$haloalkyl, $C_{0-6}$alk-O—$C_{1-6}$alkyl, —CN, —COOH, and —$COOC_{1-6}$alkyl. In some aspects, the benzothiazolyl is substituted with one substituent that is halogen, $C_{1-6}$alkyl, $C_{1-6}$haloalkyl, $OC_{1-6}$haloalkyl, $C_{0-6}$alk-O—$C_{1-6}$alkyl, —CN, —COOH, and —$COOC_{1-6}$alkyl. In some aspects, the benzothiazolyl is substituted with two substituents independently selected from halogen, $C_{1-6}$alkyl, $C_{1-6}$haloalkyl, $OC_{1-6}$haloalkyl, $C_{0-6}$alk-O—$C_{1-6}$alkyl, —CN, —COOH, and —$COOC_{1-6}$alkyl. In other aspects, the benzothiazolyl is substituted with three substituents independently selected from halogen, $C_{1-6}$alkyl, $C_{1-6}$haloalkyl, $OC_{1-6}$haloalkyl, $C_{0-6}$alk-O—$C_{1-6}$alkyl, —CN, —COOH, and —$COOC_{1-6}$alkyl. In those embodiments wherein the benzothiazolyl is substituted with one or more halogen, the halogen may be independently selected from F, Cl, Br, or I, preferably F, Cl, or Br. In those embodiments where the benzothiazolyl is substituted with one or more $C_{1-6}$alkyl, the $C_{1-6}$alkyl is independently selected from $C_6$alkyl, $C_5$alkyl, $C_4$alkyl, $C_3$alkyl, ethyl ($C_2$alkyl), or methyl ($C_1$alkyl). In those embodiments wherein the benzothiazolyl is substituted with one or more $C_{1-6}$haloalkyl, the $C_{1-6}$haloalkyl is independently selected from, e.g., $CF_3$ or $CHF_2$, preferably $CF_3$. In those embodiments wherein the benzothiazolyl is substituted with one or more $OC_{1-6}$haloalkyl, the $OC_{1-6}$haloalkyl is independently selected from, e.g., $OCF_3$ or $OCHF_2$, preferably $OCF_3$. In those embodiments where the benzothiazolyl is substituted with one or more $C_{0-6}$alk-O—$C_{1-6}$alkyl, the $C_{0-6}$alk-O—$C_{1-6}$alkyl, is independently selected from, e.g., $C_{1-6}$alk-$OC_{1-6}$alkyl, $C_{1-5}$alk-$OC_{1-6}$alkyl, $C_{1-4}$alk-$OC_{1-6}$alkyl, $C_{1-3}$alk-$OC_{1-6}$alkyl, $C_{1-2}$alk-$OC_{1-6}$alkyl, $C_2$alk-$OC_{1-6}$alkyl, $C_1$alk-$OC_{1-6}$alkyl, $C_0$alk-$OC_{1-6}$alkyl, $C_{0-6}$alk-$OC_{1-6}$alkyl, $C_{0-6}$alk-$OC_{1-5}$alkyl, $C_{0-6}$alk-$OC_{1-4}$alkyl, $C_{0-6}$alk-$OC_{1-3}$alkyl, $C_{0-6}$alk-$OC_{1-2}$alkyl, or $C_{0-6}$alk-$OC_1$alkyl. In some embodiments, the benzothiazolyl is substituted with one or more CN. In other embodiments, the benzothiazolyl is substituted with one or more COOH. In those embodiments wherein the benzothiazolyl is substituted with one or more —$COOC_{1-6}$alkyl, the —$COOC_{1-6}$alkyl is independently selected from —$COOC_6$alkyl, —$COOC_5$alkyl, —$COOC_4$alkyl, —$COOC_3$alkyl, —$COOC_2$alkyl, and —$COOC_1$alkyl.

Sub-formulas of formula I and II include formulas wherein X is CH, Y is $CHR^6$, and $R^{2A}$ is H, for example:

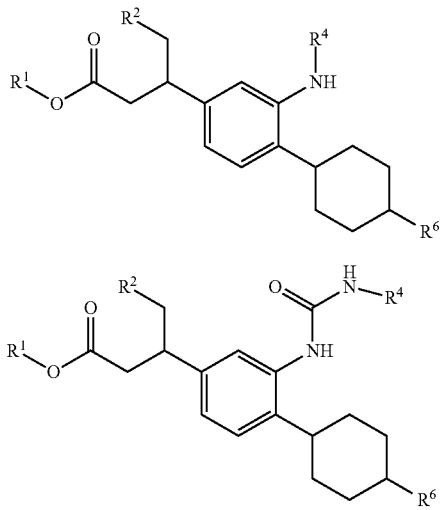

wherein $R^1$ is H or $C_{1-6}$alkyl, $R^2$ is $C_{1-6}$alkyl or $C_0$alk-$OC_{1-6}$alkyl ($OC_{1-6}$alkyl); $R^6$ is H or phenyl; and $R^4$ is phenyl, pyridyl, pyrazinyl, pyridazinyl, pyrimidyl, or benzothiazolyl, each of which is optionally substituted with one, two or three substituents independently selected from halogen, $C_{1-6}$alkyl, $C_{1-6}$haloalkyl, $OC_{1-6}$haloalkyl, $C_{0-6}$alk-O—$C_{1-6}$alkyl, —CN, —COOH, and —$COOC_{1-6}$alkyl. Preferably, in the compounds of formula I-A or II-A, $R^4$ is substituted with one or two, preferably one substituent, that is halogen, $C_{1-6}$alkyl, $C_{1-6}$haloalkyl, $OC_{1-6}$haloalkyl, $C_{0-6}$alk-O—$C_{1-6}$alkyl, —CN, —COOH, and —$COOC_{1-6}$alkyl. The disclosure also encompasses enantiomers and diastereomers of formula I-A and formula II-A. The disclosure also encompasses the pharmaceutically acceptable salts of compounds of formula I-A and II-A. The disclosure also encompasses solvates of compounds of formula I-A and II-A.

Sub-formulas of formula I and II include formulas wherein X is CH, Y is O, and $R^{2A}$ is H, for example:

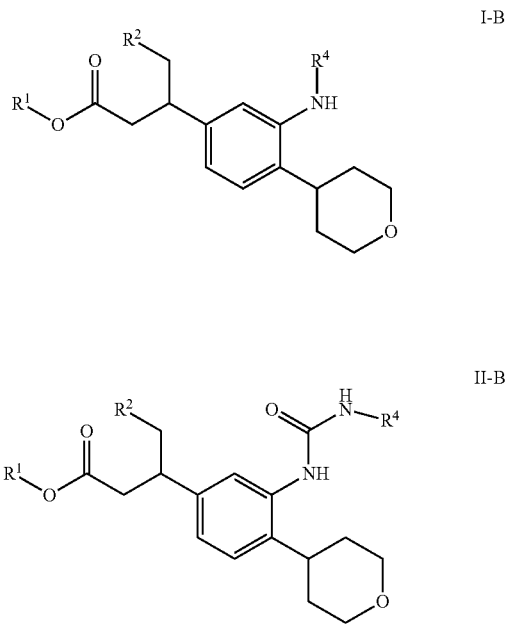

wherein $R^1$ is H or $C_{1-6}$alkyl, $R^2$ is $C_{1-6}$alkyl or $C_0$alk-$OC_{1-6}$alkyl ($OC_{1-6}$alkyl); and $R^4$ is phenyl, pyridyl, pyrazinyl, pyridazinyl, pyrimidyl, or benzothiazolyl, each of which is optionally substituted with one, two or three substituents independently selected from halogen, $C_{1-6}$alkyl, $C_{1-6}$haloalkyl, $OC_{1-6}$haloalkyl, $C_{0-6}$alk-O—$C_{1-6}$alkyl, —CN, —COOH, and —$COOC_{1-6}$alkyl. Preferably, in the compounds of formula I-B or II-B, $R^4$ is substituted with one or two, preferably one substituent, that is halogen, $C_{1-6}$alkyl, $C_{1-6}$haloalkyl, $OC_{1-6}$haloalkyl, $C_{0-6}$alk-O—$C_{1-6}$alkyl, —CN, —COOH, and —$COOC_{1-6}$alkyl. The disclosure also encompasses enantiomers and diastereomers of formula I-B and formula II-B. The disclosure also encompasses the pharmaceutically acceptable salts of compounds of formula I-B and II-B. The disclosure also encompasses solvates of compounds of formula I-B and II-B.

Sub-formulas of formula I and II include formulas wherein X is CH, Y is $NR^7$, and $R^{2A}$ is H, for example:

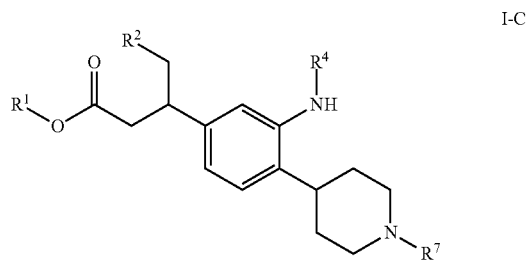

-continued

II-C

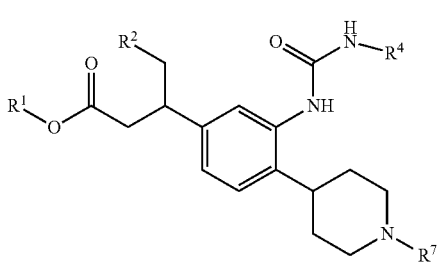

wherein $R^1$ is H or $C_{1-6}$alkyl, $R^2$ is $C_{1-6}$alkyl or $C_0$alk-$OC_{1-6}$alkyl ($OC_{1-6}$alkyl); $R^7$ is H, pyridyl, pyrazinyl, pyridazinyl, pyrimidyl, —COOH, —COO$C_{1-6}$alkyl, or —CO$R^{7A}$ wherein $R^{7A}$ is H, $C_{1-6}$alkyl, pyridyl optionally substituted with $OC_{1-6}$alkyl, pyrazinyl optionally substituted with $OC_{1-6}$alkyl, pyridazinyl optionally substituted with $OC_{1-6}$alkyl, or pyrimidyl optionally substituted with $OC_{1-6}$alky; and $R^4$ is phenyl, pyridyl, pyrazinyl, pyridazinyl, pyrimidyl, or benzothiazolyl, each of which is optionally substituted with one, two or three substituents independently selected from halogen, $C_{1-6}$alkyl, $C_{1-6}$haloalkyl, $OC_{1-6}$haloalkyl, $C_{0-6}$alk-O—$C_{1-6}$alkyl, —CN, —COOH, and —COO$C_{1-6}$alkyl. Preferably, in the compounds of formula I-C or II-C, $R^4$ is substituted with one or two, preferably one substituent, that is halogen, $C_{1-6}$alkyl, $C_{1-6}$haloalkyl, $OC_{1-6}$haloalkyl, $C_{0-6}$alk-O—$C_{1-6}$alkyl, —CN, —COOH, and —COO$C_{1-6}$alkyl. In some aspects, $R^7$ is pyridyl, pyrazinyl, pyridazinyl, or pyrimidyl. In other aspects, $R^7$ is —COOH or —COO$C_{1-6}$alkyl. In some aspects, $R^7$ is —CO$R^{7A}$. The disclosure also encompasses enantiomers and diastereomers of formula I-C and formula II-C. The disclosure also encompasses the pharmaceutically acceptable salts of compounds of formula I-C and II-C. The disclosure also encompasses solvates of compounds of formula I-C and II-C.

Sub-formulas of formula I and II include formulas wherein X is CH, $R^5$ is optionally substituted phenyl, and $R^{2A}$ is H, for example:

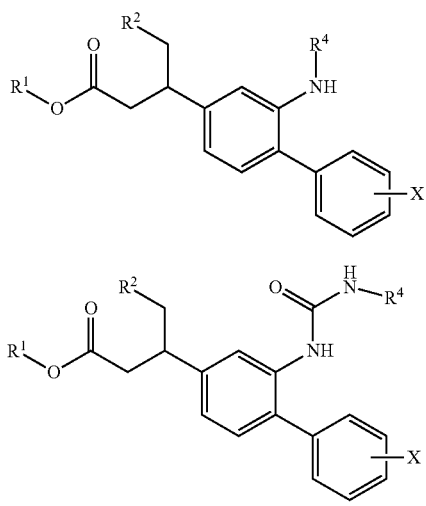

I-D

II-D wherein $R^1$ is H or $C_{1-6}$alkyl, $R^2$ is $C_{1-6}$alkyl or $C_0$alk-$OC_{1-6}$alkyl ($OC_{1-6}$alkyl); X is one or more halogen, $C_{0-6}$alk-O—$C_{1-6}$alkyl, or —CN substituent; and $R^4$ is phenyl, pyridyl, pyrazinyl, pyridazinyl, pyrimidyl, or benzothiazolyl, each of which is optionally substituted with one, two or three substituents independently selected from halogen, $C_{1-6}$alkyl, $C_{1-6}$haloalkyl, $OC_{1-6}$haloalkyl, $C_{0-6}$alk-O—$C_{1-6}$alkyl, —CN, —COOH, and —COO$C_{1-6}$alkyl. Preferably, in the compounds of formula I-D or II-D, $R^4$ is substituted with one or two, preferably one substituent, that is halogen, $C_{1-6}$alkyl, $C_{1-6}$haloalkyl, $OC_{1-6}$haloalkyl, $C_{0-6}$alk-O—$C_{1-6}$alkyl, —CN, —COOH, and —COO$C_{1-6}$alkyl. The disclosure also encompasses enantiomers and diastereomers of formula I-D and formula II-D. The disclosure also encompasses the pharmaceutically acceptable salts of compounds of formula I-D and II-D. The disclosure also encompasses solvates of compounds of formula I-D and II-D.

Sub-formulas of formula I and II include formulas wherein X is CH, $R^5$ is optionally substituted heteroaryl, and $R^{2A}$ is H, for example:

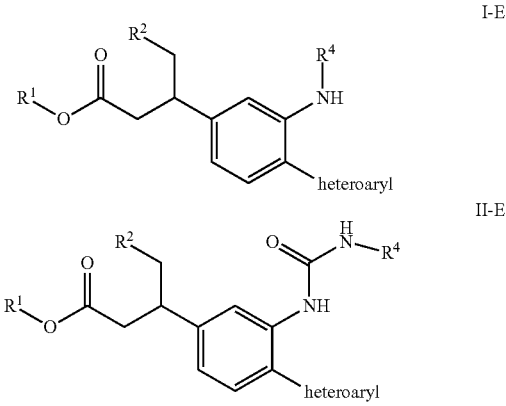

I-E

II-E wherein $R^1$ is H or $C_{1-6}$alkyl, $R^2$ is $C_{1-6}$alkyl or $C_0$alk-$OC_{1-6}$alkyl ($OC_{1-6}$alkyl); heteroaryl is pyrazolyl, pyrazinyl, isoxazolyl, thiazolyl, benzodioxazolyl, furanyl, dihydrobenzofuranyl, benzofuranyl, benzothiophenyl, pyrimidinyl, indazolyl, pyridinyl, benzothiazolyl, imidazo[1,2-a]pyridinyl, imidazo[1,5-a]pyridinyl, benzo[c][1,2,5]oxadiazolyl, or pyrazolo[1,5-a]pyrimidinyl, wherein the heteroaryl is optionally substituted with one, two or three substituents independently selected from halogen, optionally substituted phenyl, optionally substituted benzyl, optionally substituted $C_{1-6}$alkyl, $C_{1-6}$haloalkyl, $C_{0-6}$alk-O—$C_{1-6}$alkyl, heterocyclyl, and —CN; and $R^4$ is phenyl, pyridyl, pyrazinyl, pyridazinyl, pyrimidyl, or benzothiazolyl, each of which is optionally substituted with one, two or three substituents independently selected from halogen, $C_{1-6}$alkyl, $C_{1-6}$haloalkyl, $OC_{1-6}$haloalkyl, $C_{0-6}$alk-O—$C_{1-6}$alkyl, —CN, —COOH, and —COO$C_{1-6}$alkyl. Preferably, in the compounds of formula I-E or II-E, $R^4$ is substituted with one or two, preferably one substituent, that is halogen, $C_{1-6}$alkyl, $C_{1-6}$haloalkyl, $OC_{1-6}$haloalkyl, $C_{0-6}$alk-O—$C_{1-6}$alkyl, —CN, —COOH, and —COO$C_{1-6}$alkyl. The disclosure also encompasses enantiomers and diastereomers of formula I-E and formula II-E. The disclosure also encompasses the pharmaceutically acceptable salts of compounds of formula I-E and II-E. The disclosure also encompasses solvates of compounds of formula I-E and II-E.

Other Embodiments of the Disclosure

In another embodiment, the present disclosure provides a composition comprising one or more compounds of the present disclosure and/or a pharmaceutically acceptable salt thereof, a stereoisomer thereof, a tautomer thereof, or a solvate thereof.

In another embodiment, the present disclosure provides a pharmaceutical composition comprising a pharmaceutically acceptable carrier and at least one of the compounds of the present disclosure and/or a pharmaceutically acceptable salt thereof, a stereoisomer thereof, a tautomer thereof, or a solvate thereof.

In another embodiment, the present disclosure provides a pharmaceutical composition, comprising a pharmaceutically acceptable carrier and a therapeutically effective amount of at least one of the compounds of the present disclosure and/or a pharmaceutically acceptable salt thereof, a stereoisomer thereof, a tautomer thereof, or a solvate thereof.

In another embodiment, the present disclosure provides a process for making a compound of the present disclosure and/or a pharmaceutically acceptable salt thereof, a stereoisomer thereof, a tautomer thereof, or a solvate thereof.

In another embodiment, the present disclosure provides an intermediate for making a compound of the present disclosure and/or a pharmaceutically acceptable salt thereof, a stereoisomer thereof, a tautomer thereof, or a solvate thereof.

In another embodiment, the present disclosure provides a method for the treatment and/or prophylaxis of various types of cancer, viral infections and/or autoimmune diseases, comprising administering to a patient in need of such treatment and/or prophylaxis a therapeutically effective amount of one or more compounds of the present disclosure and/or a pharmaceutically acceptable salt thereof, a stereoisomer thereof or a tautomer thereof, alone, or, optionally, in combination with another compound of the present disclosure and/or at least one other type of therapeutic agent, such as a chemotherapeutic agent or a signal transductor inhibitor.

In another embodiment, the present disclosure provides a compound of the present disclosure, and/or a pharmaceutically acceptable salt thereof, a stereoisomer thereof or a tautomer thereof, for use in therapy.

In another embodiment, the present disclosure provides a combined preparation of a compound of the present disclosure, and/or a pharmaceutically acceptable salt thereof, a stereoisomer thereof or a tautomer thereof, and additional therapeutic agent(s) for simultaneous, separate or sequential use in therapy.

In another embodiment, the present disclosure provides a combined preparation of a compound of the present disclosure, and/or a pharmaceutically acceptable salt thereof, a stereoisomer thereof or a tautomer thereof, and additional therapeutic agent(s) for simultaneous, separate or sequential use in the treatment and/or prophylaxis of multiple diseases or disorders associated with the enzymatic activity of IDO.

In another aspect, the disclosure provides a method of treating a patient suffering from or susceptible to a medical condition that is sensitive to enzymatic activity of IDO. A number of medical conditions can be treated. The method comprises administering to the patient a therapeutically effective amount of a composition comprising a compound described herein and/or a pharmaceutically acceptable salt thereof, a stereoisomer thereof or a tautomer thereof. For example, the compounds described herein may be used to treat or prevent viral infections, proliferative diseases (e.g., cancer), and autoimmune diseases.

Therapeutic Applications

The compounds and pharmaceutical compositions of the present disclosure are useful in treating or preventing any disease or conditions that are sensitive to enzymatic activity of IDO. These include viral and other infections (e.g., skin infections, GI infection, urinary tract infections, genitourinary infections, systemic infections), proliferative diseases (e.g., cancer), and autoimmune diseases (e.g., rheumatoid arthritis, lupus). The compounds and pharmaceutical compositions may be administered to animals, preferably mammals (e.g., domesticated animals, cats, dogs, mice, rats), and more preferably humans. Any method of administration may be used to deliver the compound or pharmaceutical composition to the patient. In certain embodiments, the compound or pharmaceutical composition is administered orally. In other embodiments, the compound or pharmaceutical composition is administered parenterally.

Compounds of the disclosure can modulate activity of the enzyme indoleamine-2,3-dioxygenase (IDO). The term "modulate" is meant to refer to an ability to increase or decrease activity of an enzyme or receptor. Accordingly, compounds of the disclosure can be used in methods of modulating IDO by contacting the enzyme with any one or more of the compounds or compositions described herein. In some embodiments, compounds of the present disclosure can act as inhibitors of IDO. In further embodiments, the compounds of the disclosure can be used to modulate activity of IDO in cell or in an individual in need of modulation of the enzyme by administering a modulating (e.g., inhibiting) amount of a compound of the disclosure.

Compounds of the disclosure can inhibit activity of the enzyme indoleamine-2,3-dioxygenase (IDO). For example, the compounds of the disclosure can be used to inhibit activity of IDO in cell or in an individual in need of modulation of the enzyme by administering an inhibiting amount of a compound of the disclosure.

The present disclosure further provides methods of inhibiting the degradation of tryptophan in a system containing cells expressing IDO such as a tissue, living organism, or cell culture. In some embodiments, the present disclosure provides methods of altering (e.g., increasing) extracellular tryptophan levels in a mammal by administering an effective amount of a compound of composition provided herein. Methods of measuring tryptophan levels and tryptophan degradation are routine in the art.

The present disclosure further provides methods of inhibiting immunosuppression such as IDO-mediated immunosuppression in a patient by administering to the patient an effective amount of a compound or composition recited herein. IDO-mediated immunosuppression has been associated with, for example, cancers, tumor growth, metastasis, viral infection, and viral replication.

The present disclosure further provides methods of treating diseases associated with activity or expression, including abnormal activity and/or overexpression, of IDO in an individual (e.g., patient) by administering to the individual in need of such treatment a therapeutically effective amount or dose of a compound of the present disclosure or a pharmaceutical composition thereof. Example diseases can include any disease, disorder or condition that is directly or indirectly linked to expression or activity of the IDO enzyme, such as over expression or abnormal activity. An IDO-associated disease can also include any disease, disorder or condition that can be prevented, ameliorated, or cured by modulating enzyme activity. Examples of IDO-associated diseases include cancer, viral infection such as HIV infection, HCV infection, depression, neurodegenerative disorders such as Alzheimer's disease and Huntington's disease, trauma, age-related cataracts, organ transplantation (e.g., organ transplant rejection), and autoimmune diseases including asthma, rheumatoid arthritis, multiple sclerosis, allergic inflammation, inflammatory bowel disease, psoriasis and systemic lupus erythematosus.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the IDO enzyme with a compound of the disclosure includes the administration of a compound of the present disclosure to an individual or patient, such as a human, having IDO, as well as, for example, introducing a compound of the disclosure into a sample containing a cellular or purified preparation containing the IDO enzyme.

The term "IDO inhibitor" refers to an agent capable of inhibiting the activity of indoleamine 2,3-dioxygenase (IDO) and thereby reversing IDO-mediated immunosuppression. The IDO inhibitor may inhibit IDO1 and/or IDO2 (INDOL1). An IDO inhibitor may be a reversible or irreversible IDO inhibitor. "A reversible IDO inhibitor" is a compound that reversibly inhibits IDO enzyme activity either at the catalytic site or at a non-catalytic site and "an irreversible IDO inhibitor" is a compound that irreversibly destroys IDO enzyme activity.

Types of cancers that may be treated with the compounds of this disclosure include, but are not limited to, brain cancers, skin cancers, bladder cancers, ovarian cancers, breast cancers, gastric cancers, pancreatic cancers, prostate cancers, colon cancers, blood cancers, lung cancers and bone cancers. Examples of such cancer types include neuroblastoma, intestine carcinoma such as rectum carcinoma, colon carcinoma, familiar adenomatous polyposis carcinoma and hereditary non-polyposis colorectal cancer, esophageal carcinoma, labial carcinoma, larynx carcinoma, hypopharynx carcinoma, tongue carcinoma, salivary gland carcinoma, gastric carcinoma, adenocarcinoma, medullary thyroid carcinoma, papillary thyroid carcinoma, renal carcinoma, kidney parenchymal carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, diffuse large B-cell lymphoma (DLBCL), hepatocellular carcinoma, gall bladder carcinoma, bronchial carcinoma, small cell lung carcinoma, non-small cell lung carcinoma, multiple myeloma, basalioma, teratoma, retinoblastoma, choroid melanoma, seminoma, rhabdomyosarcoma, craniopharyngioma, osteosarcoma, chondrosarcoma, myosarcoma, liposarcoma, fibrosarcoma, Ewing sarcoma and plasmacytoma.

Thus, according to another embodiment, the disclosure provides a method of treating an autoimmune disease by providing to a patient in need thereof a compound or composition of the present disclosure. Examples of such autoimmune diseases include, but are not limited to, collagen diseases such as rheumatoid arthritis, systemic lupus erythematosus, Sharp's syndrome, CREST syndrome (calcinosis, Raynaud's syndrome, esophageal dysmotility, telangiectasia), dermatomyositis, vasculitis (Morbus Wegener's) and Sjögren's syndrome, renal diseases such as Goodpasture's syndrome, rapidly-progressing glomerulonephritis and membranoproliferative glomerulonephritis type II, endocrine diseases such as type-I diabetes, autoimmune polyendocrinopathy-candidiasis-ectodermal dystrophy (APECED), autoimmune parathyroidism, pernicious anemia, gonad insufficiency, idiopathic Morbus Addison's, hyperthyreosis, Hashimoto's thyroiditis and primary myxedema, skin diseases such as pemphigus vulgaris, bullous pemphigoid, herpes gestationis, epidermolysis bullosa and erythema multiforme major, liver diseases such as primary biliary cirrhosis, autoimmune cholangitis, autoimmune hepatitis type-1, autoimmune hepatitis type-2, primary sclerosing cholangitis, neuronal diseases such as multiple sclerosis, myasthenia gravis, myasthenic Lambert-Eaton syndrome, acquired neuromyotomy, Guillain-Barré syndrome (Muller-Fischer syndrome), stiff-man syndrome, cerebellar degeneration, ataxia, opsoclonus, sensoric neuropathy and achalasia, blood diseases such as autoimmune hemolytic anemia, idiopathic thrombocytopenic purpura (Morbus Werlhof), infectious diseases with associated autoimmune reactions such as AIDS, malaria and Chagas disease.

One or more additional pharmaceutical agents or treatment methods such as, for example, anti-viral agents, chemotherapeutics or other anticancer agents, immune enhancers, immunosuppressants, radiation, anti-tumor and anti-viral vaccines, cytokine therapy (e.g., IL2 and GM-CSF), and/or tyrosine kinase inhibitors can be optionally used in combination with the compounds of the present disclosure for treatment of IDO-associated diseases, disorders or conditions. The agents can be combined with the present compounds in a single dosage form, or the agents can be administered simultaneously or sequentially as separate dosage forms.

Suitable chemotherapeutic or other anticancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (CYTOXAN®), ifosfamide, melphalan, chlorambucil, pipobroman, triethylene-melamine, triethylenethiophosphoramine, busulfan, carmustine, lomustine, streptozocin, dacarbazine, and temozolomide.

In the treatment of melanoma, suitable agents for use in combination with the compounds of the present disclosure include: dacarbazine (DTIC), optionally, along with other chemotherapy drugs such as carmustine (BCNU) and cisplatin; the "Dartmouth regimen", which consists of DTIC, BCNU, cisplatin and tamoxifen; a combination of cisplatin, vinblastine, and DTIC, temozolomide or YERVOY®. Compounds according to the disclosure may also be combined with immunotherapy drugs, including cytokines such as interferon alpha, interleukin 2, and tumor necrosis factor (TNF) in the treatment of melanoma.

Compounds of the disclosure may also be used in combination with vaccine therapy in the treatment of melanoma. Anti-melanoma vaccines are, in some ways, similar to the anti-virus vaccines which are used to prevent diseases caused by viruses such as polio, measles, and mumps. Weakened melanoma cells or parts of melanoma cells called antigens may be injected into a patient to stimulate the body's immune system to destroy melanoma cells.

Melanomas that are confined to the arms or legs may also be treated with a combination of agents including one or more compounds of the disclosure, using a hyperthermic isolated limb perfusion technique. This treatment protocol temporarily separates the circulation of the involved limb from the rest of the body and injects high doses of chemotherapy into the artery feeding the limb, thus providing high doses to the area of the tumor without exposing internal organs to these doses that might otherwise cause severe side effects. Usually the fluid is warmed to 102° to 104° F. Melphalan is the drug most often used in this chemotherapy procedure. This can be given with another agent called tumor necrosis factor (TNF).

Suitable chemotherapeutic or other anticancer agents include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anticancer agents further include, for example, certain natural products and their derivatives (for example, vinca alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel (Taxol), mithramycin, deoxycoformycin, mitomycin-C, L-asparaginase, interferons (especially IFN-α), etoposide, and teniposide.

Other cytotoxic agents include navelbene, CPT-11, anastrazole, letrazole, capecitabine, reloxafine, and droloxafine.

Also suitable are cytotoxic agents such as epidophyllotoxin; an antineoplastic enzyme; a topoisomerase inhibitor; procarbazine; mitoxantrone; platinum coordination complexes such as cisplatin and carboplatin; biological response modifiers; growth inhibitors; antihormonal therapeutic agents; leucovorin; tegafur; and haematopoietic growth factors.

Other anticancer agent(s) include antibody therapeutics such as trastuzumab (HERCEPTIN®), antibodies to costimulatory molecules such as CTLA-4, 4-1BB and PD-1, or antibodies to cytokines (IL-1O or TGF-β).

Other anticancer agents also include those that block immune cell migration such as antagonists to chemokine receptors, including CCR2 and CCR4.

Other anticancer agents also include those that augment the immune system such as adjuvants or adoptive T cell transfer.

Anticancer vaccines include dendritic cells, synthetic peptides, DNA vaccines and recombinant viruses.

The pharmaceutical composition of the disclosure may optionally include at least one signal transduction inhibitor (STI). A "signal transduction inhibitor" is an agent that selectively inhibits one or more vital steps in signaling pathways, in the normal function of cancer cells, thereby leading to apoptosis. Suitable STIs include, but are not limited to: (i) bcr/abl kinase inhibitors such as, for example, STI 571 (GLEEVEC®); (ii) epidermal growth factor (EGF) receptor inhibitors such as, for example, kinase inhibitors (IRESSA®, SSI-774) and antibodies (Imclone: C225 [Goldstein et al., Clin. Cancer Res., 1:1311-1318 (1995)], and Abgenix: ABX-EGF); (iii) her-2/neu receptor inhibitors such as farnesyl transferase inhibitors (FTI) such as, for example, L-744,832 (Kohl et al., Nat. Med., 1(8):792-797 (1995)); (iv) inhibitors of Akt family kinases or the Akt pathway, such as, for example, rapamycin (see, for example, Sekulic et al., Cancer Res., 60:3504-3513 (2000)); (v) cell cycle kinase inhibitors such as, for example, flavopiridol and UCN-O1 (see, for example, Sausville, Curr. Med. Chem. Anti-Canc. Agents, 3:47-56 (2003)); and (vi) phosphatidyl inositol kinase inhibitors such as, for example, LY294002 (see, for example, Vlahos et al., J. Biol. Chem., 269:5241-5248 (1994)). Alternatively, at least one STI and at least one IDO inhibitor may be in separate pharmaceutical compositions. In a specific embodiment of the present disclosure, at least one IDO inhibitor and at least one STI may be administered to the patient concurrently or sequentially. In other words, at least one IDO inhibitor may be administered first, at least one STI may be administered first, or at least one IDO inhibitor and at least one STI may be administered at the same time. Additionally, when more than one IDO inhibitor and/or STI is used, the compounds may be administered in any order.

The present disclosure further provides a pharmaceutical composition for the treatment of a chronic viral infection in a patient comprising at least one IDO inhibitor, optionally, at least one chemotherapeutic drug, and, optionally, at least one antiviral agent, in a pharmaceutically acceptable carrier. The pharmaceutical compositions may include at least one IDO inhibitor of the instant disclosure in addition to at least one established (known) IDO inhibitor. In a specific embodiment, at least one of the IDO inhibitors of the pharmaceutical composition is selected from the group consisting of compounds of formulas I and II, and sub-formulae thereof.

Also provided is a method for treating a chronic viral infection in a patient by administering an effective amount of the above pharmaceutical composition.

In a specific embodiment of the present disclosure, at least one IDO inhibitor and at least one chemotherapeutic agent may be administered to the patient concurrently or sequentially. In other words, at least one IDO inhibitor may be administered first, at least one chemotherapeutic agent may be administered first, or at least one IDO inhibitor and the at least one STI may be administered at the same time. Additionally, when more than one IDO inhibitor and/or chemotherapeutic agent is used, the compounds may be administered in any order. Similarly, any antiviral agent or STI may also be administered at any point in comparison to the administration of an IDO inhibitor.

Chronic viral infections that may be treated using the present combinatorial treatment include, but are not limited to, diseases caused by: hepatitis C virus (HCV), human papilloma virus (HPV), cytomegalovirus (CMV), herpes simplex virus (HSV), Epstein-Barr virus (EBV), varicella zoster virus, Coxsackie virus, human immunodeficiency virus (HIV). Notably, parasitic infections (e.g., malaria) may also be treated by the above methods wherein compounds known to treat the parasitic conditions are optionally added in place of the antiviral agents.

In yet another embodiment, the pharmaceutical compositions comprising at least one IDO inhibitor of the instant disclosure may be administered to a patient to prevent arterial restenosis, such as after balloon endoscopy or stent placement. In a particular embodiment, the pharmaceutical composition further comprises at least one taxane (e.g., paclitaxel (Taxol); see, e.g., Scheller et al., Circulation, 110:810-814 (2004)).

Suitable antiviral agents contemplated for use in combination with the compounds of the present disclosure can comprise nucleoside and nucleotide reverse transcriptase inhibitors (NRTIs), non-nucleoside reverse transcriptase inhibitors (NNRTIs), protease inhibitors and other antiviral drugs.

Examples of suitable NRTIs include zidovudine (AZT); didanosine (ddI); zalcitabine (ddC); stavudine (d4T); lamivudine (3TC); abacavir (1592U89); adefovir dipivoxil

[bis(POM)-PMEA]; lobucavir (BMS-180194); BCH-I0652; emtricitabine [(−)-FTC]; beta-L-FD4 (also called beta-L-D4C and named beta-L-2',3'-dicleoxy-5-fluoro-cytidene); DAPD, ((−)-beta-D-2,6-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2,4 (1H,3H)-pyrimidinedione); and (+)-calanolide A (NSC-675451) and B. Typical suitable protease inhibitors include saquinavir (Ro 31-8959); ritonavir (ABT-538); indinavir (MK-639); nelfinavir (AG-1343); amprenavir (141W94); lasinavir (BMS-234475); DMP-450; BMS-2322623; ABT-378; and AG-1549. Other antiviral agents include hydroxyurea, ribavirin, IL-2, IL-12, pentafuside and Yissum Project No. 11607.

Combination with an Immuno-Oncology Agent

Further provided herein are methods of treatment wherein a compound of Formula I or formula II (or a sub-formula thereof) is administered with one or more immuno-oncology agents. The immuno-oncology agents used herein, also known as cancer immunotherapies, are effective to enhance, stimulate, and/or upregulate immune responses in a subject.

In one aspect, the Compound of Formula I or formula II (or sub-formula thereof) is sequentially administered prior to administration of the immuno-oncology agent. In another aspect, the Compound of Formula I or formula II is administered concurrently with the immunology-oncology agent. In yet another aspect, the Compound of Formula I or formula II (or sub-formula thereof) is sequentially administered after administration of the immuno-oncology agent.

In another aspect, the Compound of Formula I or formula II (or sub-formula thereof) may be co-formulated with an immuno-oncology agent.

Immuno-oncology agents include, for example, a small molecule drug, antibody, or other biologic or small molecule. Examples of biologic immuno-oncology agents include, but are not limited to, cancer vaccines, antibodies, and cytokines. In one aspect, the antibody is a monoclonal antibody. In another aspect, the monoclonal antibody is humanized or human.

In one aspect, the immuno-oncology agent is (i) an agonist of a stimulatory (including a co-stimulatory) receptor or (ii) an antagonist of an inhibitory (including a co-inhibitory) signal on T cells, both of which result in amplifying antigen-specific T cell responses (often referred to as immune checkpoint regulators).

Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTβR, Lymphotoxin α 1β2, FAS, FASL, RELT, DR6, TROY, NGFR.

In another aspect, the immuno-oncology agent is a cytokine that inhibits T cell activation (e.g., IL-6, IL-10, TGF-β, VEGF, and other immunosuppressive cytokines) or a cytokine that stimulates T cell activation, for stimulating an immune response.

In one aspect, T cell responses can be stimulated by a combination of the Compound of Formula I or formula II (or sub-formula thereof) and one or more of (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4, and (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD28H.

Other agents that can be combined with the Compound of Formula I or formula II (or sub-formula thereof) for the treatment of cancer include antagonists of inhibitory receptors on NK cells or agonists of activating receptors on NK cells. For example, the Compound of Formula I or formula II (or sub-formula thereof) can be combined with antagonists of KIR, such as lirilumab.

Yet other agents for combination therapies include agents that inhibit or deplete macrophages or monocytes, including but not limited to CSF-1R antagonists such as CSF-1R antagonist antibodies including RG7155 (WO 11/70024, WO 11/107553, WO 11/131407, WO 13/87699, WO 13/119716, WO 13/132044) or FPA-008 (WO 11/140249, WO 13/169264, WO 14/036357).

In another aspect, the Compound of Formula I or formula II (or sub-formula thereof) can be used with one or more of agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell anergy or exhaustion) and agents that trigger innate immune activation and/or inflammation at tumor sites.

In one aspect, the immuno-oncology agent is a CTLA-4 antagonist, such as an antagonistic CTLA-4 antibody. Suitable CTLA-4 antibodies include, for example, YERVOY® (ipilimumab) or tremelimumab.

In another aspect, the immuno-oncology agent is a PD-1 antagonist, such as an antagonistic PD-1 antibody. Suitable PD-1 antibodies include, for example, OPDIVO® (nivolumab), KEYTRUDA® (pembrolizumab), or MEDI-0680 (AMP-514; WO 2012/145493). The immuno-oncology agent may also include pidilizumab (CT-011), though its specificity for PD-1 binding has been questioned. Another approach to target the PD-1 receptor is the recombinant protein composed of the extracellular domain of PD-L2 (B7-DC) fused to the Fc portion of IgG1, called AMP-224

In another aspect, the immuno-oncology agent is a PD-L1 antagonist, such as an antagonistic PD-L1 antibody. Suitable PD-L1 antibodies include, for example, MPDL3280A (RG7446; WO 2010/077634), durvalumab (MED14736), BMS-936559 (WO 2007/005874), and MSB0010718C (WO 2013/79174).

In another aspect, the immuno-oncology agent is a LAG-3 antagonist, such as an antagonistic LAG-3 antibody. Suitable LAG3 antibodies include, for example, BMS-986016

(WO 10/19570, WO 14/08218), or IMP-731 or IMP-321 (WO 08/132601, WO 09/44273).

In another aspect, the immuno-oncology agent is a CD137 (4-1BB) agonist, such as an agonistic CD137 antibody. Suitable CD137 antibodies include, for example, urelumab and PF-05082566 (WO 12/32433).

In another aspect, the immuno-oncology agent is a GITR agonist, such as an agonistic GITR antibody. Suitable GITR antibodies include, for example, BMS-986153, BMS-986156, TRX-518 (WO 06/105021, WO 09/009116) and MK-4166 (WO 11/028683).

In another aspect, the immuno-oncology agent is an IDO antagonist. Suitable IDO antagonists include, for example, INCB-024360 (WO 2006/122150, WO 07/75598, WO 08/36653, WO 08/36642), indoximod, or NLG-919 (WO 09/73620, WO 09/1156652, WO 11/56652, WO 12/142237).

In another aspect, the immuno-oncology agent is an OX40 agonist, such as an agonistic OX40 antibody. Suitable OX40 antibodies include, for example, MEDI-6383 or MEDI-6469.

In another aspect, the immuno-oncology agent is an OX40L antagonist, such as an antagonistic OX40 antibody. Suitable OX40L antagonists include, for example, RG-7888 (WO 06/029879).

In another aspect, the immuno-oncology agent is a CD40 agonist, such as an agonistic CD40 antibody. In yet another embodiment, the immuno-oncology agent is a CD40 antagonist, such as an antagonistic CD40 antibody. Suitable CD40 antibodies include, for example, lucatumumab or dacetuzumab.

In another aspect, the immuno-oncology agent is a CD27 agonist, such as an agonistic CD27 antibody. Suitable CD27 antibodies include, for example, varlilumab.

In another aspect, the immuno-oncology agent is MGA271 (to B7H3) (WO 11/109400).

The present disclosure also includes pharmaceutical kits useful, for example, in the treatment or prevention of IDO-associated diseases or disorders, obesity, diabetes and other diseases referred to herein which include one or more containers containing a pharmaceutical composition comprising a therapeutically effective amount of a compound of the disclosure. Such kits can further include, if desired, one or more of various conventional pharmaceutical kit components, such as, for example, containers with one or more pharmaceutically acceptable carriers, additional containers, as will be readily apparent to those skilled in the art. Instructions, either as inserts or as labels, indicating quantities of the components to be administered, guidelines for administration, and/or guidelines for mixing the components, can also be included in the kit.

The combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Combination therapy also can embrace the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

Pharmaceutical Compositions and Dosing

The disclosure also provides pharmaceutically acceptable compositions which comprise a therapeutically effective amount of one or more of the compounds of Formula I and/or Formula II (or sub-formula thereof), formulated together with one or more pharmaceutically acceptable carriers (additives) and/or diluents, and optionally, one or more additional therapeutic agents described above.

The compounds of this disclosure can be administered for any of the uses described herein by any suitable means, for example, orally, such as tablets, capsules (each of which includes sustained release or timed release formulations), pills, powders, granules, elixirs, tinctures, suspensions (including nanosuspensions, microsuspensions, spray-dried dispersions), syrups, and emulsions; sublingually; buccally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient.

The term "pharmaceutical composition" means a composition comprising a compound of the disclosure in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms.

Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Allen, Jr., L. V. et al., *Remington: The Science and Practice of Pharmacy* (2 Volumes), 22nd Edition, Pharmaceutical Press (2012).

The dosage regimen for the compounds of the present disclosure will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.001 to about 5000 mg per day, preferably between about 0.01 to about 1000 mg per day, and most preferably between about 0.1 to about 250 mg per day. Intravenously, the most preferred doses will range from about 0.01 to about 10 mg/kg/minute during a constant rate infusion. Compounds of this disclosure may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present disclosure (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present disclosure (250 mg) into a vial, aseptically freeze-drying and sealing. For use, the contents of the vial are mixed with 2 mL of physiological saline, to produce an injectable preparation.

The present disclosure includes within its scope pharmaceutical compositions comprising, as an active ingredient, a therapeutically effective amount of at least one of the compounds of the present disclosure, alone or in combination with a pharmaceutical carrier. Optionally, compounds of the present disclosure can be used alone, in combination with other compounds of the disclosure, or in combination with one or more other therapeutic agent(s), e.g., an anti-cancer agent or other pharmaceutically active material.

Regardless of the route of administration selected, the compounds of the present disclosure, which may be used in a suitable hydrated form, and/or the pharmaceutical compositions of the present disclosure, are formulated into pharmaceutically acceptable dosage forms by conventional methods known to those of skill in the art.

Actual dosage levels of the active ingredients in the pharmaceutical compositions of this disclosure may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present disclosure employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the disclosure employed in the pharmaceutical composition at levels lower than that required in order to achieve the desired therapeutic effect and gradually increase the dosage until the desired effect is achieved.

In general, a suitable daily dose of a compound of the disclosure will be that amount of the compound which is the lowest dose effective to produce a therapeutic effect. Such an effective dose will generally depend upon the factors described above.

If desired, the effective daily dose of the active compound may be administered as two, three, four, five, six or more sub-doses administered separately at appropriate intervals throughout the day, optionally, in unit dosage forms. In certain aspects of the disclosure, dosing is one administration per day.

While it is possible for a compound of the present disclosure to be administered alone, it is preferable to administer the compound as a pharmaceutical formulation (composition).

Definitions

Unless specifically stated otherwise herein, references made in the singular may also include the plural. For example, "a" and "an" may refer to either one, or one or more.

Unless otherwise indicated, any heteroatom with unsatisfied valences is assumed to have hydrogen atoms sufficient to satisfy the valences.

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the disclosure. Many geometric isomers of C=C double bonds, C=N double bonds, ring systems, and the like can also be present in the compounds, and all such stable isomers are contemplated in the present disclosure. Cis- and trans- (or E- and Z-) geometric isomers of the compounds of the present disclosure are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present disclosure and intermediates made therein are considered to be part of the present disclosure. When enantiomeric or diastereomeric products are prepared, they may be separated by conventional methods, for example, by chromatography or fractional crystallization. Depending on the process conditions the end products of the present disclosure are obtained either in free (neutral) or salt form. Both the free form and the salts of these end products are within the scope of the disclosure. If so desired, one form of a compound may be converted into another form. A free base or acid may be converted into a salt; a salt may be converted into the free compound or another salt; a mixture of isomeric compounds of the present disclosure may be separated into the individual isomers. Compounds of the present disclosure, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the disclosure.

For purposes of clarity and in accordance with standard convention in the art, the symbol $\text{\textbardbl}$— is used in formulas and tables to show the bond that is the point of attachment of the moiety or substituent to the core/nucleus of the structure.

Additionally, for purposes of clarity, where a substituent has a dash (-) that is not between two letters or symbols; this is used to indicate a point of attachment for a substituent. For example, —CONH$_2$ is attached through the carbon atom.

Additionally, for purposes of clarity, when there is no substituent shown at the end of a solid line, this indicates that there is a methyl (CH$_3$) group connected to the bond.

As used herein, the terms "alkyl" and "alkylene" (also referred to as "alk") are intended to include both branched and straight-chain saturated aliphatic hydrocarbon groups having the specified number of carbon atoms. For example, "C$_1$-C$_6$ alkyl" or "C$_{1-6}$ alkyl" denotes alkyl having 1 to 6 carbon atoms. Example alkyl groups include, but are not limited to, methyl (C$_1$, Me), ethyl (C$_2$, Et), propyl (C$_3$, e.g., n-propyl and isopropyl), butyl (C$_4$, e.g., n-butyl, isobutyl, t-butyl), pentyl (C$_5$, e.g., n-pentyl, isopentyl, neopentyl), and hexyl variants (C$_6$). "C$_1$-C$_6$alkylene" denotes alkylene having 1 to 6 carbon atoms. Example alkylene groups include, but are not limited to, methylene (—CH$_2$—), ethylene (—CH$_2$CH$_2$—), and the like.

As used herein, "C$_{2-6}$alkenylene" is intended to include both branched and straight-chain hydrocarbon groups having the specified number of carbon atoms and at least one double bond. Example alkenylene groups include ethenyl, propenyl, butenyl, methylbutenyl, methylpenentyl, and the like.

As used herein, "aryl" refers to an aromatic ring system which includes, but not limited to phenyl, biphenyl, indanyl, 1-naphthyl, 2-naphthyl and terahydronaphthyl.

As used herein, the term "heteroaryl" is intended to mean stable monocyclic and polycyclic hydrocarbons that include at least one aromatic ring and at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl and benzodioxane, benzodioxazolyl, furanyl, dihydrobenzofuranyl, benzofuranyl, benzothiophenyl, pyridinyl, benzothiazolyl, imidazo[1,2-a]pyridinyl, imidazo[1,5-a]pyridinyl, benzo[c][1,2,5]oxadiazolyl, or pyrazolo[1,5-a]pyrimidinyl. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and S(O)$_p$, wherein p is 0, 1 or 2).

"Halo" or "halogen" includes fluoro, chloro, bromo, and iodo.

"Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

The term "heterocycloalkyl" refers to any five to ten membered monocyclic or bicyclic, saturated ring structure containing at least one heteroatom selected from the group consisting of O, N and S. The heterocycloalkyl group may be attached at any heteroatom or carbon atom of the ring such that the result is a stable structure. Examples of suitable heterocycloalkyl groups include, but are not limited to, azepanyl, aziridinyl, azetidinyl, pyrrolidinyl, dioxolanyl, imidazolidinyl, pyrazolidinyl, piperazinyl, piperidinyl, dioxanyl, morpholinyl, dithianyl, thiomorpholinyl, oxazepanyl, oxiranyl, oxetanyl, quinuclidinyl, tetrahyofuranyl, tetrahydropyranyl, piperazinyl, hexahydro-5H-[1,4]dioxino[2,3-c]pyrrolyl, benzo[d][1,3]dioxolyl, and the like.

As referred to herein, the term "substituted" means that at least one hydrogen atom is replaced with a non-hydrogen group, provided that normal valencies are maintained and that the substitution results in a stable compound.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present disclosure can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Allen, Jr., L. V., ed., *Remington: The Science and Practice of Pharmacy,* 22nd Edition, Pharmaceutical Press, London, UK (2012). The disclosure of which is hereby incorporated by reference.

In addition, compounds of formula I and formula II (or sub-formula thereof) may have prodrug forms. Any compound that will be converted in vivo to provide the bioactive agent (i.e., a compound of formula I or II (or sub-formula thereof)) is a prodrug within the scope and spirit of the disclosure. Various forms of prodrugs are well known in the art. For examples of such prodrug derivatives, see:

a) Bundgaard, H., ed., *Design of Prodrugs,* Elsevier (1985), and Widder, K. et al., eds., *Methods in Enzymology,* 112:309-396, Academic Press (1985);
b) Bundgaard, H., Chapter 5: "Design and Application of Prodrugs", *A Textbook of Drug Design and Development,* pp. 113-191, Krogsgaard-Larsen, P. et al., eds., Harwood Academic Publishers (1991);
c) Bundgaard, H., *Adv. Drug Deliv. Rev.,* 8:1-38 (1992);
d) Nielsen, N. M. et al., *J. Pharm. Sci.,* 77:285 (1988);
e) Kakeya, N. et al., *Chem. Pharm. Bull.,* 32:692 (1984); and
g) Rautio, J., ed., *Prodrugs and Targeted Delivery* (*Methods and Principles in Medicinal Chemistry*), Vol. 47, Wiley-VCH (2011).

Compounds containing a carboxy group can form physiologically hydrolyzable esters that serve as prodrugs by being hydrolyzed in the body to yield formula I or formula II compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I or formula II (or sub-formula thereof) include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well-known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice,* The Royal Society of Chemistry, Cambridge, UK (Second Edition, reproduced, 2006); Testa, B. et al., *Hydrolysis in Drug and Prodrug Metabolism. Chemistry, Biochemistry and Enzymology,* VCHA and Wiley-VCH, Zurich, Switzerland (2003); Wermuth, C. G., ed., *The Practice of Medicinal Chemistry,* Third Edition, Academic Press, San Diego, Calif. (2008).

The present disclosure is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the disclosure can generally be prepared by conventional techniques known to those skilled in the art or by processes analogous to those described herein, using an appropriate isotopically-labeled reagent in place of the non-labeled reagent otherwise employed.

The term "solvate" means a physical association of a compound of this disclosure with one or more solvent molecules, whether organic or inorganic. This physical association includes hydrogen bonding. In certain instances the solvate will be capable of isolation, for example, when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

As used herein, the term "patient" refers to organisms to be treated by the methods of the present disclosure. Such organisms preferably include, but are not limited to, mammals (e.g., murines, simians, equines, bovines, porcines, canines, felines, and the like), and most preferably refers to humans.

As used herein, the term "effective amount" means that amount of a drug or pharmaceutical agent, i.e., a compound of the disclosure, that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. An effective amount can be administered in one or more administrations, applications or dosages and is not intended to be limited to a particular formulation or administration route. The term also includes within its scope amounts effective to enhance normal physiological function As used herein, the term "treating" includes any effect, e.g., lessening, reducing, modulating, ameliorating or eliminating, that results in the improvement of the condition, disease, disorder, and the like, or ameliorating a symptom thereof.

For therapeutic use, salts of the compounds of the present disclosure are contemplated as being pharmaceutically acceptable. However, salts of acids and bases that are non-pharmaceutically acceptable may also find use, for example, in the preparation or purification of a pharmaceutically acceptable compound.

Methods of Preparation

The compounds of the present disclosure may be prepared from starting materials which are known in the chemical literature or are commercially available by methods such as those illustrated in the following Schemes utilizing chemical transformations known to those of ordinary skill in the art. Solvents, temperatures, pressures, and other reaction conditions may readily be selected by one of ordinary skill in the art. These Schemes are illustrative and are not meant to limit the possible techniques one skilled in the art may use to manufacture compounds disclosed herein. Different methods may be evident to those skilled in the art. Additionally, the various steps in the synthesis may be performed in an alternate sequence or order to give the desired compound(s). Further, the representation of the reactions in these Schemes as discrete steps does not preclude their being performed in tandem, either by telescoping multiple steps in the same reaction vessel or by performing multiple steps without purifying or characterizing the intermediate(s). In addition, many of the compounds prepared by the methods below can be further modified using conventional chemistry well known to those skilled in the art. All documents cited herein are incorporated herein by reference in their entirety.

Reference can also be made to International Publication Nos. WO2016/073738, WO2016/073770, and WO2016/073774.

References to many of these chemical transformations employed herein can be found in Smith, M. B. et al., *March's Advanced Organic Chemistry Reactions, Mechanisms, and Structure*, Fifth Edition, Wiley-Interscience, New York (2001), or other standard texts on the topic of synthetic organic chemistry. Certain transformations may require that reactive functional groups be masked by protecting group(s). A convenient reference which provides conditions for introduction, removal, and relative susceptibility to reaction conditions of these groups is Greene, T. W. et al., *Protective Groups in Organic Synthesis*, Third Edition, Wiley-Interscience, New York (1999).

Schemes 1-6 depict methods for preparing compounds of formula I and II.

Treatment of a ketone (III) with an electrophilic triflating reagent such as triflic anhydride in the presence of an organic base such as 2,6-di-tert-butyl-4-methyl pyridine can give vinyl triflates of the general structure IV. For ketone III, other cyclic and acyclic ketal protecting groups could be employed in addition to the ethylene glycol-derived ketal shown. Alternatively, ketones of type III can be treated with a strong base just as LiHMDS and the resulting lithium enolate can be treated with N-phenyltrifluoromethanesulfonamide or other electrophilic triflating reagents. The enoltriflate IV undergo Suzuki coupling to an aryl boronic ester, which is well-known to one skilled in the art. In addition to the boronic ester shown, boronic acids and other derivatized boron species have also been employed successfully in Suzuki couplings. Many variations of the Suzuki coupling are known, but generally they involve heating the two coupling partners in the presence of a base such as aq. potassium carbonate in a solvent such as DMF with a catalyst such as Pd(PPh$_3$)$_4$. The olefin resulting from the Suzuki coupling can be reduced under catalytic hydrogenation conditions with for example Pd/C under an atmosphere of hydrogen to afford compounds of general structure V. Acid hydrolysis of the ketal in a compound of general structure V will afford the corresponding ketone which can then be converted to a enoltriflate of general structure VI by methods already described. Conversion of the vinyl triflate VI to vinyl boronic ester VII can be accomplished used standard conditions developed by Miyaura (T. Ishiyama, M. Murata, N. Miyaura, *J. Org. Chem.*, 1995, 60, 7508-7510.)

A boronate of general structure IX can be prepared from an aryl halide of general structure VIII under standard conditions utilizing a Pd catalyst such as Pd(PPh$_3$)$_4$ or 1,1'-bis(diphenylphosphino)ferrocenedichloro palladium(II) and diborane. Rhodium catalyzed 1,4-conjugate addition of the boronic ester IX and an unsaturated ester X are well known (Zou, G. et al., *Dalton Trans.*, 28:3055 (2007)) and can be accomplished using a rhodium$^I$ catalyst, for example, [Rh(COD)Cl]$_2$ in the presence of a strong base such as NaOH to afford saturated esters of the general structure XI. Compounds of general structure XI can be deprotected by methods well known to one skilled in the art, to afford the corresponding phenol. The phenol can be activated by treatment with triflic anhydride in the presence of an organic base such as diisopropylethylamine to afford a compound of general structure XII. Vinyl boronic esters such as VII will participate in Suzuki couplings with a variety of coupling partners including but not limited to aryl and vinyl halides and aryl and vinyl triflates and more specifically a coupling partner such as XII to afford compounds of general structure XIII. Saturated compounds of general structure XIV can be prepared from olefins of general structure XIII by treatment under catalytic hydrogen conditions, such as Pd/C under an atmosphere of hydrogen. Compounds of disclosure (I) can be prepared from XIV by treatment with an isocyanate of general structure XV.

Scheme 1.

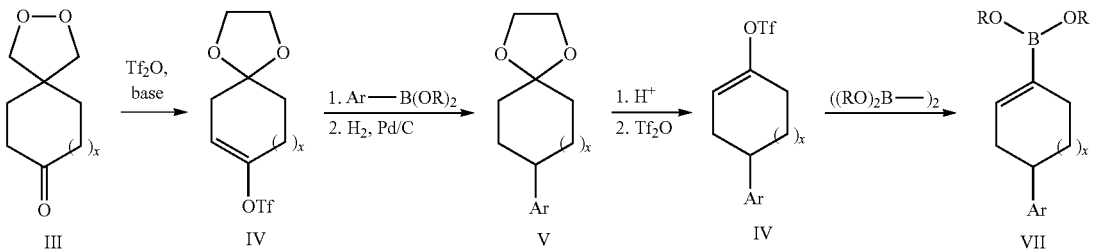

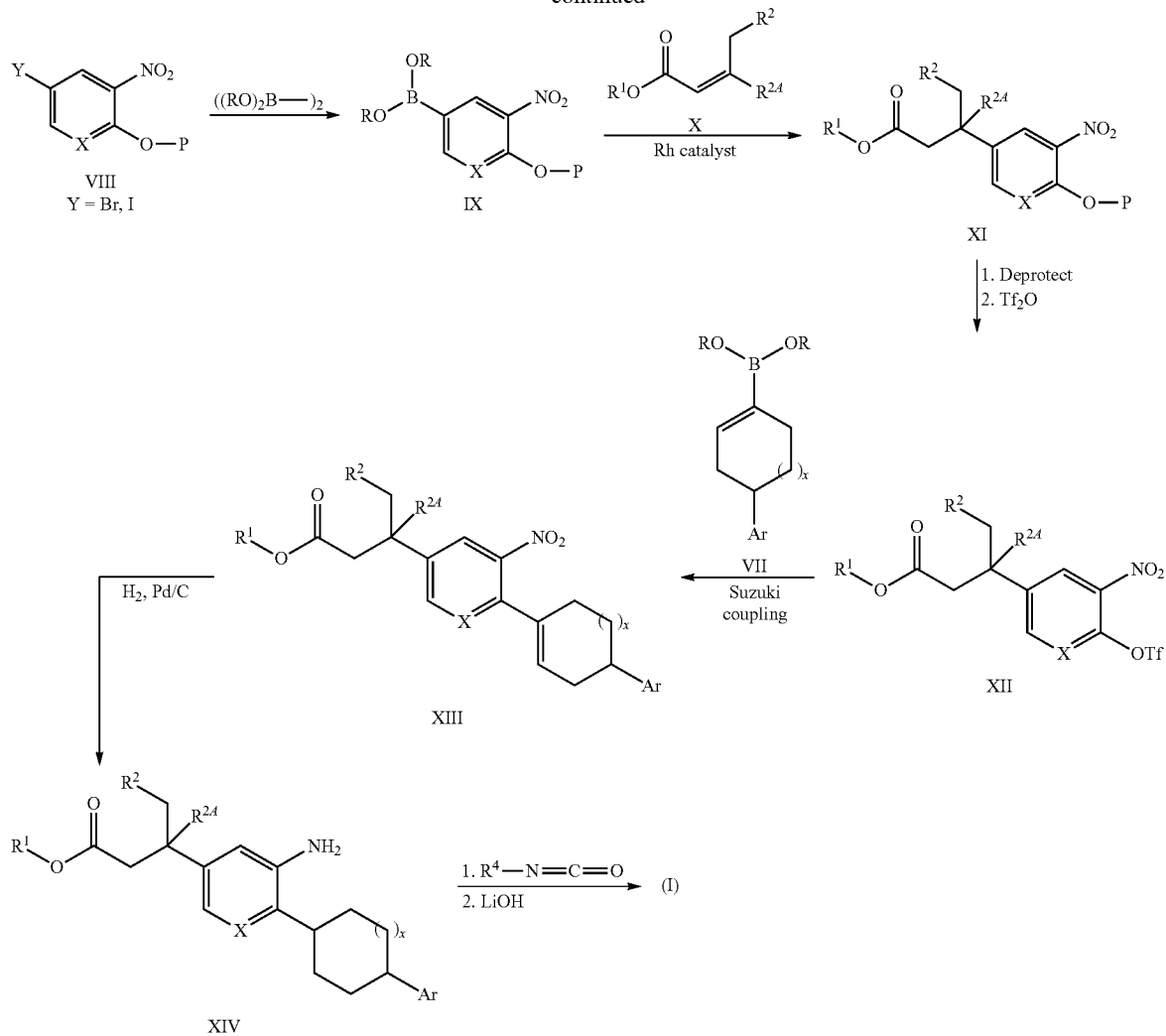

In another embodiment, Amines of general structure XIV can undergo a palladium catalyzed coupling to both aryl and heteroaryl halides XV to afford N-arylated compounds of general structure XVI. Coupling can be accomplished by utilizing conditions established by Buchwald and Hartwig (i.e., Pd$_2$(dba)$_3$, Xantphos and base) that are well-known to one skilled in the art (Surry, D. S. et al., *Chem. Sci.*, 2:27-50 (2011)). Compounds of general structure XVI can be converted to compounds of the disclosure (II) by methods already discussed.

Scheme 2.

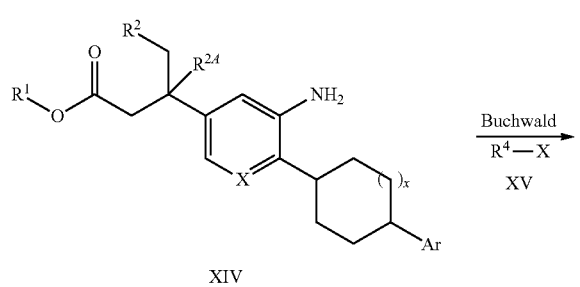

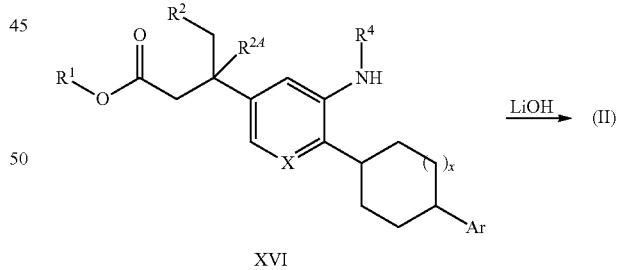

Aryl boronic esters of general structure XVII can be prepared from an aryl triflate of general structure XII by methods described herein. The triflate XVII can under Suzuki coupling with aryl or heteroaryl halides to afford compounds of general structure XVIII. Amines of general structure XIX can be prepared from compounds of general structure XVIII containing a nitro functional group by many methods known to one skilled in the art, for example by treatment with a reducing metal such as zinc in acidic media. Amines of general structure XIX can be converted to compounds of the disclosure (I) and (II) by methods already discussed herein.

Scheme 3.

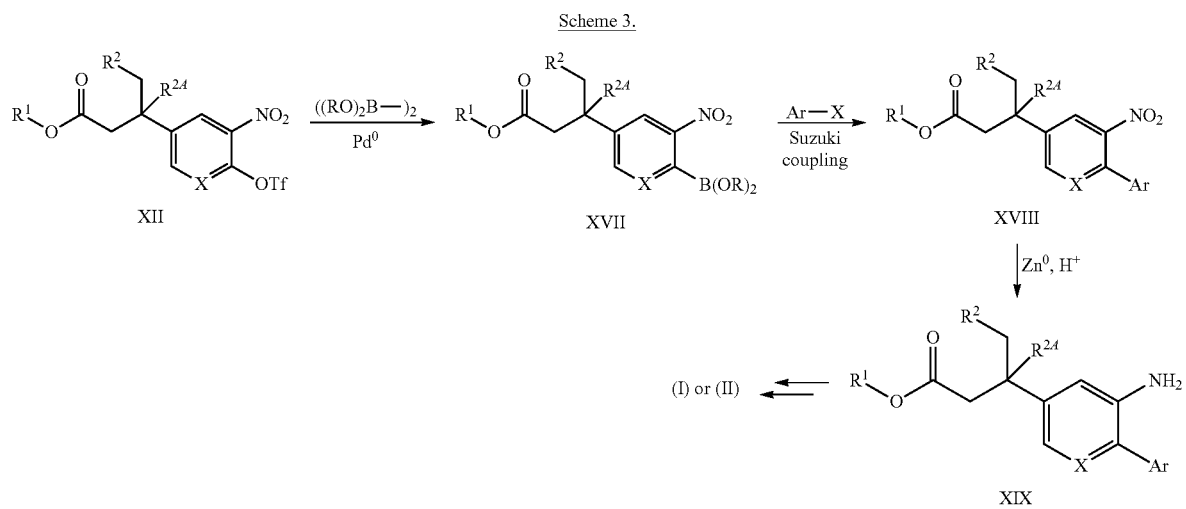

In another embodiment, compounds of general structure XI can be reduced with a metal such as Zinc in acetic media to give the corresponding aniline. A palladium catalyzed coupling, such as a Buchwald coupling as depicted in Scheme 2, of an aryl halide to this newly formed amine will yield a compound of general structure XX. A triflate of general structure XXI can be prepared from XX by initial deprotection of the phenol under conditions well-known to one skilled in the art and triflate formation as described previously. A compound of general structure XXIII can be prepared by Suzuki coupling of a triflate of general structure XXI and a vinylboronic ester of general structure XXII. A saturated amine of general structure XXIV can be prepared from an olefin of general structure XXIII by first treatment under catalytic hydrogenation conditions, such as $H_2$ and Pd/C, and then acidic conditions, such as TFA, to remove the Boc protecting group. Compounds of general structure XXIV can be transformed to compounds of the disclosure (II) by treatment under strongly basic conditions, such as LiOH.

Scheme 4.

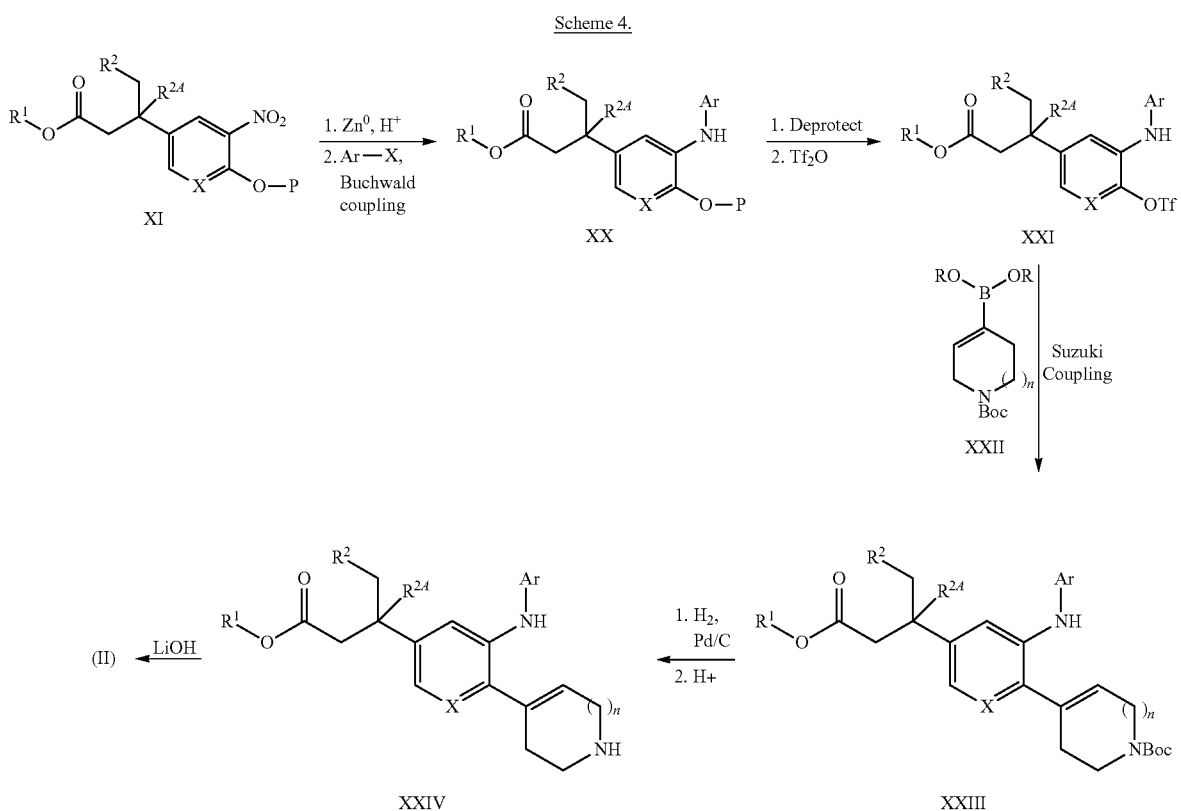

Compounds of general structure XXIV can be further elaborated by conditions well-known to one skilled in the art as shown in Scheme 5 to prepare compounds of the disclosure (II).

Scheme 5.

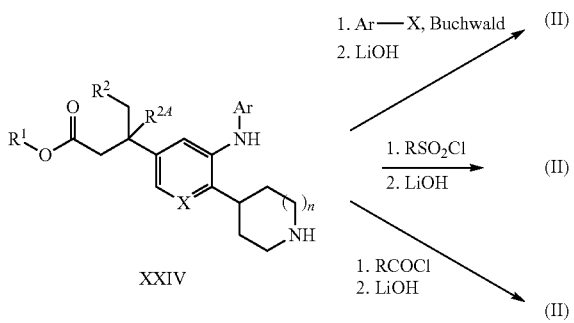

Compounds of general structure XXVI can be prepared from a compound of general structure XI by initial treatment under conditions to reduce the nitro group to an amine, such as Zinc in acetic acid, followed formation of the urea by treatment with an isocyanate XXV. Compounds of general structure XXVI can be converted to a compound of the disclosure (I) by the methods described in previous schemes.

Scheme 6.

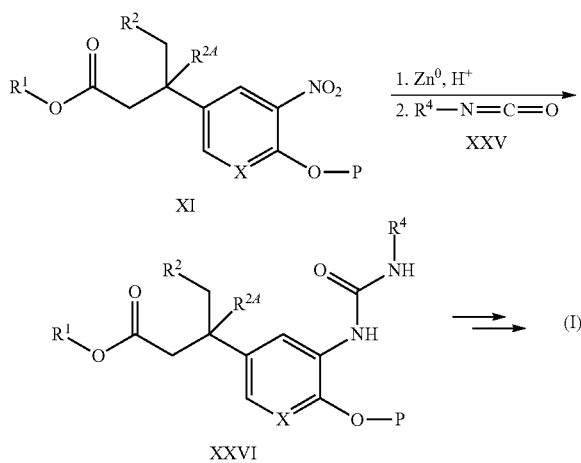

EXAMPLES

The following Examples are put forth so as to provide those of ordinary skill in the art with a complete disclosure and description of how to make and use the present invention, and are not intended to limit the scope of what the inventors regard as their invention, nor are they intended to represent that the experiments below were performed or that they are all of the experiments that may be performed. It is to be understood that exemplary descriptions written in the present tense were not necessarily performed, but rather that the descriptions can be performed to generate data and the like of a nature described therein. Efforts have been made to ensure accuracy with respect to numbers used (e.g., amounts, temperature, etc.), but some experimental errors and deviations should be accounted for.

Unless indicated otherwise, parts are parts by weight, molecular weight is weight average molecular weight, temperature is in degrees Celsius (° C.), and pressure is at or near atmospheric. Standard abbreviations are used, including the following: wt=wildtype; bp=base pair(s); kb=kilobase(s); nt=nucleotides(s); aa=amino acid(s); s or sec=second(s); min=minute(s); h or hr=hour(s); ng=nanogram; μg=microgram; mg=milligram; g=gram; kg=kilogram; dl or dL=deciliter; μl or μL=microliter; ml or mL=milliliter; l or L=liter; μM=micromolar; mM=millimolar; M=molar; kDa=kilodalton; i.m.=intramuscular(ly); i.p.=intraperitoneal(ly); SC or SQ=subcutaneous(ly); QD=daily; BID=twice daily; QW=weekly; QM=monthly; HPLC=high performance liquid chromatography; BW=body weight; U=unit; ns=not statistically significant; PBS=phosphate-buffered saline; IHC=immunohistochemistry; DMEM=Dulbecco's Modification of Eagle's Medium; EDTA=ethylenediaminetetraacetic acid.

Analytical HPLC/MS was performed using the following methods:

Method N: Kinetex XB-C18 (75×3) mm, 2.6 μm; Mobile P Chiralcel hase A: 10 mM NH$_4$OAc in Water:Acetonitrile (98:02); Mobile Phase B: 10 mM NH$_4$OAc in Water:Acetonitrile (02:98); Gradient: 20-100% B over 4 minutes, flow rate 1 mL/min, then a 0.6 minute hold at 100% B flow rate 1.5 mL/min; then Gradient: 100-20% B over 0.1 minutes, flow rate 1.5 mL/min.

Method O: Column: Ascentis Express C18 (50×2.1) mm, 2.7 μm; flow rate 1.1 mL/min; gradient time 3 min; Temperature: 50° C., 0% Solvent B to 100% Solvent B; monitoring at 220 nm (Solvent A: 95% Water: 5% Acetonitrile; 10 mM NH$_4$OAc; Solvent B: 5% Water: 95% Acetonitrile; 10 mM NH$_4$OAc).

Method P: Column: Ascentis Express C18 (50×4.6) mm, 2.7 μm, flow rate 4 mL/min; gradient: 0 to 100% solvent B over 4 min; Temperature: 50° C. Monitoring at 220 nm (Solvent A: 95:05 water:CH$_3$CN with 10 mM NH$_4$OAc and Solvent B: 05:95 water:CH$_3$CN with 10 mM NH$_4$OAc)

Method Q: Column: Ascentis Express C18 (50×4.6) mm, 2.7 μm, flow rate 4 mL/min; gradient: 0 to 100% solvent B over 4 min; Temperature: 50° C.; monitoring at 220 nm (Solvent A: 95:05 water:CH$_3$CN with 0.1% TFA and Solvent B: 05:95 water:CH$_3$CN with 0.1% TFA)

Method R: Column: Ascentis Express C18 (50×2.1) mm, 2.7 μm, flow rate 1.1 mL/min; gradient: 0 to 100% solvent B over 3 min; Temperature: 50° C.; monitoring at 220 nm (Solvent A: 95:05 water:CH$_3$CN with 0.1% TFA and Solvent B: 05:95 water:CH$_3$CN with 0.1% TFA)

Method S: Column: Chiralpak ASH (250×4.6) mm, 5.0 μm; Isocratic Mode, CO$_2$: Co-Solvent (85:15), Co-Solvent: 0.2% DEA in Methanol; Co-Solvent percentage: 15%, Column Temperature: 22.1° C.; Back Pressure: 100 bars; Total Flow: 3 g/min; CO$_2$ flow: 2.55 g/min; Co-Solvent flow: 0.45 g/min.

Method T: Column: Acquity BEH C18 (2.1×50 mm) 1.7 um; Mobile phase A: Buffer:ACN (95:5); Mobile phase B: Buffer:ACN (5:95), Buffer: 5 mM Ammonium Acetate; Gradient: 20-90% B over 1.1 minutes, then a 0.6 minute hold at 90% B, flow rate 0.5 mL/min.

Method U: Column: Kinetex XB-C18 (75×3) mm, 2.6 μm; Mobile Phase A: 10 mM NH$_4$COOH in Water:Acetonitrile (98:02; Mobile Phase B: 10 mM NH$_4$COOH in Water: Acetonitrile (02:98); Gradient: 20-100% B over 4 minutes, flow rate 1 mL/min, then a 0.6 minute hold at 100% B flow rate 1.5 mL/min; then Gradient: 100-20% B over 0.1 minutes, flow rate 1.5 mL/min.

Method V: Column: Chiralpak ASH (250×4.6) mm, 5.0 µm; Isocratic Mode, Co-Solvent: 0.2% DEA in Methanol; Co-Solvent percentage: 20%, Column Temperature: 20.2° C.; Back Pressure: 100 bars; Total Flow: 3 g/min; $CO_2$ flow: 2.4 g/min; Co-Solvent flow: 0.6 g/min.

Method W: Column: Chiralpak ASH (250×4.6) mm, 5.0 µm; Isocratic Mode, Co-Solvent: 0.2% DEA in Methanol; Co-Solvent percentage: 30%, Column Temperature: 20.2° C.; Back Pressure: 100 bars; Total Flow: 3 g/min; $CO_2$ flow: 2.1 g/min; Co-Solvent flow: 0.9 g/min.

Method X: Column: Chiralpak ASH (250×4.6) mm, 5.0 µm; Isocratic Mode, Co-Solvent: 0.2% DEA in Methanol; Co-Solvent percentage: 25%, Column Temperature: 24.3° C.; Back Pressure: 100 bars; Total Flow: 3 g/min; $CO_2$ flow: 2.5 g/min; Co-Solvent flow: 0.75 g/min.

Method Y: Column: Chiralpak ASH (250×4.6) mm, 5.0 µm; Isocratic Mode, Co-Solvent: 0.2% DEA in Methanol; Co-Solvent percentage: 25%, Column Temperature: 27.1° C.; Back Pressure: 100 bars; Total Flow: 3 g/min; $CO_2$ flow: 2.25 g/min; Co-Solvent flow: 0.75 g/min.

Method Z: Column: Chiralcel-OJH (250×4.6) mm, 5.0 µm; Isocratic Mode, Co-Solvent: 0.2% DEA in Methanol; Co-Solvent percentage: 30%, Column Temperature: 26° C.; Back Pressure: 100 bars; Total Flow: 3 g/min; $CO_2$ flow: 2.1 g/min; Co-Solvent flow: 0.9 g/min.

Method AA: Column: Acquity BEH C18 (2.1×50 mm) 1.7 um; Mobile phase A: 0.1% TFA in water; Mobile phase B: Acetonitrile; Gradient: 2-98% B over 1 minutes, then a 0.6 minute hold at 98% B.

Method AB: Column: Lux Cellulose-4 (250×4.6) mm, 5.0 µm; Isocratic Mode, Co-Solvent: 0.2% DEA in Methanol; Co-Solvent percentage: 30%, Column Temperature: 24.2° C.; Back Pressure: 100 bars; Total Flow: 3 g/min; $CO_2$ flow: 2.1 g/min; Co-Solvent flow: 0.9 g/min.

Method AC: Column: Chiralcel-ASH (250×4.6) mm, 5.0 µm; Isocratic Mode, Co-Solvent: 0.2% DEA in Methanol; Co-Solvent percentage: 30%, Column Temperature: 26° C.; Back Pressure: 100 bars; Total Flow: 3 g/min; $CO_2$ flow: 2.1 g/min; Co-Solvent flow: 0.9 g/min Method AD: Kinetex XB-C18 (75×3) mm, 2.6 µm; Mobile Phase A: 0.1% HCOOH in Water: Mobile Phase B: 100% Acetonitrile Gradient: 20-100% B over 4 minutes, flow rate 1 mL/min, then a 0.6 minute hold at 100% B flow rate 1.5 mL/min; flow rate 1.5 mL/min.

Method AE: Column: HP-5MS (Part Number: Agilent 19091S-433); (250×30) mm; 0.25 µm; Injection volume 3 µl, runtime 17 min (GCMS).

Method AF: Column: Chiralpak AD-H (250×4.6) mm, 5.0 µm; Isocratic Mode, Co-Solvent: 0.25% DEA in Methanol; Co-Solvent percentage: 30%, Column Temperature: 25° C.; Back Pressure: 100 bars; Total Flow: 3 g/min; $CO_2$ flow: 2.1 g/min; Co-Solvent flow: 0.9 g/min.

Method AG: Column: Chiralcel-ASH (250×2.1) mm, 5.0 µm; Isocratic Mode, Co-Solvent: 0.25% DEA in Methanol; Co-Solvent percentage: 45%, Column Temperature: 25° C.; Back Pressure: 100 bars; Total Flow: 75 g/min.

Method AH: Column: Chiralcel-ASH (250×4.6) mm, 5.0 µm; Isocratic Mode, Co-Solvent: 0.2% DEA in Methanol; Co-Solvent percentage: 40%, Column Temperature: 25° C.; Back Pressure: 100 bars; Total Flow: 4 g/min.

Method AI: Column: Chiralcel-ASH (250×4.6) mm, 5.0 µm; Isocratic Mode, Co-Solvent: 0.2% DEA in Methanol; Co-Solvent percentage: 30%, Column Temperature: 24.7° C.; Back Pressure: 95 bars; Total Flow: 4 g/min; $CO_2$ flow: 2.4 g/min; Co-Solvent flow: 1.6 g/min.

Method AJ: Column: Chiralpak AD-H (250×30) mm, 5.0 µm; Isocratic Mode, Co-Solvent: 0.25% DEA in Methanol; Co-Solvent percentage: 30%, Column Temperature: 25° C.; Back Pressure: 100 bars; Total Flow: 120 g/min Method AK: Column: Chiralpak AD-H (250×4.6) mm, 5.0 µm; Isocratic Mode, Co-Solvent: 0.25% DEA in Methanol; Co-Solvent percentage: 40%, Column Temperature: 25° C.; Back Pressure: 100 bars; Total Flow: 4 g/min; $CO_2$ flow: 2.4 g/min; Co-Solvent flow: 1.6 g/min.

Method AM: Column: Chiralpak IA (250×4.6) mm, 5.0 µm; Isocratic Mode, Co-Solvent: 0.2% DEA in Methanol; Co-Solvent percentage: 30%, Column Temperature: 21° C.; Back Pressure: 100 bars; Total Flow: 3 g/min; $CO_2$ flow: 2.1 g/min; Co-Solvent flow: 0.9 g/min.

Method AN: Column: Chiralpak IA (250×4.6) mm, 5.0 µm; Isocratic Mode, Co-Solvent: 0.2% DEA in Methanol; Co-Solvent percentage: 20%, Column Temperature: 21° C.; Back Pressure: 100 bars; Total Flow: 3 g/min; $CO_2$ flow: 2.4 g/min; Co-Solvent flow: 0.6 g/min.

Method AU: Column: Xbridge C18 (50×3.0) mm, 1.7 µm; flow rate 1.0 mL/min; gradient time 0 min 0% Solvent B to 2 min 100% Solvent B, then a 1.0 minute hold at 100% B, monitoring at 220 nm (Solvent A: 10 mM 98% Ammonium formate, 2% Acetonitrile; Solvent B: 10 mM 2% Ammonium formate, 98% Acetonitrile).

Method AV: Column: Acquity BEH C8 (2.1×50 mm) 1.7 um; Mobile phase A: Buffer:ACN (95:5); Mobile phase B: Buffer:ACN (5:95), Buffer: 5 mM Ammonium Acetate; Gradient: 20-90% B over 1.1 minutes, then a 0.6 minute hold at 90% B, flow rate 0.5 mL/min.

Method AQ: Column: Chiralpak OD-H (250×4.6) mm, 5.0 µm, Co-Solvent: 0.2% DEA in Methanol; Co-Solvent percentage: 40%, Column Temperature: 30° C.; Back Pressure: 100 bars; Total Flow: 3 g/min;

Method AR: Column: Lux Cellulose-2 (250×4.6) mm, 5.0 µm; Isocratic Mode, Co-Solvent: 0.2% DEA in Methanol; Co-Solvent percentage: 10%, Column Temperature: 30° C.; Back Pressure: 100 bars; Total Flow: 3 g/min.

Method AS: Column: Whelk-01(R,R) (4.6×250) mm, 5 u; Co-Solvent: 0.2% DEA in IPA; Co-Solvent percentage: 15%, Column Temperature: 20.6° C.; Back Pressure: 100 bars; Total Flow: 3 g/min.

Method AT: Column: Acentis Express C18 (50×2.1) mm, 1.7 µm; flow rate 1.0 mL/min; gradient time 0 min 20% Solvent B to 4 min 100% Solvent B, then a 0.6 minute hold at 100% B, monitoring at 220 nm (Solvent A: 10 mM 98% Ammonium formate, 2% Acetonitrile; Solvent B: 10 mM 2% Ammonium formate, 98% Acetonitrile).

Method AU: Column: Waters XBridge C18, 19×150 mm, 5-µm particles; Mobile Phase A: 10-mM ammonium acetate; Mobile Phase B: acetonitrile; gradient: 5-45% B over 25 minutes, then a 5-minute hold at 100% B; Flow: 15 mL/min.

Method AV: Column: Lux Cellulose-2 (250×4.6) mm, 5.0 µm; Isocratic Mode, Co-Solvent: 25% (0.2% DEA in Methanol; Co-Solvent percentage: 75%, Column Temperature: 30° C.; Back Pressure: 100 bars; Total Flow: 3 g/min; $CO_2$ flow: 2.1 g/min; Co-Solvent flow: 0.9 g/min.

Method AW: Column: YMC Amylose SA (250×4.6) mm, 5.0 µm; Isocratic Mode, Co-Solvent: (0.2% DEA in Ethanol; Co-Solvent percentage: 20%, Column Temperature: 30° C.; Back Pressure: 100 bars; Total Flow: 3 g/min; $CO_2$ flow: 2.1 g/min; Co-Solvent flow: 0.9 g/min.

Method AX: Column: Chiralpak IC (250×4.6) mm, 5.0 µm; Isocratic Mode, Co-Solvent: 0.25% DEA in Ethanol; Co-Solvent percentage: 30%, Column Temperature: 30° C.; Back Pressure: 100 bars; Total Flow: 3 g/min; $CO_2$ flow: 2.1 g/min; Co-Solvent flow: 0.9 g/min.

Method AY: Column: Acquity BEH C18 (3.0×50 mm) 1.7 um; Mobile phase A: Buffer:ACN (95:5); Mobile phase B:

Buffer:ACN (5:95), Buffer: 5 mM Ammonium Acetate; Gradient: 20-90% B over 1.1 minutes, then 1.7 minute hold at 90% B, flow rate 0.7 mL/min.

Method AZ: Column: Chiralpak AD-H (250×30) mm, 5.0 μm; Isocratic Mode, Co-Solvent: 0.2% DEA in Methanol; Co-Solvent percentage: 30%, Column Temperature: 25° C.; Back Pressure: 100 bars; Total Flow: 120 g/min.

Method BA: Column: Acquity UPLC BEH C18 (3×50 mm) 1.7 um; Mobile phase A: Buffer:ACN (95:5); Mobile phase B: Buffer:ACN (5:95), Buffer: 5 mM Ammonium Acetate; Gradient: 20-90% B over 1.1 minutes, then a 0.6 minute hold at 90% B, flow rate 0.7 mL/min.

Method BB: Column: ZORBAX SBC18 (4.6×50) mm, 5 μm; Mobile Phase A: 10 mM $NH_4COOH$ in Water:Acetonitrile (98:02; Mobile Phase B: 10 mM $NH_4COOH$ in Water: Acetonitrile (02:98); Gradient: 0-100% B over 4 minutes, flow rate 1.5 mL/min, then a 0.6 minute hold at 100% B flow rate 1.5 mL/min; then Gradient: 100-30% B over 0.1 minutes, flow rate 1.5 mL/min.

Method BC: Column: Acquity BEH C18 (2.1×50 mm) 1.7 um; Mobile phase A: 0.1% TFA in water; Mobile phase B: 0.1% TFA in Acetonitrile; Gradient: 10-90% B over 1.0 minutes, then a 0.6 minute hold at 90% B, flow rate 0.7 mL/min.

Method BD: Column-Kinetex SBC18 (4.6×50 mm-5 μm), M.phase A: 10 mM NH4C00H IN WATER:ACN (98:02), M.phase B: 10 mM $NH_4C00H$ IN WATER:ACN (02:98), Buffer: 10 mM Ammonium Acetate; Gradient: 30-100% B over 4.0 minutes, then a 0.6 minute hold at 100% B, flow rate 1.5 mL/min Method BE: Gemini-Kinetex nx-C18 (4.6×50 mm-5 μm), M.phase A: 10 mM $NH_4C00H$ IN WATER:ACN (98:02), M.phase B: 10 mM $NH_4C00H$ IN WATER:ACN (02:98), Buffer: 10 mM Ammonium Acetate; Gradient: 30-100% B over 4.0 minutes, then a 0.6 minute hold at 100% B, flow rate 1.5 mL/min.

Method BF: Column: Chiralcel-OJH (250×4.6) mm, 5.0 μm; Co-Solvent: 0.2% DEA in Methanol; Co-Solvent percentage: 20%, Column Temperature: 30° C.; Back Pressure: 100 bars; Total Flow: 3 g/min.

Method BG: Column: Whelk-01(R,R) (4.6×250) mm, 5 u; Co-Solvent: 0.2% DEA in Ethanol; Co-Solvent percentage: 5%, Column Temperature: 22.2° C.; Back Pressure: 100 bars; Total Flow: 3 g/min Method BH: Column: Chiralpak AD-H (250×4.6) mm, 5.0 μm; Co-Solvent: 0.2% DEA in IPA; Co-Solvent percentage: 15%, Column Temperature: 30° C.; Back Pressure: 100 bars; Total Flow: 3 g/min.

Method BI: Column: Chiralpak AD-H (250×3.0) mm, 5.0 μm; Isocratic Mode, Co-Solvent: 0.2% DEA in Methanol; Co-Solvent percentage: 30%, Column Temperature: 25° C.; Back Pressure: 100 bars.

Method BJ: Column: Chiralpak AD-H (250×4.6) mm, 5.0 μm; Co-Solvent: 0.2% DEA in Methanol+IPA (1:1); Co-Solvent percentage: 10%, Column Temperature: 30° C.; Back Pressure: 100 bars; Total Flow: 3 g/min.

Method BK: Column: Chiralpak AD-H (250×4.6) mm, 5.0 μm; Co-Solvent: 0.2% DEA in Methanol; Co-Solvent percentage: 10%, Column Temperature: 30° C.; Back Pressure: 100 bars; Total Flow: 3 g/min.

Method BL: Column: Chiralpak OD-H (250×2.1) mm, 5.0 μm, Co-Solvent: 0.2% DEA in IPA; Co-Solvent percentage: 15%, Column Temperature: 30° C.

Method BM: Column: Chiralpak AD-H (250×4.6) mm, 5.0 μm; Co-Solvent: 0.2% DEA in Methanol; Co-Solvent percentage: 25%, Column Temperature: 30° C.; Back Pressure: 100 bars; Total Flow: 3 g/min Method BN: Column: Chiralpak AD-H (250×4.6) mm, 5.0 μm; Co-Solvent: 0.1% $NH_4OH$ in IPA; Co-Solvent percentage: 10%, Column Temperature: 30° C.; Back Pressure: 100 bars; Total Flow: 3 g/min.

Method BO: Column-Ascentis Express C18 (50×2.1 mm) 2.7 μm, M.phase A: 10 mM $NH_4C00H$ IN WATER:ACN (98:02), M.phase B: 10 mM $NH_4C00H$ IN WATER:ACN (02:98); Gradient: 0-100% B over 1.5 minutes, then a 1.7 minute hold at 100% B, flow rate 1.0 mL/min Method BP: Column: Whelk-01(R,R) (4.6×250) mm, 5 u; Co-Solvent: 0.2% DEA in IPA; Co-Solvent percentage: 10%, Column Temperature: 30° C.; Back Pressure: 100 bars; Total Flow: 3 g/min.

Method BQ: Column: Chiralpak IC (250×4.6) mm, 5.0 μm; Isocratic Mode, Co-Solvent: 0.2% DEA in Mehanol:IPA (1:1); Co-Solvent percentage: 10%, Column Temperature: 30° C.; Back Pressure: 100 bars; Total Flow: 3 g/min.

Method BR: Column: Chiralpak OJ-H (250×4.6 mm), 5 micron; MOBILE PHASE: 0.2% TEA in n-Hexane:EtOH (70:30), FLOW: 1.0 mL\min.

Method BS: Column: Chiralcel-OJH (250×4.6) mm, 5.0 μm; Co-Solvent: 0.2% DEA in Methanol; Co-Solvent percentage: 25%, Column Temperature: 28° C.; Back Pressure: 100 bars; Total Flow: 3 g/min.

Method BT: Column: Chiralcel-OJH (250×4.6) mm, 5.0 μm; Co-Solvent: 0.2% DEA in Methanol; Co-Solvent percentage: 15%, Column Temperature: 30° C.; Back Pressure: 100 bars; Total Flow: 60 g/min.

Method BU: Column: Chiralpak AD-H (250×4.6) mm, 5.0 μm; Isocratic Mode, Co-Solvent: 0.2% DEA in IPA+ACN; Co-Solvent percentage: 10%, Column Temperature: 25° C.; Back Pressure: 100 bars; Total Flow: 3 g/min.

Method BV: Column: lux amylose 2 (250×21.2) mm, Mobile Phase A: 0.2% DEA in Hexane; Mobile Phase B: EtOH; Flow: 25 mL/min.

Method BW: Column: Lux Cellulose-2 (250×4.6) mm, 5.0 μm; Isocratic Mode, Co-Solvent: 25% (0.1% $NH_4OH$ in Methanol); Co-Solvent percentage: 75%, Column Temperature: 30° C.; Back Pressure: 100 bars; Total Flow: 3 g/min;

Method BX: Column: Lux Cellulose-2 (250×4.6) mm, 5.0 μm; Isocratic Mode, Co-Solvent: 0.2% DEA in Ethanol; Co-Solvent percentage: 20%, Column Temperature: 30° C.; Back Pressure: 100 bars; Total Flow: 3 g/min.

Method BY: Column: Chiralpak AD-H (250×4.6) mm, 5.0 μm; Isocratic Mode, Co-Solvent: 0.2% DEA in Ethanol; Co-Solvent percentage: 25%, Column Temperature: 25.7° C.; Back Pressure: 100 bars; $CO_2$ flow rate: 2.25 g/min; Co solvent flow rate: 0.75 g/min; Total Flow: 3 g/min.

Method BZ: Column: Chiralcel-OJH (250×4.6) mm, 5.0 μm; Co-Solvent: 0.2% DEA in Methanol; Co-Solvent percentage: 10%, Column Temperature: 30° C.; Back Pressure: 100 bars; Total Flow: 3 mL/min.

Method CA: Column: YMC Amylose SA (250×4.6) mm, 5.0 μm; Isocratic Mode, Co-Solvent: 0.2% DEA in IPA; Co-Solvent percentage: 15%, Column Temperature: 35° C.; Back Pressure: 100 bars; Total Flow: 60.0 g/min Method CB: Column: Chiralpak ASH (250×4.6) mm, 5.0 μm; Isocratic Mode, Co-Solvent: 0.2% DEA in Hexane: IPA (98:02); Total Flow: 1.0 mL/min.

Method CC: Column: Lux Cellulose-4 (250×4.6) mm, 5.0 μm; Isocratic Mode, Co-Solvent: 30% (0.1% $NH_4OH$ in Methanol); Co-Solvent percentage: 30%, Column Temperature: 30° C.; Back Pressure: 100 bars; Total Flow: 60 g/min.

Method CD: Column: Chiralcel-OJH (250×4.6) mm, 5.0 μm; Co-Solvent: 0.2% DEA in Methanol; Co-Solvent percentage: 30%, Column Temperature: 30° C.; Back Pressure: 100 bars; Total Flow: 3 mL/min.

Method CE: Column: Chiralcel-OJH (250×2.1) mm, 5.0 μm; Co-Solvent: 0.2% DEA in Methanol; Co-Solvent percentage: 20%, Column Temperature: 30° C.; Back Pressure: 100 bars; Total Flow: 60 mL/min.

Method CF: Column: Chiralcel-OJH (250×4.6) mm, 5.0 μm; Co-Solvent: 0.2% DEA in IPA:ACN (1:1); Co-Solvent percentage: 20%, Column Temperature: 30° C.; Back Pressure: 100 bars; Total Flow: 3 mL/min.

Method CG: Column: Chiralpak IC (250×3.0) mm, 5.0 μm; Co-Solvent: 0.2% DEA in Methanol: IPA (1:1); Co-Solvent percentage: 10%, Column Temperature: 30° C.; Back Pressure: 100 bars; Total Flow: 110 g/min.

Method CH: Column: lux amylose 2 (250×4.6) mm, 5.0 μm; Mobile Phase A: 0.2% DEA in Hexane; Mobile Phase B: EtOH; Flow: 1 mL/min.

Method CI: Column-KINETICSX 2.6 u EVO c18 100 Au. M.phase A; 5 mM NH4C0AC IN WATER:ACN (95:05), M.phase B: 5 mM NH4C0AC IN WATER:ACN (05:95), Buffer: 5 mM Ammonium Acetate; flow rate 0.7 mL/min Method CJ: Column: Chiralcel-OJH (250×4.6) mm, 5.0 μm; Co-Solvent: 0.2% DEA in n-Hexane:EtOH (98:2 Total Flow: 1 mL/min.

Method CK: Column: Lux Cellulose-4 (250×4.6) mm, 5.0 μm; Isocratic Mode, Co-Solvent: 0.2% DEA in IPA; Co-Solvent percentage: 15%, Column Temperature: 30° C.; Back Pressure: 100 bars; Total Flow: 3 g/min.

Method CL: Column: Chiralpak AD-H (250×4.6) mm, 5.0 μm; Isocratic Mode, Co-Solvent: 0.2% DEA in Methanol; Co-Solvent percentage: 30%, Column Temperature: 30° C.; Back Pressure: 100 bars; Total Flow: 4 g/min.

Method CM: Column: Chiralpak AD-H (250×4.6) mm, 5.0 μm; Co-Solvent: 0.2% DEA in IPA; Co-Solvent percentage: 30%, Column Temperature: 30° C.; Back Pressure: 100 bars; Total Flow: 4 g/min.

Method CN: Column: Chiralpak IC (250×4.6) mm, 5.0 μm; Isocratic Mode, Co-Solvent: 0.2% DEA in Mehanol: ACN (1:1); Co-Solvent percentage: 25%, Column Temperature: 30° C.; Back Pressure: 100 bars; Total Flow: 3 g/min.

Method CO: Column: Lux Cellulose-4 (250×4.6) mm, 5.0 μm; Co-Solvent: 0.2% DEA in Methanol; Co-Solvent percentage: 10%, Column Temperature: 30° C.; Back Pressure: 100 bars; Total Flow: 3 g/min.

Method CP: Column: ZORBAX AQ (4.6×50) mm, 5 μm; Mobile Phase A: 10 mM NH$_4$COOH in Water:Acetonitrile (98:02; Mobile Phase B: 10 mM NH$_4$COOH in Water:Acetonitrile (02:98); Gradient: 30-100% B over 4 minutes, flow rate 1.5 mL/min, then a 0.6 minute hold at 100% B flow rate 1.5 mL/min; then Gradient: 100-30% B over 0.1 minutes, flow rate 1.5 mL/min.

Method CQ: Column: Gemini nx-C18 (50×4.6) mm, 5 μm; Mobile Phase A: 10 mM NH$_4$COOH in Water:Acetonitrile (98:02; Mobile Phase B: 10 mM NH$_4$COOH in Water:Acetonitrile (02:98); Gradient: 30-100% B over 4 minutes, flow rate 1.5 mL/min, then a 0.6 minute hold at 100% B flow rate 1.5 mL/min; then Gradient: 100-30% B over 0.1 minutes, flow rate 1.5 mL/min.

Method CR: Column: Chiralpak AD-H (250×4.6) mm, 5.0 μm; Co-Solvent: 0.2% DEA in Methanol; Co-Solvent percentage: 20%, Column Temperature: 30° C.; Back Pressure: 100 bars; Total Flow: 3 g/min.

Method CS: Column: Xbridge C18 (50×4.6) mm, 5 μm, flow rate 4.0 mL/min; gradient: 0 to 100% solvent B over 3 min; Temperature: 35° C.; monitoring at 220 nm (Solvent A: 95:05 water:CH$_3$CN with 0.1% TFA and Solvent B: 05:95 water:CH$_3$CN with 0.1% TFA)

Method CT: Column: Chiralpak IA (250×4.6) mm, 5.0 μm; Co-Solvent: 0.2% DEA in Methanol; Co-Solvent percentage: 15%, Column Temperature: 21.7° C.; Back Pressure: 96 bars; Total Flow: 3 g/min; CO$_2$ flow: 2.55 g/min; Co-Solvent flow: 0.45 g/min.

Method CU: Column: Chiralpak ASH (250×4.6) mm, 5.0 μm; Co-Solvent: 0.2% DEA in IPA; Co-Solvent percentage: 20%, Column Temperature: 30° C.; Back Pressure: 100 bars; Total Flow: 3 mL/min.

Method CV: Column: Lux Cellulose-4 (250×4.6) mm, 5.0 μm; Co-Solvent: 0.2% DEA in IPA: Methanol, (1:1); Co-Solvent percentage: 10%, Column Temperature: 30° C.; Back Pressure: 100 bars; Total Flow: 3 g/min.

Method CW: Column: Chiralpak AD-H (250×30) mm, 5.0 μm; Isocratic Mode, Co-Solvent: 0.2% DEA in Methanol; Co-Solvent percentage: 30%, Column Temperature: 21.6° C.; Back Pressure: 104 bars; Total Flow: 3 g/min. CO2 flow rate: 2.1; Co solvent flow rate: 0.9

Method CX: Column: Lux Amylose-2 (250×4.6) mm, 5.0 μm; Isocratic Mode, Co-Solvent: 15% (0.2% DEA in IPA; Column Temperature: 30° C.; Back Pressure: 101 bars; Total Flow: 3 g/min; CO$_2$ flow: 2.55 g/min; Co-Solvent flow: 0.45 g/min.

Method CY: Column: Lux Cellulose-4 (250×4.6) mm, 5.0 μm; Mobile Phase: 0.2% TFA in n-Hexane: Methanol: Ethanol (97:03), flow rate 1.0 mL/min.

Method CZ: Column: Xbridge C18 (50×4.6) mm, 5.0 μm; Mobile Phase A: 0.1% TFA in Water; Mobile Phase B: Acetonitrile; Gradient: 5-95% B over 4 minutes, Temp: 35° C.; Flow Rate: 4.0 mL/min.

Method DA: Column: R,R-WHELK (250×4.6) mm, 5 μm, MOBILE PHASE: 0.2% EA in n-Hexane: IPA (99:01), FLOW: 1.0 mL/min Method DB: Column Lux Cellulose-4 (4.6×250) mm, 5 um, Co-Solvent 0.2% DEA in Methanol, Column Temperature 19.4° C., CO2 Flow Rate 1.8 g/min, Co-Solvent Flow Rate 1.2 g/min, Co-Solvent 40%, Total Flow 3 g/min, Back Pressure 104 bars.

Method DC: Column: Xbridge C18 (50×4.6) mm, 5 μm, Solvent A: 10 mM NH4OAC, Solvent B: Acetonitrile, Temp: 35° C., Gradient: 5-95% B over 4 minutes, Flow Rate: 4.0 ml/min.

Method DD: Column CHIRALPAK ADH (250×4.6) mm, 5 um, Co-Solvent 0.2% DEA in Methanol, Column Temperature 19.5° C., CO$_2$ Flow Rate 2.25 g/min, Co-Solvent Flow Rate 0.75 g/min, Co-Solvent 25%; Total Flow 3 g/min; Back Pressure 100 bars.

Method DE: Column Chiralpak AD-H (250×4.6) mm, 5 um, Column Temperature 27° C., Co-Solvent 0.2% DEA in Methanol, CO$_2$ Flow Rate 2.25 g/min, Co-Solvent Flow Rate 0.75 g/min, Co-Solvent 25%, Total Flow 3 g/min, Back Pressure 98 bars.

Method DF: Column Chiralpak IA (250×4.6) mm, 5 u, Co-Solvent 0.1% NH4OH IN IPA, Column Temperature 19.3° C., CO$_2$ Flow Rate 1.8 g/min, Co-Solvent Flow Rate 1.2 g/min, Co-Solvent 40%, Total Flow 3 g/min, Back Pressure 100 bars.

Method DG: Column: Chiralpak AD-H (250×4.6) mm, 5 um, Co-Solvent; 0.2% DEA in IPA, Column Temperature: 15.3° C., CO$_2$ Flow Rate: 2.4 g/min, Co-Solvent Flow Rate: 3 g/min, Co-Solvent: 99%, Back Pressure 100 bars.

Method DH: Column: Chiralpak AD-H (250×4.6) mm, 5 um, Co-Solvent: 0.2% DEA in IPA, Column Temperature: 27.7° C., CO$_2$ Flow Rate: 2.4 g/min, Co-Solvent Flow Rate: 0.6 g/min, Co-Solvent: 20%, Total Flow; 3 g/min, Back Pressure; 100 bars.

Method DI: Column: Chiralpak AD-H (250×4.6) mm, 5 um, Co-Solvent: 0.1% NH$_{40}$H IN IPA, Column Temperature: 21.4° C., CO$_2$ Flow Rate: 2.25 g/min, Co-Solvent Flow Rate: 0.75 g/min, Co-Solvent: 25%, Total Flow: 3 g/min, Back Pressure: 102 bars.

Method DJ: Column: Chiralpak AD-H (250×4.6) mm, 5 um, Co-Solvent: IPA, Column Temperature: 20.6° C., CO$_2$ Flow Rate: 2.7 g/min, Co-Solvent Flow Rate: 0.3 g/min, Co-Solvent: 10%, Total Flow: 3, Back Pressure: 100

Method DK: Column: CHIRALPAK-IA (250×4.6), 5 um, MOBILE PHASE: 0.2% DEA in n-Hexane:EtOH (60:40), FLOW: 1.0 ml/min.

Method DL: Column: Chiralpak AD-H (250×4.6) mm, 5.0 μm; Isocratic Mode, Co-Solvent: 0.2% DEA in IPA+ACN; Co-Solvent percentage: 10%, Column Temperature: 30° C.; Back Pressure: 100 bars; Total Flow: 3 g/min.

Method DM: Column: Xbridge BEH C$_8$ (2.1×50 mm) 2.5 um; Mobile phase A: Buffer:ACN (95:5); Mobile phase B: Buffer:ACN (5:95), Buffer: 5 mM Ammonium Acetate; Gradient: 20-90% B over 1.1 minutes, then a 1.7 minute hold at 90% B, flow rate 0.5 mL/min.

Method DN: Column: Chiralcel-OJH (250×4.6) mm, 5.0 μm; Isocratic Mode, Co-Solvent: 0.2% DEA in Ethanol; Co-Solvent percentage: 10%, Column Temperature: 25.8° C.; Back Pressure: 100 bars; Total Flow: 3 g/min; CO$_2$ flow: 2.7 g/min; Co-Solvent flow: 0.3 g/min.

Method DO: Column: Acquity BEH C18 (2.1×50 mm) 1.7 um; Mobile phase A: Buffer:ACN (95:5); Mobile phase B: Buffer:ACN (5:95), Buffer: 5 mM Ammonium Acetate; Gradient: 20-90% B over 1.1 minutes, then a 0.6 minute hold at 90% B, flow rate 0.7 mL/min.

Method DP: Column: Chiralcel OD-H (250×4.6) mm, 5 μm; Co-Solvent: 0.2% DEA in MeOH; CO$_2$ Flow Rate: 2.4 g/min; Co-Solvent Flow Rate: 0.6; Co-Solvent 20%; Total Flow: 3; Back Pressure: 100

Method DQ: Column: Chiralcel IE (250×4.6) mm, 5 μm; Mobile Phase: 0.2% DEA in Hexane:Ethanol:Methanol (1:1) (95:05) Flow: 1.0 ml/min Method DR: Kinetex C18 (75×3) mm, 2.6 μm; Mobile Phase A: 10 mM NH$_4$OAc in Water:Acetonitrile (98:02); Mobile Phase B: 10 mM NH$_4$OAc in Water:Acetonitrile (02:98); Gradient: 80-98% B over 2.5 minutes, flow rate 1 mL/min, then a 1.0 minute hold at 98% B flow rate 1.0 mL/min; then Gradient: 100-20% B over 0.1 minutes, flow rate 1.0 mL/min.

Method DS: Chiralpak AD-H (250×4.6) mm, 5.0 μm; Co-Solvent: 0.2% DEA in Methanol; Co-Solvent percentage: 15%, Column Temperature: 30° C.; Back Pressure: 100 bars; Total Flow: 3 g/min.

Method DT: Column: Chiralcel-OJ-H (250×30) mm, 5.0 μm; Mobile Phase-A: 0.2% TEA in n-HEPTANE; Mobile Phase-B: ETHANOL; Flow: 25 ml/min; Mode: Isocratic: A:B=90:10, Run time: 15 min.

Method DU: Column: Chiralpak AD-H (250×30) mm, 5 μm; Co-Solvent: 15% (0.2% DEA in Methanol); Co-Solvent percentage: 15%, Column Temperature: 30° C.; Back Pressure: 100 bars; Total Flow: 80 g/min.

Method DV: Column: Chiralcel OJ-H (250×30) mm, 5 μm; Mobile Phase-A: 0.2% DEA in n-Hexane; Mobile Phase-B: EtOH; Flow: 27 ml/min; Mode: Isocratic: A:B=95:05, Run time 40.0 min.

Method DW: Column: Chiralcel AS-H (250×30 mm) mm, 5.0 μm; Mobile Phase-A: 0.2% DEA in n-Hexane; Mobile Phase-B: EtOH; Flow: 27 ml/min; Mode: Isocratic: A:B=95:05.

Method DX: Column: Chiralcel OJ-H (250×30) mm, 5 μm; Mobile Phase-A: 0.2% DEA in n-Hexane; Mobile Phase-B: EtOH; Flow: 25 ml/min; Mode: Isocratic: A:B=95:05.

Method DY: Column: Chiralcel-OJH (250×4.6) mm, 5.0 μm; Co-Solvent: 0.2% DEA in n-Hexane:EtOH (90:10) Total Flow: 1 mL/min.

Method DZ: Column: Chiralpak-OJH (250×4.6) mm, 5.0 μm; Co-Solvent: 0.2% DEA in n-Hexane:EtOH (70:30) Total Flow: 1 mL/min Method EA: Column: Chiralpak AD-H (250×4.6) mm, 5.0 μm; Isocratic Mode, Co-Solvent: 0.2% DEA in Methanol; Co-Solvent percentage: 25%, Column Temperature: 25° C.; Back Pressure: 100 bars; Total Flow: 3 g/min; CO$_2$ flow: 2.25 g/min; Co-Solvent flow: 0.75 g/min.

Method EB: Column: Chiralpak AD-H (250×4.6) mm, 5.0 μm; Isocratic Mode, Co-Solvent: 0.2% DEA in IPA; Co-Solvent percentage: 10%, Column Temperature: 24.9° C.; Back Pressure: 100 bars; Total Flow: 3 g/min; CO$_2$ flow: 2.7 g/min; Co-Solvent flow: 0.3 g/min.

Method EC: Column: Chiralpak IC (250×4.6) mm, 5.0 μm; Isocratic Mode, Co-Solvent: 0.2% DEA in Methanol; Co-Solvent percentage: 30%, Column Temperature: 30° C.; Back Pressure: 100 bars; Total Flow: 3 g/min; CO$_2$ flow: 2.1 g/min.

Method ED: Column: Lux Cellulose-4 (250×4.6) mm, 5.0 μm; Co-Solvent: 0.2% DEA in Methanol: Methanol, (1:1); Co-Solvent percentage: 20%, Column Temperature: 25° C.; Back Pressure: 101 bars; Total Flow: 3 g/min.

Method EE: Column: Chiralcel OD-H (250×30) mm, 5.0 μm; Co-Solvent: 0.2% DEA in Methanol; Co-Solvent: 20%; Total Flow: 120.0 g/min; Back Pressure: 100 bars.

Method EF: Column: Chiralpak AS-H (250×21) mm, 5 μm; Mobile Phase A: 0.2% DEA in n-Hexane; Mobile Phase B: IPA; Flow: 20 ml/min; Mode: Isocratic: A:B=90:10.

Method EG: Column ChiralCel ODH (250×4.6) mm, 5 μm; Co-Solvent IPA:ACN (1+1); Column Temperature 24.7; Total Flow 3 g/min; CO$_2$ Flow Rate 2.7 g/min; Co-Solvent Flow Rate 0.3 g/min; Co-Solvent percentage 10%; Back Pressure: 100 bars.

Method EH: Waters Acquity SDS using the following method: Linear Gradient of 2% to 98% solvent B over 1.00 min; UV visualization at 220 or 254 nm; Column: BEH C18 2.1 mm×50 mm; 1.7 um particle (Heated to Temp. 50° C.); Flow rate: 0.8 ml/min; Mobile phase A: 100% Water, 0.05% TFA; Mobile phase B: 100% Acetonitrile, 0.05% TFA.

Method EI: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

Example 1

Diastereomer 1, Diastereomer 2, Diastereomer 3, Diastereomer 4

(S)-3-(4-((1s,4R)-4-phenylcyclohexyl)-3-(3-(p-tolyl)ureido)phenyl)pentanoic Acid (S)-3-(4-((1r,4S)-4-phenylcyclohexyl)-3-(3-(p-tolyl)ureido)phenyl)pentanoic Acid (R)-3-(4-((1s,4S)-4-phenylcyclohexyl)-3-(3-(p-tolyl)ureido)phenyl)pentanoic Acid (R)-3-(4-((1r,4R)-4-phenylcyclohexyl)-3-(3-(p-tolyl)ureido)phenyl)pentanoic Acid (Absolute Stereochemistry not Determined)

Dia-1
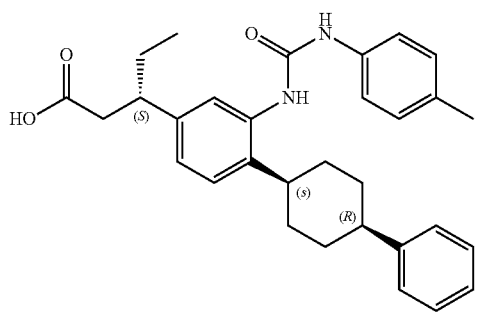

Dia-2
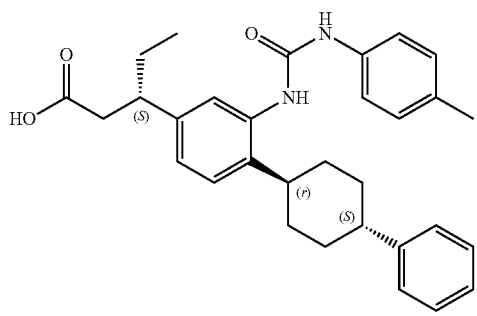

Dia-3
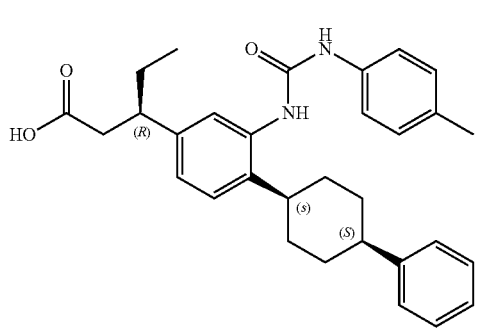

Dia-4
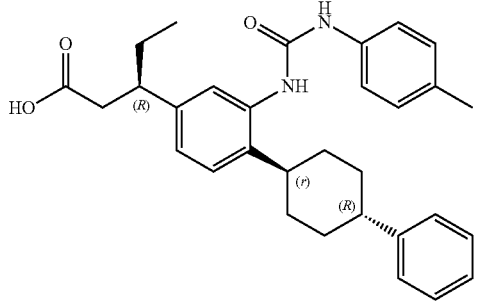

1A. 1,4-dioxaspiro[4.5]dec-7-en-8-yl trifluoromethanesulfonate

To a stirred solution of commercially available 1,4-dioxaspiro[4.5]decan-8-one (5.0 g, 32.0 mmol) and 1,1,1-trifluoro-N-phenyl-N-((trifluoromethyl)sulfonyl)methanesulfonamide (14.87 g, 41.6 mmol) in THF (350 mL) under $N_2$ at −78° C., was added KHMDS (83 mL, 41.6 mmol) in toluene. The reaction mixture was stirred for 4 h. The reaction mixture was quenched with water and extracted with ether (300 mL). The organic layer was dried over $Na_2SO_4$, filtered and concentrated under reduced pressure. The crude material was purified by silica gel chromatography to give 1A (6.0 g, 20.82 mmol, 65.0% yield) as a clear oil. $^1$H NMR (400 MHz, DMSO-$d_6$) δ 5.79-5.81 (m, 1H), 3.89 (s, 4H), 2.34-2.51 (m, 4H), 1.82-1.85 (m, 2H).

1B. 8-phenyl-1,4-dioxaspiro[4.5]dec-7-ene

A solution of DME (40 mL) and 2M aq. $Na_2CO_3$ (8.85 mL, 17.69 mmol) was purged with nitrogen for 20 min. Then 1A (3.0 g, 10.41 mmol), phenylboronic acid (1.904 g, 15.61 mmol), $PdCl_2$(dppf)-$CH_2Cl_2$ Adduct (0.425 g, 0.520 mmol) were added and stirred in a sealed tube at 110° C. The reaction mixture was stirred at that temperature for 3.5 h. The reaction was diluted with ethyl acetate (200 mL), washed with water (100 mL), dried over $Na_2SO_4$, filtered and concentrated under reduced pressure. The residue was purified by silica gel chromatography to give 1B (colorless liquid, 1.5 g, 5.69 mmol, 54.6% yield). $^1$H NMR (300 MHz, CDCl$_3$) δ 7.22-7.40 (m, 5H), 5.98 (q, J=2.40 Hz, 1H), 4.03 (s, 4H), 2.65-2.69 (m, 2H), 2.47 (s, 2H), 1.93 (t, J=6.60 Hz, 2H).

1C. 8-phenyl-1,4-dioxaspiro[4.5]decane 1B (1.5 g, 6.94 mmol) in MeOH (75 mL) was placed in a hydrogenation autoclave under 40 psi at room temperature using 10% Pd/C (300 mg, 0.282 mmol) as catalyst for 3 h. The resulting solution was filtered through a pad of Celite, concentrated and purified by silica gel chromatography to afford 1C (white solid, 1.1 g, 4.95 mmol, 71.3% yield). $^1$H NMR (400 MHz, DMSO-$d_6$) δ 7.15-7.29 (m, 5H), 3.90 (s, 4H), 1.57-1.77 (m, 8H), (Note: one multiplet CH was buried under solvent peak).

1D. 4-phenylcyclohexanone

Compound 1C (1.0 g, 4.58 mmol) was treated with HCl (20 ml, 40.0 mmol) in Acetone (40 mL) at room temperature for 4 h. The reaction was neutralized with saturate NaHCO$_3$ solution (30 mL) and the solvent was removed. The residue was partitioned between ethyl acetate (100 mL) and water (50 mL). The organic layer was washed with brine, dried over anhydrous $Na_2SO_4$, filtered and concentrated to give 1D (off white solid, 0.7 g, 4.02 mmol, 88% yield). $^1$H NMR (300 MHz, $CDCl_3$) δ 7.20-7.35 (m, 5H), 2.99-3.08 (m, 1H), 2.49-2.54 (m, 4H), 2.19-2.26 (m, 2H), 1.90-2.02 (m, 2H).

1E. 1,2,3,6-tetrahydro-[1,1'-biphenyl]-4-yl trifluoromethanesulfonate

A solution of diisopropylamine (0.532 mL, 3.73 mmol) in THF (5.0 mL) under nitrogen at −20° C. was treated with a 2.5 M solution of n-butyllithium (1.377 mL, 3.44 mmol) and stirred for 15 minutes. The resulting mixture was cooled to −78° C. Then a solution of 1D (0.5 g, 2.87 mmol) in THF (5.0 mL) was added over 20 minutes. The resulting solution was stirred at −78° C. for 3 h then treated with a solution of N,N-bis(trifluoromethylsulfonyl)aniline (2.15 g, 6.02 mmol) in THF (5 mL). The mixture was stirred at −78° C. for 1.5 h then warmed to room temperature and stirred for 18 h. The reaction mixture was concentrated under reduced pressure and the resulting residue partitioned between ethyl acetate (50 mL) and water (25 mL). The organic layer was washed with 2M sodium hydroxide solution and brine and then dried over sodium sulfate. The solvent was removed under reduced pressure. Purification via flash chromatography gave 1E (colorless oil, 0.3 g, 0.979 mmol, 34.1% yield). $^1$H NMR (400 MHz, $CDCl_3$) δ 7.21-7.42 (m, 5H), 5.85-5.87 (m, 1H), 2.80-2.90 (m, 1H), 2.36-2.51 (m, 4H), 1.97-2.07 (m, 2H).

1F. 4,4,5,5-tetramethyl-2-(1,2,3,6-tetrahydro-[1,1'-biphenyl]-4-yl)-1,3,2-dioxaborolane In a sealed tube 1E (0.3 g, 0.979 mmol), BISPIN (0.373 g, 1.469 mmol) and potassium acetate (0.288 g, 2.94 mmol) in DMF (5.0 mL) purged with Argon for 20 min. To this $PdCl_2$(dppf)-$CH_2Cl_2$ Adduct (0.040 g, 0.049 mmol) was added and purged with Argon for 5 min. The reaction mixture was heated at 85° C. for 18 h. Reaction mixture was cooled to room temperature and it was filtered through a pad of Celite. The pad of Celite was rinsed with dichloromethane (3×40 mL) and the filtrate was concentrated under reduced pressure to get residue which was diluted with dichloromethane (50 mL) and water (50 mL). Aqueous layer was extracted with DCM (2×50 mL). The combined organic layer was washed with brine (50 mL), dried over anhydrous sodium sulphate and concentrated under reduced pressure. Purification via flash chromatography gave 1F (colorless liquid, 0.2 g, 0.704 mmol, 71.9% yield). $^1$H NMR (300 MHz, $CDCl_3$) δ 7.16-7.32 (m, 5H), 6.65-6.66 (m, 1H), 2.74-2.82 (m, 1H), 2.17-2.44 (m, 4H), 1.93-2.04 (m, 1H), 1.67-1.72 (m, 1H), 1.28 (s, 12H).

1G. 1-(4-hydroxy-3-nitrophenyl)propan-1-one

To a stirred conc. $H_2SO_4$ (100 ml, 1876 mmol) at 3° C. was added 1-(4-hydroxyphenyl)propan-1-one (10.0 g, 66.6 mmol) followed by potassium nitrate (8.08 g, 80 mmol) in two approximately equal portions about 4 minutes apart. The reaction was slowly poured into crushed ice/water mixture and was extracted with ethyl acetate (200 mL). Organic layer was concentrated in vacuo to give 1G (yellow solid, 9.0 g, 46.1 mmol, 69.3% yield). $^1$H NMR (400 MHz, $CDCl_3$) δ 10.89 (s, 1H), 8.73 (d, J=2.40 Hz, 1H), 8.22 (dd, J=2.00, 8.80 Hz, 1H), 7.24 (d, J=8.80 Hz, 1H), 2.50 (q, J=7.20 Hz, 2H), 1.24 (t, J=7.20 Hz, 3H).

1H. 1-(4-(benzyloxy)-3-nitrophenyl)propan-1-one

To a solution of 1G (9.0 g, 46.1 mmol) in dry Acetonitrile (90 mL) was added DIPEA (8.86 mL, 50.7 mmol) in drop wise manner at 0° C. under argon atmosphere. After 3 min, benzyl bromide (6.03 mL, 50.7 mmol) was added to the reaction mixture which was then allowed to warm to room temperature and stirred at 85° C. for 4 h. The reaction mixture was cooled with a water bath. Then the reaction mixture was added drop wise to the cold water. The resultant solid was filtered, washed with hexane (2×50 mL) and dried under vacuum to get 1H (yellow solid, 11.5 g, 39.3 mmol, 85% yield). $^1$H NMR (400 MHz, $CDCl_3$) δ 8.44 (d, J=2.00 Hz, 1H), 8.12 (dd, J=2.40, 8.80 Hz, 1H), 7.35-7.46 (m, 5H), 7.18 (d, J=8.80 Hz, 1H), 5.32 (s, 2H), 2.97 (q, J=7.20 Hz, 2H), 1.23 (t, J=7.20 Hz, 3H).

1I. (E,Z) ethyl 3-(4-(benzyloxy)-3-nitrophenyl)pent-2-enoate

To a slurry of NaH (0.308 g, 7.71 mmol) in THF (13 mL) at 0° C. was added ethyl 2-(diethoxyphosphoryl)acetate (1.572 g, 7.01 mmol). After 15 min, 1H (1.0 g, 3.51 mmol) in THF (5 mL)) was added to the reaction mixture and was stirred at RT for 2 h. Then the reaction mixture was heated at 50° C. for 2 h. The reaction mixture was cooled to RT and was quenched with saturated aqueous $NH_4Cl$ (10 mL). The aqueous layer was further extracted with EtOAc (2×200 mL) and the combined organic extracts were washed with water (100 mL), brine (50 mL), dried over $MgSO_4$, filtered and concentrated under reduced pressure. Purification via flash chromatography gave 1I (Diastereomer Mixture, yellow solid, 1.0 g, 2.79 mmol, 79% yield). (dr=57.8:42.2 by 1H NMR)$^1$H NMR (Diastereomer Mixture, 400 MHz, $CDCl_3$) δ 7.96 (d, J=2.40 Hz, 1H), 7.57-7.60 (m, 1H), 7.32-7.36 (m, 6H), 6.01 (s, 1H), 5.27 (s, 2H), 4.21 (q, J=7.20 Hz, 2H), 3.06 (q, J=7.20 Hz, 2H), 1.31 (t, J=6.80 Hz, 3H), 1.04-1.13 (m, 3H); minor diastereomer (visible peaks) δ 7.72 (d, J=2.40 Hz), 7.38-7.59 (m), 7.08-7.13 (m), 5.91 (s), 5.25 (s), 4.02 (q, J=7.20 Hz), 2.45 (q, J=1.20 Hz), 1.04-1.13 (m).

1J. (E,Z) ethyl 3-(3-amino-4-(benzyloxy)phenyl)pent-2-enoate

To a solution of 1I (0.2 g, 0.563 mmol) in Ethanol (4.00 mL) and Water (0.8 mL) was added Zn (0.368 g, 5.63 mmol) and ammonium chloride (0.301 g, 5.63 mmol) at 0° C. and the mixture was stirred at room temperature for 1 h. The reaction mixture was diluted with DCM (50 mL), washed with water (10 mL), brine (10 mL), dried over $Na_2SO_4$ and concentrated under reduced pressure. Purification via flash chromatography gave 1J (Mixture of diastereomer, pale yellow solid, 0.17 g, 0.512 mmol, 91% yield). LC-MS Anal. Calc'd for $C_{20}H_{23}NO_3$ 325.402. found [M+H] 326.2, $T_r$=3.229 min (Diastereomer 1) and found [M+H] 326.2, $T_r$=3.427 min (Diastereomer 2) (Method U).

1K. (E,Z) ethyl 3-(4-(benzyloxy)-3-(3-(p-tolyl)ureido)phenyl)pent-2-enoate

To a solution of 1J (0.17 g, 0.522 mmol) in DCM (2.0 mL) was added 1-isocyanato-4-methylbenzene (0.077 g, 0.575 mmol) at 0° C. The mixture was allowed to warm to room temperature and was stirred for 1 h. The reaction mixture was concentrated under reduced pressure. The resultant solid was washed with hexane (2×10 mL) and dried under vacuum to get 1K (Mixture of diastereomer, off white solid, 0.22 g, 0.432 mmol, 83% yield). LC-MS Anal. Calc'd for $C_{28}H_{30}N_2O_4$ 458.549. found [M+H] 459.5, $T_r$=1.62 min (Diastereomer 1) and found [M+H] 459.5, $T_r$=1.68 min (Diastereomer 2) (Method U).

1L. ethyl 3-(4-hydroxy-3-(3-(p-tolyl)ureido)phenyl)pentanoate

The solution of 1K (1.0 g, 2.181 mmol)) in Ethyl acetate (80 mL) was charged to a sealable hydrogen flask. The solution was sequentially evacuated and purged with nitrogen gas. To this 10% Pd on carbon (0.116 g, 0.109 mmol) was added under nitrogen atmosphere. The reaction mixture was stirred under hydrogen atmosphere (40 psi) at RT for 3 h. The reaction mixture was filtered through a Celite pad and the residue on the pad was thoroughly rinsed with MeOH (3×50 mL). The combined filtrate was concentrated under reduced pressure. Purification via flash chromatography gave 1L (white solid, 0.65 g, 1.607 mmol, 73.7% yield). LC-MS Anal. Calc'd for $C_{21}H_{26}N_2O_4$ 370.442. found [M+H] 371.2, $T_r$=2.901 min (Method U).

1M. ethyl 3-(3-(3-(p-tolyl)ureido)-4-(((trifluoromethyl)sulfonyl)oxy)phenyl)pentanoate To a 10 mL round bottom flask under a nitrogen atmosphere were charged with 1L (0.5 g, 1.350 mmol) and N,N-bis(Trifluoromethylsulfonyl)aniline (0.627 g, 1.755 mmol) dissolved in anhydrous DCM (25 mL). The stirred solution was cooled to 0° C. for 1 h and TEA (0.245 mL, 1.755 mmol) was added drop wise. The reaction was allowed to warm up to ambient temperature and was stirred for 18 h. The reaction mixture was diluted with diethyl ether (50 mL) which was washed with water and brine, dried over $Na_2SO_4$ and concentrated under reduced pressure. Purification via flash chromatography gave 1M (off white solid, 0.6 g, 1.194 mmol, 88% yield). $^1$H NMR (400 MHz, DMSO-$d_6$) δ 8.53 (s, 1H), 8.49 (s, 1H), 7.09-7.34 (m, 6H), 6.80 (d, J=7.60 Hz, 1H), 3.96 (q, J=1.60 Hz, 2H), 2.86-3.32 (m, 1H), 2.61-2.67 (m, 1H), 2.24 (s, 3H), 1.53-1.76 (m, 2H), 1.23 (s, 1H), 1.06 (t, J=3.60 Hz, 3H), 0.74 (t, J=7.20 Hz, 3H).

1N. ethyl 3-(2-(3-(p-tolyl)ureido)-2',3',4',5'-tetrahydro-[1,1':4',1''-terphenyl]-4-yl)pentanoate To a solution of 1M (0.424 g, 0.844 mmol) in degassed Dioxane (6.0 mL) and 2M $Na_2CO_3$ (1.056 mL, 2.111 mmol) was added 4,4,5,5-tetramethyl-2-(1,2,3,6-tetrahydro-[1,1'-biphenyl]-4-yl)-1,3,2-dioxaborolane (0.2 g, 0.704 mmol) and $PdCl_2$(dppf)-$CH_2Cl_2$ Adduct (0.029 g, 0.035 mmol). The reaction was heated in an oil bath to 110° C. for 3 h. The reaction mixture was cooled to room temperature and then diluted with EtOAc (100 mL) and water. The resultant dark emulsions filtered to get rid of the solids, and then extracted with ethyl acetate (100 mL), dried over $Na_2SO_4$, and concentrated under reduced pressure. Purification via flash chromatography gave 1N (Off white solid, 0.2 g, 0.360 mmol, 51.2% yield). LC-MS Anal. Calc'd for $C_{33}H_{38}N_2O_3$ 510.666. found [M+H] 511.4, $T_r$=4.039 min (Method U).

1O. ethyl 3-(4-(4-phenylcyclohexyl)-3-(3-(p-tolyl)ureido)phenyl)pentanoate

The solution of 1N (0.2 g, 0.392 mmol) in MeOH (10 mL) was charged to a sealable hydrogen flask. The solution was sequentially evacuated and purged with nitrogen gas. To this 10% Pd on carbon (0.02 g, 0.019 mmol) was added under nitrogen atmosphere. The reaction mixture was stirred under hydrogen atmosphere (40 psi) at RT for 3 h. The reaction mixture was filtered through a celite pad and the residue on the pad was thoroughly rinsed with MeOH (3×50 mL). The combined filtrate was concentrated under reduced pressure. Purification via flash chromatography gave 82O (white solid, 0.2 g, 0.351 mmol, 90% yield). LC-MS Anal. Calc'd for $C_{33}H_{40}N_2O_3$ 512.682. found [M+H] 513.2, $T_r$=4.185 min (Method U).

Example 1. 3-(4-(4-phenylcyclohexyl)-3-(3-(p-tolyl)ureido)phenyl)pentanoic acid (Absolute Stereochemistry not Determined)

A solution of 1O (0.2 g, 0.390 mmol) in THF (1.0 mL), MeOH (1.0 mL) was treated with lithium hydroxide (0.028 g, 1.170 mmol) in Water (1.0 mL) and the reaction was stirred at RT for 4 h. The reaction mixture was concentrated under reduced pressure. The aqueous residue so obtained was acidified with 1(N) HCl to pH~2. The aqueous layer was diluted with water (5 mL) and extracted with ethyl acetate (2×20 mL). Combined organic layer was washed with water (10 mL), brine (10 mL), dried over anhydrous sodium sulfate and concentrated under reduced pressure to afford a residue of the Diasteriomeric mixture of Example 1. Preparative HPLC of diastereomeric mixture of Example 1 gave Example 1 Mixture A and Example 1 Mixture B.

Example 1 Mixture A (off white solid, 60 mg), $T_r$=18.620 min and Example 1 Mixture B (off white solid, 60 mg), $T_r$=21.059 min.

Chiral separation of Example 1 Mixture A gave Example 1 Diastereomer 1, $T_r$=9.06 min and Example 1 Diastereomer 2, $T_r$=10.76 min (Method AB).

Example 1 Diastereomer 1 (Off white solid, 11.6 mg, 0.024 mmol, 6.14% yield): LC-MS Anal. Calc'd for $C_{31}H_{36}N_2O_3$ 484.629. found [M+H] 485.3, $T_r$=2.670 min (Method R). $^1$H NMR (400 MHz, DMSO-d6) δ 8.88 (s, 1H), 7.84 (s, 1H), 7.53 (s, 1H), 7.32-7.40 (m, 6H), 7.19 (t, J=8.00 Hz, 1H), 7.09 (d, J=8.40 Hz, 2H), 7.04 (d, J=8.00 Hz, 1H), 6.85 (d, J=8.00 Hz, 1H), 2.74-3.03 (m, 3H), 2.42-2.55 (m, 2H), 2.25 (s, 3H), 2.15-2.16 (m, 2H), 1.93-1.86 (m, 2H), 1.44-1.70 (m, 6H), 0.73 (t, J=7.20 Hz, 3H).

Example 1 Diastereomer 2 (Off white solid, 8.3 mg, 0.017 mmol, 4.30% yield): LC-MS Anal. Calc'd for $C_{31}H_{36}N_2O_3$ 484.629. found [M+H] 485.3, $T_r$=2.670 min (Method R). $^1$H NMR (400 MHz, DMSO-d6) δ 8.84 (s, 1H), 7.86 (s, 1H), 7.52 (d, J=2.00 Hz, 1H), 7.26-7.37 (m, 6H), 7.16-7.23 (m, 2H), 7.09 (d, J=8.40 Hz, 2H), 6.92 (dd, J=2.00, 8.20 Hz, 1H), 2.64-2.84 (m, 2H), 2.54-2.58 (m, 1H), 2.41-2.52 (m, 2H), 2.25 (s, 3H), 1.86-1.95 (m, 4H), 1.58-1.68 (m, 6H), 0.75 (t, J=7.20 Hz, 3H).

Chiral separation of Example 1 Mixture B gave Example 1 Diastereomer 3, $T_r$=4.91 min and Example 1 Diastereomer 4, $T_r$=6.45 min (Method CF).

Example 1 Diastereomer 3 (Off white solid, 14.2 mg, 0.029 mmol, 7.51% yield): LC-MS Anal. Calc'd for $C_{31}H_{36}N_2O_3$ 484.629. found [M+H] 485.3, $T_r$=2.637 min (Method R). $^1$H NMR (400 MHz, DMSO-$d_6$) δ 8.85 (s, 1H), 7.87 (s, 1H), 7.52 (s, 1H), 7.17-7.38 (m, 8H), 7.09 (d, J=8.00 Hz, 2H), 6.93 (d, J=8.00 Hz, 1H), 2.81-0.00 (m, 2H), 2.41-2.68 (m, 3H), 2.25 (s, 3H), 1.87-1.95 (m, 4H), 1.53-1.69 (m, 6H), 0.75 (t, J=7.20 Hz, 3H).

Example 1 Diastereomer 4 (Off white solid, 13.2 mg, 0.027 mmol, 6.98% yield): LC-MS Anal. Calc'd for $C_{31}H_{36}N_2O_3$ 484.629. found [M+H] 485.3, $T_r$=2.641 min.

$^1$H NMR (400 MHz, DMSO-d$_6$) δ 8.86 (s, 1H), 7.82 (s, 1H), 7.53 (d, J=1.60 Hz, 1H), 7.32-7.40 (m, 6H), 7.18-7.21 (m, 1H), 7.04-7.10 (m, 3H), 6.86 (dd, J=1.60, 8.00 Hz, 1H), 2.80-3.03 (m, 3H), 2.42-2.44 (m, 2H), 2.25 (s, 3H), 2.15-2.18 (m, 2H), 1.92-1.93 (m, 2H), 1.60-1.70 (m, 6H), 0.73 (t, J=7.60 Hz, 3H).

Example 2

Homochiral (R)-3-(3-((4-chloro-2-fluorophenyl)amino)-4-(1-methyl-1H-pyrazol-4-yl)phenyl)pentanoic Acid (Absolute Stereochemistry not Determined)

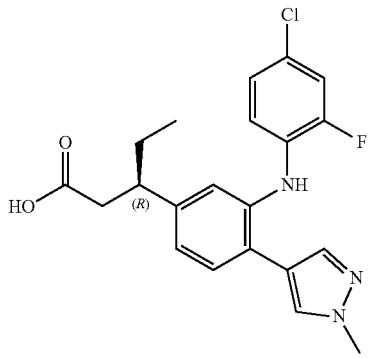

2A. methyl 3-(4-bromophenyl)pentanoate

In a pressure tube equipped with teflon cap, (4-bromophenyl)boronic acid (8 g, 39.8 mmol) in 1,4-Dioxane (130 mL) were added (E)-methyl pent-2-enoate (14.83 mL, 120 mmol), (S)-BINAP (0.546 g, 0.876 mmol) and sodium hydroxide (1.0 M in water, 35.9 mL, 35.9 mmol). Then Argon gas was bubbled through the mixture for 10 min and chlorobis(ethylene)rhodium(I) dimer (0.232 g, 0.598 mmol) was added at room temperature. Argon gas was bubbled through the mixture for another 5 min. The tube was then screw-capped and stirred at room temperature for 3 h. The reaction mixture was quenched with acetic acid (2.052 mL, 35.9 mmol), stirred for 5 minutes and then it was diluted with water (100 mL). The aqueous layer was extracted with ethyl acetate (3×50 mL). The combined organic layer was washed with water (50 mL), brine (50 mL), dried over anhydrous sodium sulfate, filtered and concentrated under reduced pressure to afford a residue which was purified via flash silica gel column chromatography to afford 2A (colorless liquid, 7.2 g, 26.6 mmol, 66.7% yield). $^1$H NMR (300 MHz, chloroform-d) δ 7.43 (d, J=8.30 Hz, 2H), 7.07 (d, J=8.30 Hz, 2H), 3.60 (s, 3H), 2.94-3.06 (m, 1H), 2.49-2.70 (m, 2H), 1.59-1.78 (m, 2H), 0.80 (t, J=7.36 Hz, 3H).

2B. methyl 3-(4-bromo-3-nitrophenyl)pentanoate

To a stirred solution of 2A (7.2 g, 25.2 mmol) in conc. H$_2$SO$_4$ (70 mL) at 0° C., potassium nitrate (2.55 g, 25.2 mmol) was added in portion wise and stirred at same temperature for 30 min. The completion of reaction was adjudged by the disappearance of starting material by TLC. The reaction mixture was added to ice water (100 mL) and extracted with ethyl acetate (2×100 mL). The organic layer was washed with saturated aqueous NaHCO$_3$ solution (100 mL), brine (50 mL), dried over sodium sulfate, filtered and evaporated under reduced pressure to provide the crude product of 2B (light yellow oil, 7 g, 22.14 mmol, 88% yield). $^1$H NMR (400 MHz, chloroform-d) δ 7.63-7.69 (m, 2H), 7.24-7.30 (m, 1H), 3.60 (s, 3H), 3.04-3.13 (m, 1H), 2.65-2.74 (m, 1H), 2.51-2.61 (m, 1H), 1.74-1.76 (m, 1H), 1.61-1.63 (m, 1H), 0.82 (t, J=7.28 Hz, 3H).

2C. methyl 3-(3-amino-4-bromophenyl)pentanoate (Absolute Stereochemistry not Determined)

To a stirred solution of 2B (7 g, 22.14 mmol) in methanol (15 mL), was added ammonium chloride (9.48 g, 177 mmol) in H$_2$O (35 mL) followed by Iron (6.18 g, 111 mmol). The reaction suspension was heated at 65° C. for 4 h. The reaction mixture was allowed to cool to room temperature and filtered through a pad of Celite. The Celite pad was washed with excess of methanol and concentrated under reduced pressure to afford the brown colored oil. The oily compound was reconstituted in ethyl acetate (50 mL) and aqueous saturated sodium bicarbonate solution (50 mL). The organic layer was separated and the aqueous layer was again extracted with ethyl acetate (2×50 mL). Organic extracts were combined and was washed with water, brine, dried over sodium sulfate and concentrated to provide brown colored oil.

Chiral separation of enantiomeric mixture 2C (Method Z, ee 81%) gave Enantiomer 1 and Enantiomer 2 as single enantiomer. Enantiomer 1, T$_r$=6.55 min (Method Z) as a major product and Enantiomer 2, T$_r$=7.95 min (Method Z).

2C Enantiomer 1 (pale red liquid, 4 g, 13.14 mmol, 59% yield): LC-MS Anal. Calc'd for C$_{12}$H$_{16}$BrNO$_2$ 286.1. found [M+2] 288.0, T$_r$=1.78 min (Method BD).

2D. methyl 3-(3-amino-4-(1-methyl-1H-pyrazol-4-yl)phenyl)pentanoate (Absolute Stereochemistry not Determined)

To a stirred solution of 2C Enantiomer 1 (600 mg, 2.097 mmol) in a mixture DME (8 mL) and Ethanol (2 mL) was added (1-methyl-1H-pyrazol-4-yl)boronic acid (317 mg, 2.52 mmol), K$_2$CO$_3$ (290 mg, 2.097 mmol) and purged with argon for 10 min. To the above reaction mixture tetrakis (triphenylphosphine)palladium(0) (121 mg, 0.105 mmol) was added and purged with argon for another 10 min. The reaction mixture was heated to 100° C. and stirred for 16 h. The reaction mixture was cooled to room temperature and poured into water (10 mL), extracted with EtOAc (2×10 mL). The combined organic layer was washed with brine (10 mL), dried over anhydrous sodium sulfate, filtered and concentrated under reduced pressure to give the crude sample which was purified by flash column chromatography to afford 2D (pale brown liquid, 440 mg, 1.531 mmol, 73.0% yield). LC-MS Anal. Calc'd for C$_{16}$H$_{21}$N$_3$O$_2$ 287.3. found [M+H] 288.2, T$_r$=2.04 min (Method N).

2E. methyl 3-(3-((4-chloro-2-fluorophenyl)amino)-4-(1-methyl-1H-pyrazol-4-yl)phenyl)pentanoate (Absolute Stereochemistry not Determined)

To a stirred solution of 2D (40 mg, 0.139 mmol) in 1,4-Dioxane (4 mL) was added 1-bromo-4-chloro-2-fluorobenzene (35.0 mg, 0.167 mmol), cesium carbonate (68.0 mg, 0.209 mmol) and purged with argon for 10 min. To the above reaction mixture 4,5-bis(diphenylphosphino)-9,9-dimethylxanthene (8.05 mg, 0.014 mmol), bis(dibenzylideneacetone)palladium (4.00 mg, 6.96 μmol) was added and purged with argon for another 10 min. Then the reaction mixture was heated to 110° C. and stirred for 12 h in a sealed vial. The reaction mixture was cooled to room temperature, concentrated under reduced pressure and diluted with ethyl acetate (10 mL). Organic layer was washed with water (2×5 mL), brine solution (5 mL), dried over $Na_2SO_4$, filtered and concentrated under reduced pressure to give the crude product 2E (pale brown liquid, 40 mg, 0.096 mmol, 69.1% yield) which was taken to next step without further purification. LC-MS Anal. Calc'd for $C_{22}H_{23}ClFN_3O_2$ 415.1. found [M+H] 416.2, $T_r$=1.55 min (Method AY).

Example 2. (R)-3-(3-((4-chloro-2-fluorophenyl) amino)-4-(1-methyl-1H-pyrazol-4-yl)phenyl)pentanoic Acid (Absolute Stereochemistry not Determined)

To a stirred solution of 2E (40 mg, 0.096 mmol) in a mixture of THF (1 mL), MeOH (1 mL) and $H_2O$ (0.5 mL) was added lithium hydroxide (18.43 mg, 0.769 mmol) and stirred at room temperature for 12 h. The reaction mixture was concentrated under reduced pressure. The residue was diluted with water (15 mL), acidified with saturated citric acid solution and extracted with ethyl acetate (2×20 mL). The combined organic layer was dried over sodium sulfate, filtered and concentrated under reduced pressure to give the crude material which was purified via preparative LCMS to give Example 2 (pale yellow solid, 12 mg, 0.030 mmol, 30.7% yield). LC-MS Anal. Calc'd for $C_{21}H_{21}ClFN_3O_2$ 401.1. found [M+H] 402.1, $T_r$=2.09 min (Method N). $^1$H NMR (400 MHz, MeOD) δ 7.80 (s, 1H), 7.67 (s, 1H), 7.44 (d, J=8.00 Hz, 1H), 7.14 (d, J=2.00 Hz, 1H), 7.04-7.12 (m, 2H), 6.90 (d, J=8.80 Hz, 1H), 6.73 (t, J=8.80 Hz, 1H), 3.87 (s, 3H), 2.95-2.98 (m, 1H), 2.57-2.65 (m, 2H), 1.72-1.77 (m, 1H), 1.62-1.67 (m, 1H), 0.85 (t, J=7.20 Hz, 3H).

Example 3-16

Homochiral

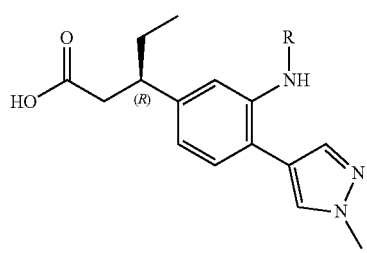

Example 3-16 were prepared from 2D and corresponding aryl halides following the procedure described for the synthesis of Example 101.

| Ex. No. | Name | R | Tr min | Method | (M + H) |
|---|---|---|---|---|---|
| 3 | (R)-3-(3-((4-fluorophenyl)amino)-4-(1-methyl-1H-pyrazol-4-yl)phenyl)pentanoic acid (absolute stereochemistry not determined) | F | 1.47 | O | 368.1 |
| 4 | (R)-3-(3-((4-chlorophenyl)amino)-4-(1-methyl-1H-pyrazol-4-yl)phenyl)pentanoic acid (absolute stereochemistry not determined) | Cl | 1.65 | O | 384.1 |
| 5 | (R)-3-(3-((4-cyanophenyl)amino)-4-(1-methyl-1H-pyrazol-4-yl)phenyl)pentanoic acid (absolute stereochemistry not determined) | CN | 1.32 | O | 375.2 |
| 6 | (R)-3-(3-((5-chloropyridin-2-yl)amino)-4-(1-methyl-1H-pyrazol-4-yl)phenyl)pentanoic acid (absolute stereochemistry not determined) | Cl | 1.36 | O | 385.1 |
| 7 | (R)-3-(3-((3-chlorophenyl)amino)-4-(1-methyl-1H-pyrazol-4-yl)phenyl)pentanoic acid (absolute stereochemistry not determined) | Cl | 1.63 | O | 384.1 |
| 8 | (R)-3-(3-((3-fluorophenyl)amino)-4-(1-methyl-1H-pyrazol-4-yl)phenyl)pentanoic acid (absolute stereochemistry not determined) | F | 1.49 | O | 368.1 |
| 9 | (R)-3-(3-((4-chloro-3-fluorophenyl)amino)-4-(1-methyl-1H-pyrazol-4-yl)phenyl)pentanoic acid (absolute stereochemistry not determined) | Cl, F | 1.69 | O | 402.1 |
| 10 | (R)-3-(4-(1-methyl-1H-pyrazol-4-yl)-3-(p-tolylamino)phenyl)pentanoic acid (absolute stereochemistry not determined) | $CH_3$ | 1.67 | O | 364.2 |
| 11 | (R)-3-(4-(1-methyl-1H-pyrazol-4-yl)-3-(pyridin-3-ylamino)phenyl)pentanoic acid (absolute stereochemistry not determined) | N | 0.88 | O | 351.2 |

-continued

| Ex. No. | Name | R | Tr min | Method | (M + H) |
|---|---|---|---|---|---|
| 12 | (R)-3-(4-(1-methyl-1H-pyrazol-4-yl)-3-((2-methylpyrimidin-5-yl)amino)phenyl)pentanoic acid (absolute stereochemistry not determined) | 2-methylpyrimidin-5-yl | 0.80 | O | 366.2 |
| 13 | (R)-3-(3-((2-ethylpyrimidin-5-yl)amino)-4-(1-methyl-1H-pyrazol-4-yl)phenyl)pentanoic acid (absolute stereochemistry not determined) | 2-ethylpyrimidin-5-yl | 0.89 | O | 380.3 |
| 14 | (R)-3-(4-(1-methyl-1H-pyrazol-4-yl)-3-((4-(trifluoromethyl)phenyl)amino)phenyl)pentanoic acid (absolute stereochemistry not determined) | 4-CF3-phenyl | 1.51 | O | 418.2 |
| 15 | (R)-3-(4-(1-methyl-1H-pyrazol-4-yl)-3-(pyridin-2-ylamino)phenyl)pentanoic acid (absolute stereochemistry not determined) | pyridin-2-yl | 0.928 | O | 351.2 |
| 16 | (R)-3-(3-((5-cyanopyridin-2-yl)amino)-4-(1-methyl-1H-pyrazol-4-yl)phenyl)pentanoic acid (absolute stereochemistry not determined) | 5-cyanopyridin-2-yl | 0.932 | O | 376.2 |

Example 17

Homochiral (R)-3-(3-((4-chlorophenyl)amino)-4-(3,5-dimethylisoxazol-4-yl)phenyl)pentanoic Acid (Absolute Stereochemistry not Determined)

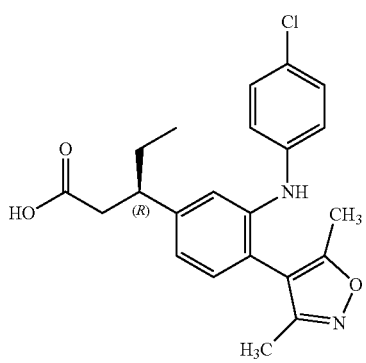

17A. methyl 3-(4-bromo-3-((4-chlorophenyl)amino)phenyl)pentanoate (Absolute Stereochemistry not Determined)

To a stirred solution of 2C Enantiomer 1 (500 mg, 1.747 mmol) in 1,4-Dioxane (8 mL) was added 1-bromo-4-chlorobenzene (401 mg, 2.097 mmol), cesium carbonate (854 mg, 2.62 mmol) and purged with argon for 10 min. To the above reaction mixture 4,5-bis(diphenylphosphino)-9,9-dimethylxanthene (101 mg, 0.175 mmol), bis(dibenzylideneacetone)palladium (50.2 mg, 0.087 mmol) was added and purged with argon for another 10 min. Then the reaction mixture was heated to 110° C. and stirred for 12 h in a sealed vial. The reaction mixture was cooled to room temperature, concentrated under reduced pressure and diluted with ethyl acetate (25 mL). Organic layer was washed with water (2×25 mL), brine solution (25 mL), dried over $Na_2SO_4$, filtered and concentrated under reduced pressure. The crude sample was purified by flash column chromatography to afford 17A (pale yellow liquid, 220 mg, 0.555 mmol, 31.7% yield) LC-MS Anal. Calc'd for $C_{18}H_{19}BrClNO_2$ 396.7. found [M−H] 395.9, $T_r$=1.76 min (Method AY).

17B. methyl 3-(3-((4-chlorophenyl)amino)-4-(3,5-dimethylisoxazol-4-yl)phenyl)pentanoate (Absolute Stereochemistry not Determined)

17A (20 mg, 0.050 mmol), potassium phosphate tribasic (21.40 mg, 0.101 mmol) and (3,5-dimethylisoxazol-4-yl)boronic acid (14.21 mg; 0.101 mmol) were taken in a microwave vial. Tetrahydrofuran (0.9 mL) and water (0.1 mL) were added and the nitrogen was bubbled through this mixture for 10 minutes. 2-(dicyclohexylphosphino)-2',4',6'-triisopropylbiphenyl (4.81 mg, 10.08 μmol) and chloro(2-dicyclohexylphosphino-2',4',6'-triisopropyl-1,1'-biphenyl)[2-(2'-amino-1,1'-biphenyl)]Palladium(II) (3.97 mg, 5.04 μmol) were added and the reaction mixture was irradiated with microwave radiation at 85° C. for 1 h. LCMS indicated the desired mass of the product 17B. LC-MS Anal. Calc'd for $C_{23}H_{25}ClN_2O_3$ 412.9. found [M+H] 413.2, $T_r$=12.8 min (Method AU). The crude was taken next step without further purification.

Example 17. (R)-3-(3-((4-chlorophenyl)amino)-4-(3,5-dimethylisoxazol-4-yl)phenyl)pentanoic Acid (Absolute Stereochemistry not Determined)

Example 17 was prepared from 17B following the procedure described for the synthesis of Example 2. LC-MS Anal. Calc'd for $C_{22}H_{23}ClN_2O_3$ 398.88. found [M+H] 399.2, $T_r$=1.98 min (Method R). $^1$H NMR (400 MHz, DMSO-$d_6$) δ 12.02 (br. s., 1H), 7.59 (s, 1H), 7.09-7.17 (m, 4H), 6.91-6.96 (m, 1H), 6.83 (d, J=9.04 Hz, 2H), 2.87 (t, J=6.27 Hz, 1H), 2.55-2.63 (m, 1H), 2.42-2.47 (m, 1H), 2.19 (s, 3H) 2.00 (s, 3H), 1.60-1.69 (m, 1H), 1.53-1.57 (m, 1H), 0.77 (t, J=7.28 Hz, 3H).

Example 18

Homochiral

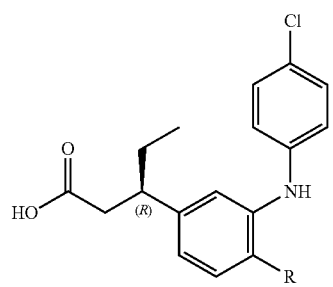

Example 18 was prepared from 17A and (1H-pyrazol-4-yl)boronic acid following the procedure described for the synthesis of Example 17.

| Ex. No. | Name | R | Tr min | Method | (M + H) |
|---|---|---|---|---|---|
| 18 | (R)-3-(3-((4-chlorophenyl)amino)-4-(1H-pyrazol-4-yl)phenyl)pentanoic acid (absolute stereochemistry not determined) | 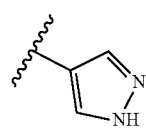 [SMILES: *c1cn[nH]c1] | 1.36 | O | 370.2 |

Example 19

Homochiral (R)-3-(3-((4-chlorophenyl)amino)-4-(4-methylthiazol-2-yl)phenyl)pentanoic Acid (Absolute Stereochemistry not Determined)

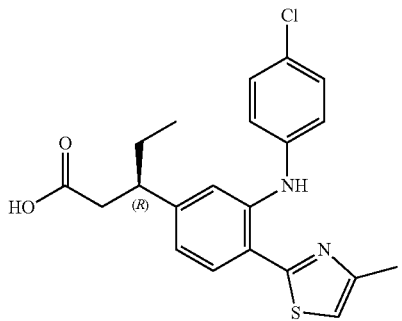

19A. methyl 3-(3-((4-chlorophenyl)amino)-4-(5,5-dimethyl-1,3,2-dioxaborinan-2-yl)phenyl)pentanoate (Absolute Stereochemistry not Determined)

A mixture of 17A (250 mg, 0.630 mmol), bis(neopentyl glycolato)diboron (185 mg, 0.819 mmol) and potassium acetate (186 mg, 1.891 mmol) in dioxane (8 mL) at room temperature in a sealable flask was purged with argon for 20 minutes before PdCl$_2$(dppf)-CH$_2$Cl$_2$ Adduct (15.44 mg, 0.019 mmol) was added. The flask was sealed and the reaction was heated at 80° C. for 6 h. The reaction mixture was cooled to room temperature and poured into water (25 mL), extracted with EtOAc (2×50 mL). The combined organic layer was washed with brine (2×10 mL), dried over anhydrous sodium sulfate, filtered and concentrated under reduced pressure. The crude sample was purified by flash silica gel chromatography to afford 19A (pale yellow liquid, 220 mg, 0.512 mmol, 81% yield). LC-MS Anal. Calc'd for $C_{23}H_{29}BClNO_4$ 429.74. found [M+H] 399.2 for parent boronic acid, $T_r$=1.98 min (Method AU).

19B. methyl 3-(3-((4-chlorophenyl)amino)-4-(4-methylthiazol-2-yl)phenyl)pentanoate (Absolute Stereochemistry not Determined)

19A (20 mg, 0.047 mmol), potassium phosphate tribasic (19.76 mg, 0.093 mmol) and 2-bromo-4-methylthiazole (9.94 mg; 0.056 mmol) were taken in a microwave vial. Tetrahydrofuran (0.9 mL) and Water (0.1 mL) were added and nitrogen was bubbled through the reaction mixture for 10 minutes. 2-(dicyclohexylphosphino)-2',4',6'-triisopropylbiphenyl (4.44 mg, 9.31 µmol) and chloro(2-dicyclohexylphosphino-2',4',6'-triisopropyl-1,1'-biphenyl)[2-(2'-amino-1,1'-biphenyl)]Palladium(II) (3.66 mg, 4.65 µmol) were then added and the reaction mixture was irradiated with microwave radiation at 85° C. for 1 hr. LCMS indicated the desired mass of the product 19B. LC-MS Anal. Calc'd for $C_{22}H_{23}ClN_2O_2S$ 414.9. found [M+H] 415.2 $T_r$=4.026 min (Method R). The crude compound was taken to next step without further purification.

Example 19. (R)-3-(3-((4-chlorophenyl)amino)-4-(4-methylthiazol-2-yl)phenyl)pentanoic Acid (Absolute Stereochemistry not Determined)

Example 19 was prepared from 19B following the procedure described for the synthesis of Example 2. LC-MS Anal. Calc'd for $C_{21}H_{21}ClN_2O_2S$ 400.1. found [M+H] 401.1, $T_r$=2.12 min (Method R). $^1H$ NMR (400 MHz, DMSO-$d_6$) δ 12.02 (s, 1H) 10.10 (s, 1H) 7.76 (d, J=8.0 Hz, 1H) 7.29-7.35 (m, 2H) 7.27 (d, J=1.00 Hz, 1H) 7.17 (d, J=1.50 Hz, 1H) 7.09-7.14 (m, 2H) 6.83-6.89 (m, 1H) 2.81-2.90 (m, 1H) 2.54-2.62 (m, 2H) 2.40 (s, 3H) 1.58-1.68 (m, 1H) 1.47-1.58 (m, 1H) 0.75 (t, J=7.28 Hz, 3H).

Example 20-22

Homochiral

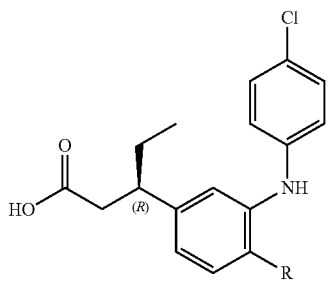

Examples 20-22 was prepared from 17A and corresponding heteroaryl bromides following the procedure described for the synthesis of Example 19.

Example 23

Homochiral (R)-3-(3-(3-(4-chloro-2-fluorophenyl)ureido)-4-(1-methyl-1H-pyrazol-4-yl)phenyl)pentanoic Acid (Absolute Stereochemistry not Determined)

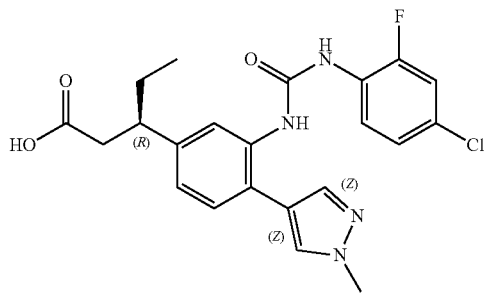

23A. methyl 3-(3-(3-(4-chloro-2-fluorophenyl)ureido)-4-(1-methyl-1H-pyrazol-4-yl)phenyl)pentanoate (Absolute Stereochemistry not Determined)

To a stirred solution of 2D (40 mg, 0.139 mmol) in THF (1.5 mL) was added 4-chloro-2-fluoro-1-isocyanatobenzene (28.7 mg, 0.167 mmol) under nitrogen atmosphere and stirred at room temperature for 3 h. LCMS indicated completion of reaction. The reaction mixture was concentrated under reduced pressure to obtain 23A (pale yellow liquid, 35 mg, 0.076 mmol, 55% yield). The crude compound was taken to next step without further purification. LC-MS Anal. Calc'd $C_{23}H_{24}ClFN_4O_3$ 458.9. found [M+H] 459.1, $T_r$=1.37 min (Method AY).

| Ex. No. | Name | R | Tr min | Method | (M + H) |
| --- | --- | --- | --- | --- | --- |
| 20 | (R)-3-(3-((4-chlorophenyl)amino)-4-(4-phenylthiazol-2-yl)phenyl)pentanoic acid (absolute stereochemistry not determined) | | 2.54 | O | 463.2 |
| 21 | (R)-3-(3-((4-chlorophenyl)amino)-4-(thiazol-2-yl)phenyl)pentanoic acid (absolute stereochemistry not determined) | | 2.32 | O | 387.1 |
| 22 | (R)-3-(3-((4-chlorophenyl)amino)-4-(5-methyl-1,3,4-thiadiazol-2-yl)phenyl)pentanoic acid (absolute stereochemistry not determined) | | 1.69 | O | 402.1 |

Example 23. (R)-3-(3-(3-(4-chloro-2-fluorophenyl)ureido)-4-(1-methyl-1H-pyrazol-4-yl)phenyl)pentanoic Acid (Absolute Stereochemistry not Determined)

Example 23 was prepared from 23A following the procedure described for the synthesis of Example 2. LC-MS Anal. Calc'd for $C_{22}H_{22}ClFN_4O_3$ 444.1. found [M+H] 445.11, $T_r$=1.42 min (Method O). 1H NMR (400 MHz, DMSO-$d_6$) δ 8.07 (t, J=8.80 Hz, 1H), 7.80 (s, 1H), 7.64-7.66 (m, 2H), 7.32 (d, J=7.60 Hz, 1H), 7.23 (did, J=10.80, 2.40 Hz, 1H), 7.14-7.17 (m, 1H), 7.05-7.07 (m, 1H), 3.96 (s, 3H), 3.00-3.03 (m, 1H), 2.56-2.70 (m, 2H), 1.76-1.81 (m, 1H), 1.66-1.71 (m, 1H), 0.87 (t, J=7.20 Hz, 3H).

Example 24

Homochiral (R)-3-(3-(3-(4-chloro-2-fluorophenyl)ureido)-4-(1-isopropyl-1H-pyrazol-4-yl)phenyl)pentanoic Acid (Absolute Stereochemistry not Determined)

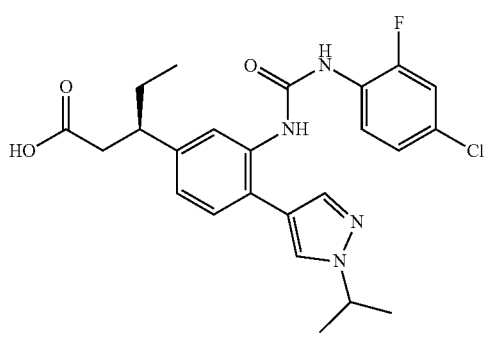 [SMILES: CC[C@H](CC(=O)O)c1ccc(-c2cnn(C(C)C)c2)c(NC(=O)Nc2ccc(Cl)cc2F)c1]

24A. methyl 3-(3-amino-4-(1-isopropyl-1H-pyrazol-4-yl)phenyl)pentanoate (Absolute Stereochemistry not Determined)

To a stirred solution of 2C Enantiomer 1 (50 mg, 0.175 mmol) in a mixture DME (2 mL) and Water (2 mL) was added 1-isopropyl-4-(4,4,5,5-tetramethyl-1,3,2-dioxaborolan-2-yl)-1H-pyrazole (49.5 mg, 0.210 mmol), $K_2CO_3$ (24.15 mg, 0.175 mmol) and purged with argon for 10 min. To the above reaction mixture tetrakis(triphenylphosphine)palladium(0) (10.10 mg, 8.74 µmol) was added and purged with argon for another 10 min. The reaction mixture was stirred at 110° C. for 16 h. The reaction mixture was cooled to room temperature and poured into water (15 mL), extracted with EtOAc (2×15 mL). The combined organic layer was washed with brine (1×10 mL), dried over anhydrous sodium sulfate, filtered and concentrated under reduced pressure to obtain 24A (pale brown liquid, 44 mg, 0.142 mmol, 81% yield). The crude product was taken to next step without further purification. LC-MS Anal. Calc'd for $C_{18}H_{25}N_3O_2$ 315.41. found [M+H] 316.2, $T_r$=1.25 min (Method AY).

24B. methyl 3-(3-(3-(4-chloro-2-fluorophenyl)ureido)-4-(1-isopropyl-1H-pyrazol-4-yl)phenyl)pentanoate (Absolute Stereochemistry not Determined)

To a stirred solution of 24A (45 mg, 0.143 mmol) in THF (1.5 mL) was added 4-chloro-2-fluoro-1-isocyanatobenzene (29.4 mg, 0.171 mmol) under nitrogen atmosphere and stirred at room temperature for 3 h. LCMS indicated completion of reaction. The reaction mixture was concentrated under reduced pressure to obtain 24B (pale yellow liquid, 35 mg, 0.072 mmol, 50% yield). The crude compound was taken to next step without further purification. LC-MS Anal. Calc'd for $C_{25}H_{28}ClFN_4O_3$ 486.1. found [M+H] 487.2, $T_r$=1.48 min (Method AY).

Example 24. (R)-3-(3-(3-(4-chloro-2-fluorophenyl)ureido)-4-(1-isopropyl-1H-pyrazol-4-yl)phenyl)pentanoic Acid (Absolute Stereochemistry not Determined)

Example 24 was prepared from 24B following the procedure described for the synthesis of Example 101. LC-MS Anal. Calc'd for $C_{24}H_{26}ClFN_4O_3$ 472.2. found [M+H] 473.1, $T_r$=1.64 min (Method O). $^1$H NMR (400 MHz, MeOD) δ 8.02-8.04 (m, 1H), 7.87 (s, 1H), 7.69 (s, 1H), 7.56 (d, J=1.60 Hz, 1H), 7.35 (d, J=8.00 Hz, 1H), 7.23 (dd, J=10.80, 2.40 Hz, 1H), 7.14-7.17 (m, 1H), 7.09 (dd, J=8.00, 1.60 Hz, 1H), 4.54-4.61 (m, 2H), 2.99-3.02 (m, 1H), 2.57-2.71 (m, 1H), 1.77-1.79 (m, 1H), 1.67-1.70 (m, 1H), 1.53 (d, J=6.80 Hz, 6H), 0.87 (t, J=7.20 Hz, 3H).

Examples 25 and 26

Enantiomer 1 and Enantiomer 2

(R)-3-(4-(1-(tert-butoxycarbonyl)piperidin-4-yl)-3-((2-ethoxypyrimidin-5-yl)amino)phenyl)pentanoic Acid (S)-3-(4-(1-(tert-butoxycarbonyl)piperidin-4-yl)-3-((2-ethoxypyrimidin-5-yl)amino)phenyl)pentanoic Acid (Absolute Stereochemistry not Determined)

Enantiomer 1

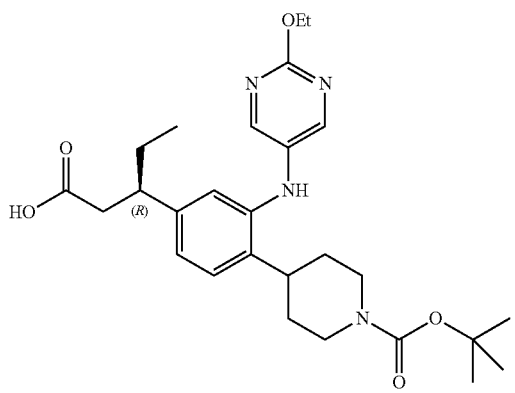

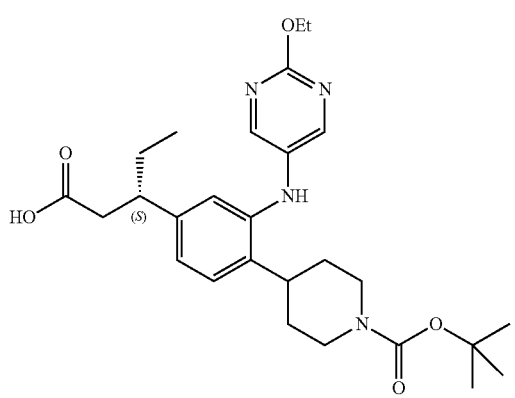

25A. tert-butyl 4-(2-((2-ethoxypyrimidin-5-yl) amino)-4-(1-methoxy-1-oxopentan-3-yl)phenyl)-3,6-dihydropyridine-1(2H)-carboxylate (Absolute Stereochemistry not Determined)

To a stirred solution of tert-butyl 4-(4,4,5,5-tetramethyl-1,3,2-dioxaborolan-2-yl)-5,6-dihydropyridine-1(2H)-carboxylate (83 mg, 0.269 mmol), (methyl 3-(4-bromo-3-((2-ethoxypyrimidin-5-yl)amino)phenyl)pentanoate) (100 mg, 0.245 mmol), which was prepared from 2C Enantiomer 1 and 5-bromo-2-ethoxypyrimidine following the procedure described for the synthesis of 17A, in DME (4 ml) and Ethanol (1 mL) was added $Na_2CO_3$ (57.1 mg, 0.539 mmol). The reaction mixture was purged with nitrogen for 10 mints. Then $Pd(Ph_3P)_4$ (14.15 mg, 0.012 mmol) was added under inert atmosphere, followed by purging with nitrogen for another 5 min. The reaction mixture was heated and stirred at 100° C. for 16 h in a sealed vial. The reaction mixture was evaporated under reduced pressure and diluted with ethyl acetate (25 mL). Organic layer was washed with water (lx 10 mL), brine (2×10 mL), dried over $Na_2SO_4$, filtered and evaporated under reduced pressure to afford the residue which was purified by flash silica gel chromatography to afford 25A (light brown solid, 98 mg, 0.125 mmol, 50.9% yield). LC-MS Anal. Calc'd for $C_{28}H_{38}N_4O_5$, 510.64. found [M+H] 511.2, $T_r$=3.708 min (Method N).

25B. tert-butyl 4-(2-((2-ethoxypyrimidin-5-yl) amino)-4-(1-methoxy-1-oxopentan-3-yl)phenyl)piperidine-1-carboxylate (Absolute Stereochemistry not Determined)

To a degassed solution of 25A (75 mg, 0.147 mmol) in Ethanol (10 mL) was added 10% w/w palladium on carbon (15.63 mg, 0.015 mmol). Then the reaction mixture was evacuated, purged with nitrogen and stirred under hydrogen atmosphere in a bladder for 4 h at room temperature. The reaction mixture was filtered through Celite bed which was washed with Ethanol (3×15 mL). The combined organic solvents were evaporated under reduced pressure to afford 25B (Light brown solid, 68 mg, 0.107 mmol, 73.2% yield). LC-MS Anal. Calc'd for $C_{28}H_{40}N_4O_5$, 512.65. found [M+H] 513.2, $T_r$=3.612 min (Method N).

Example 25 Enantiomer 1. (R)-3-(4-(1-(tert-butoxycarbonyl)piperidin-4-yl)-3-((2-ethoxypyrimidin-5-yl)amino)phenyl)pentanoic Acid (Absolute Stereochemistry not Determined)

To a stirring solution of 25B (25 mg, 0.049 mmol) in mixture of THF (0.5 mL), Methanol (1 mL) and Water (0.25 mL) was added LiOH (17.52 mg, 0.732 mmol) and stirred at room temperature for 16 h. The organic solvents were evaporated under reduced pressure. Aqueous solution was acidified to pH~4 with saturated citric acid solution and extracted with ethyl acetate (2×10 mL). The combined organic layer was washed with water (10 mL), brine (10 mL), dried over anhydrous sodium sulfate, filtered and evaporated under reduced pressure to afford the crude material which was purified via preparative LCMS to afford Example 25 Enantiomer 1 (pale yellow solid, 14.6 mg, 0.029 mmol, 59.4% yield). LC-MS Anal. Calc'd for $C_{27}H_{38}N_4O_5$, 498.62. found [M+H] 499.3, $T_r$ 1.959 min (Method O). $^1$H NMR (400 MHz, DMSO-$d_6$) δ 8.19 (s, 2H), 7.29 (s, 1H), 7.13 (d, J=8.4 Hz, 1H), 6.81 (s, 1H), 6.79 (brs, 1H), 4.26 (q, J=7.2 Hz, 2H), 4.06-4.03 (m, 2H), 2.96 (m, 1H), 2.78-2.72 (m, 3H), 1.71-1.68 (m, 2H), 1.56-1.54 (m, 1H), 1.47-1.42 (m, 1H), 1.40 (s, 9H), 1.30 (t, J=7.0 Hz, 3H), 0.77 (t, J=7.0 Hz, 3H), (2H signal is buried under solvent peak).

Example 26

Enantiomer 2

(S)-3-(4-(1-(tert-butoxycarbonyl)piperidin-4-yl)-3-((2-ethoxypyrimidin-5-yl)amino)phenyl)pentanoic Acid (Absolute Stereochemistry not Determined)

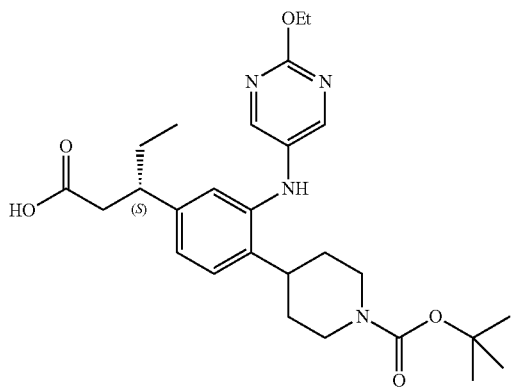

26A. methyl 3-(4-bromo-3-((2-ethoxypyrimidin-5-yl) amino) phenyl) pentanoate (Absolute Stereochemistry not Determined)

26A was synthesized from 2C Enantiomer 2 and 5-bromo-2-ethoxypyrimidine following the procedure described for the synthesis of 17A. LC-MS Anal. Calc'd for $C_{18}H_{22}BrN_3O_3$, 407.084. found [M+H] 408.3, $T_r$=1.42 min (Method AY).

26B. tert-butyl 4-(2-((2-ethoxypyrimidin-5-yl) amino)-4-(1-methoxy-1-oxopentan-3-yl)phenyl)-3,6-dihydropyridine-1(2H)-carboxylate (Absolute Stereochemistry not Determined)

26B was synthesized from 26A following the procedure described for the synthesis of 26A. LC-MS Anal. Calc'd for $C_{28}H_{38}N_4O_5$, 510.284. found [M+H] 511.2, $T_r$=3.651 min (Method N).

26C. tert-butyl 4-(2-((2-ethoxypyrimidin-5-yl)amino)-4-(1-methoxy-1-oxopentan-3-yl)phenyl)piperidine-1-carboxylate (Absolute Stereochemistry not Determined)

26C was synthesized from 26B following the procedure described for the synthesis of 25B. LC-MS Anal. Calc'd for $C_{28}H_{40}N_4O_5$, 512.641. found [M+H] 513.2, $T_r$=3.694 min (Method N).

Example 26 Enantiomer 2. (S)-3-(4-(1-(tert-butoxycarbonyl)piperidin-4-yl)-3-((2-ethoxypyrimidin-5-yl)amino)phenyl)pentanoic Acid (Absolute Stereochemistry not Determined)

Example 26 Enantiomer 2 was synthesized from 26C following the procedure described for the synthesis of Example 25 Enantiomer 1. LC-MS Anal. Calc'd for $C_{27}H_{38}N_4O_5$, 498.614. found [M+H] 499.3, $T_r$=1.958 min (Method O). $^1$H NMR (400 MHz, DMSO-$d_6$) δ 8.19 (s, 2H), 7.29 (s, 1H), 7.13 (d, J 8.4 Hz, 1H), 6.81 (s, 1H), 6.79 (brs, 1H), 4.26 (q, J=7.2 Hz, 2H), 4.06-4.03 (m, 2H), 2.96 (m, 1H), 2.78-2.72 (m, 3H), 1.71-1.68 (m, 2H), 1.56-1.54 (m, 1H), 1.47-1.42 (m, 1H), 1.40 (s, 9H), 1.30 (t, J=7.0 Hz, 3H), 0.77 (t, J=7.0 Hz, 3H), (2H signal buried in solvent peak).

Example 27 and 28

Enantiomer 1 and Enantiomer 2

(R)-3-(4-(1-(tert-butoxycarbonyl)piperidin-4-yl)-3-((2-methylpyrimidin-5-yl)amino)phenyl)pentanoic Acid (S)-3-(4-(1-(tert-butoxycarbonyl)piperidin-4-yl)-3-((2-methylpyrimidin-5-yl)amino)phenyl)pentanoic Acid Enantiomer 1

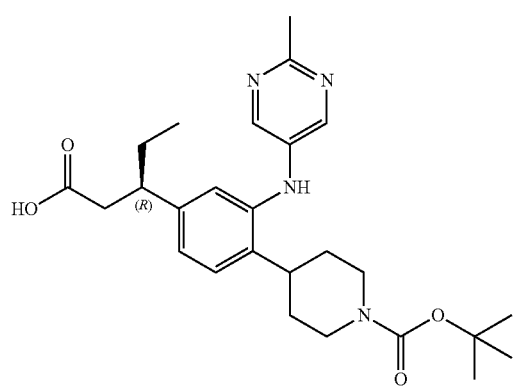

Enantiomer 2

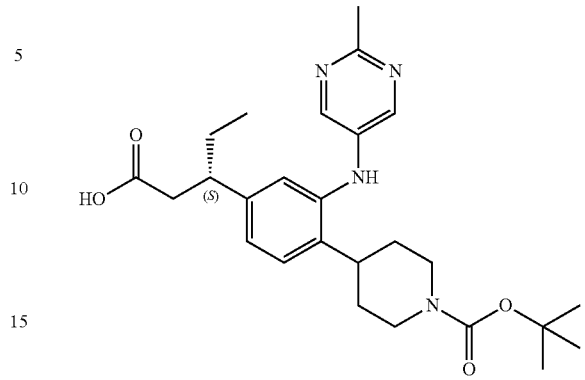

27A. tert-butyl 4-(4-(1-methoxy-1-oxopentan-3-yl)-2-nitrophenyl)-3,6-dihydropyridine-1(2H)-carboxylate (Absolute Stereochemistry not Determined)

To a stirred solution of tert-butyl 4-(4,4,5,5-tetramethyl-1,3,2-dioxaborolan-2-yl)-5,6-dihydropyridine-1(2H)-carboxylate (538 mg, 1.740 mmol), 2B (methyl 3-(4-bromo-3-nitrophenyl)pentanoate) (500 mg, 1.582 mmol) in DME (4.00 mL) and Ethanol (1 mL) was added $Na_2CO_3$ (369 mg, 3.48 mmol). The reaction mixture was purged with Nitrogen for 10 min. Then added Pd(Ph$_3$P)4 (91 mg, 0.079 mmol) under inert atmosphere and was purged with nitrogen for another 5 min. The reaction mixture was stirred and heated at 100° C. for 16 h. The reaction mixture was evaporated under reduced pressure to the dryness and diluted with ethyl acetate (125 mL). The organic layer was washed with water (1x 100 mL), brine (2×100 mL), dried over $Na_2SO_4$, filtered, and evaporated under reduced pressure to afford the crude sample which was purified by flash silica gel chromatography to afford 27A (550 mg, 1.314 mmol, 83% yield). LC-MS Anal. Calc'd for $C_{22}H_{30}N_2O_6$, 418.483. found [M−54] 363.2, $T_r$=2.633 min (Method CP).

27B. tert-butyl 4-(2-amino-4-(1-methoxy-1-oxopentan-3-yl)phenyl)piperidine-1-carboxylate (Absolute Stereochemistry not Determined)

To a degassed solution of 27A (550 mg, 1.314 mmol) in Ethanol (10 mL) was added 10% w/w palladium on carbon (280 mg, 0.263 mmol). Then the reaction mixture was evacuated, purged with nitrogen and stirred under hydrogen atmosphere at 50 psi for 4 h at room temperature. The reaction mixture was filtered through celite bed which was washed with Ethanol (3×50 mL). The combined organic solvents were evaporated under reduced pressure to afford the 27B (appearance, 325 mg, 0.832 mmol, 63.3% yield). LC-MS Anal. Calc'd for $C_{22}H_{34}N_2O_4$, 390.516. found [M+H] 391.2, $T_r$=3.357 min (Method N).

Chiral SFC separation shown chiral purity of 100% for 27B Enantiomer 1, $T_r$=8.04 min in comparison to 27B Enantiomer 2, $T_r$=5.44 min (Method ED).

27C. tert-butyl 4-(4-(1-methoxy-1-oxopentan-3-yl)-2-((2-methylpyrimidin-5-yl)amino) phenyl)piperidine-1-carboxylate (Absolute Stereochemistry not Determined)

To a stirred solution of 27B Enantiomer 1 (50 mg, 0.128 mmol) in Dioxane (2 mL) was added 5-bromo-2-methylpyrimidine (33.2 mg, 0.192 mmol), Xantphos (14.82 mg, 0.026 mmol), cesium carbonate (125 mg, 0.384 mmol) and purged with nitrogen gas for 10 min. Then bis(dibenzylideneacetone)palladium (7.36 mg, 0.013 mmol) was added and the reaction mixture was purged with nitrogen gas for another 5 min. The reaction mixture was stirred and heated at 110° C. for 6 h in a sealed tube. Then the reaction mixture was evaporated to dryness and diluted with ethyl acetate (25 mL). The organic layer was washed with water (1×10 mL), brine (2×10 mL), dried over $Na_2SO_4$, filtered, and evaporated under reduced pressure to give the crude material which was purified by flash silica gel chromatography to afford 27C (45 mg, 0.089 mmol, 69.2% yield). LC-MS Anal. Calc'd for $C_{27}H_{38}N_4O_4$, 482.289. found [M+H] 483.5, $T_r$=1.43 min (Method AY).

Example 27 Enantiomer 1. (R)-3-(4-(1-(tert-butoxycarbonyl)piperidin-4-yl)-3-((2-methylpyrimidin-5-yl)amino)phenyl)pentanoic Acid (Absolute Stereochemistry not Determined)

To a stirring solution of 27C (45 mg, 0.093 mmol) in mixture of THF (0.5 mL), Methanol (1 mL) and Water (0.25 mL) was added LiOH (33.5 mg, 1.399 mmol) and stirred at room temperature for 16 h. The organic solvents were evaporated under reduced pressure; aqueous solution was acidified to pH~3-4 with saturated citric acid solution, and extracted with ethyl acetate (2×10 mL). The combined organic layer was washed with water (10 mL), brine (10 mL), dried over anhydrous sodium sulfate, filtered and evaporated under reduced pressure to afford the crude material, which was purified via preparative LCMS to afford Example 27 Enantiomer 1 (pale yellow solid, 21 mg, 0.044 mmol, 47.6% yield). LC-MS Anal. Calc'd for $C_{26}H_{36}N_4O_4$, 468.588. found [M+H] 469.3, $T_r$=1.414 min (Method O). $^1$H NMR (400 MHz, DMSO-$d_6$) δ 8.19 (s, 2H), 7.60 (s, 1H), 7.20 (d, J 8.4 Hz, 1H), 6.97 (s, 1H), 6.92 (d, J 8 Hz, 1H), 4.05 (m, 2H), 2.96 (m, 1H), 2.80-2.53 (m, 2H), 2.50 (s, 3H), 2.42 (m, 1H), 1.64 (m, 2H), 1.47 (m, 2H), 1.43 (s, 9H), 0.70 (t, J 7.6 Hz), (one $CH_2$ proton buried in solvent peak).

Example 29-30 Enantiomer 1

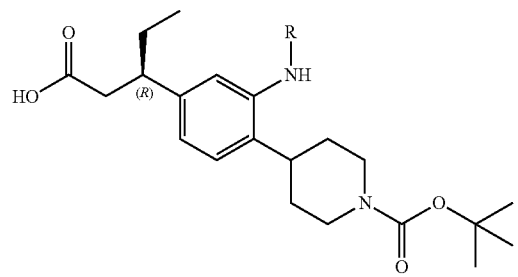

Examples 151-152 Enantiomer 1 were prepared from 150B Enantiomer 1 and corresponding aryl/heteroaryl halides following the procedure described for the synthesis of Example 150 Enantiomer 1

| Ex. No. | Name | R | $T_R$ (min) | $[M + H]^+$ |
|---|---|---|---|---|
| 29 | (R)-3-(4-(1-(tert-butoxycarbonyl)piperidin-4-yl)-3-((2-ethylpyrimidin-5-yl)amino)phenyl)pentanoic acid (absolute stereochemistry not determined) | | 1.524 Method O | 483.4 |
| 30 | (R)-3-(4-(1-(tert-butoxycarbonyl)piperidin-4-yl)-3-((4-cyanophenyl)amino)phenyl)pentanoic acid (absolute stereochemistry not determined) | CN | 1.717 Method O | 478.3 |

Example 28

(S)-3-(4-(1-(tert-butoxycarbonyl)piperidin-4-yl)-3-((2-methylpyrimidin-5-yl)amino)phenyl)pentanoic Acid (Absolute Stereochemistry not Determined)

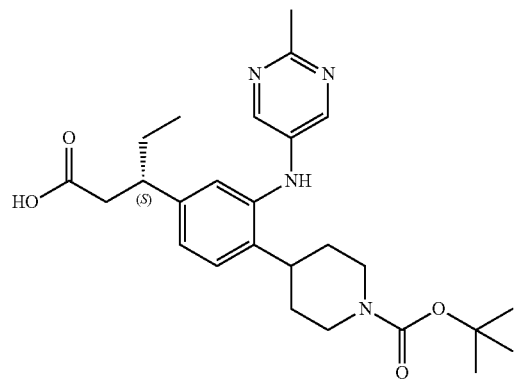

28A. tert-butyl 4-(2-amino-4-(1-methoxy-1-oxopentan-3-yl)phenyl)-3,6-dihydropyridine-1(2H)-carboxylate (Absolute Stereochemistry not Determined)

To a stirred solution of tert-butyl 4-(4,4,5,5-tetramethyl-1,3,2-dioxaborolan-2-yl)-5,6-dihydropyridine-1(2H)-carboxylate (713 mg, 2.306 mmol), 2C (methyl 3-(3-amino-4-bromophenyl)pentanoate) (600 mg, 2.097 mmol) in DME (4.00 mL) and Ethanol (1 ml) was added $Na_2CO_3$ (489 mg, 4.61 mmol). The reaction mixture was purged with Nitrogen for 10 min. Then added $Pd(Ph_3P)4$ (121 mg, 0.105 mmol) under inert atmosphere, purged with nitrogen for another 5 min, stirred and heated at 100° C. for 16 h. The reaction mixture was evaporated under reduced pressure to the dryness, and diluted with ethyl acetate (125 mL). The organic layer was washed with water (1x 100 mL), Brine (2×100 mL), dried over $Na_2SO_4$, filtered, and evaporated under reduced pressure to give the crude material, which was purified by flash silica gel chromatography to afford 28A (275 mg, 0.680 mmol, 32.4% yield). LC-MS Anal. Calc'd for $C_{22}H_{32}N_2O_4$, 388.51. found [M+H] 389.0, $T_r$=2.603 min (Method CP).

28B. tert-butyl 4-(2-amino-4-(1-methoxy-1-oxopentan-3-yl)phenyl)piperidine-1-carboxylate (Absolute Stereochemistry not Determined)

To a degassed solution of 28A (250 mg, 0.643 mmol) in Ethanol (10 mL) was added 10% w/w palladium on carbon (68.5 mg, 0.064 mmol). Then the reaction mixture was evacuated, purged with nitrogen and stirred under hydrogen atmosphere at 50 psi for 4h at room temperature. The reaction mass was filtered through celite bed, washed the celite bed with Ethanol (3×50 mL). The combined organic solvents were evaporated under reduced pressure to afford 28B (175 mg, 0.448 mmol, 69.6% yield). LC-MS Anal. Calc'd for $C_{22}H_{34}N_2O_4$, 390.516. found [M+H] 392.2, $T_r$=3.676 min (Method N).

Chiral SFC separation shown chiral purity of 100% for 28B Enantiomer 2, $T_r$=5.44 min in comparison to 27B Enantiomer 1, $T_r$=8.04 min (Method ED).

28C. tert-butyl 4-(4-(1-methoxy-1-oxopentan-3-yl)-2-((2-methylpyrimidin-5-yl)amino)phenyl)piperidine-1-carboxylate (Absolute Stereochemistry not Determined)

To a stirred solution of 28B Enantiomer 2 (50 mg, 0.128 mmol) in Dioxane (2 mL) was added 5-bromo-2-methylpyrimidine (33.2 mg, 0.192 mmol), Xantphos (14.82 mg, 0.026 mmol), cesium carbonate (125 mg, 0.384 mmol) and purged with nitrogen gas for 10 min. Then added bis(dibenzylideneacetone)palladium (7.36 mg, 0.013 mmol), purged with nitrogen gas for another 5 min. The reaction mixture was stirred and heated at 110° C. for 6 h in a sealed tube. Then the reaction mixture was evaporated to dryness and diluted with ethyl acetate (25 mL). The organic layer was washed with water (1x 10 mL), Brine (2×10 mL), dried over $Na_2SO_4$, filtered, and evaporated under reduced pressure to give the crude material, which was purified by flash silica gel chromatography to afford 28C (84 mg, 0.080 mmol, 62.5% yield). LC-MS Anal. Calc'd for $C_{27}H_{38}N_4O_4$, 482.289. found [M+H] 483.2, $T_r$=2.981 min (Method CP).

Example 28 (S)-3-(4-(1-(tert-butoxycarbonyl)piperidin-4-yl)-3-((2-methylpyrimidin-5-yl)amino)phenyl)pentanoic Acid (Absolute Stereochemistry not Determined)

To a stirring solution of 28C (84 mg, 0.080 mmol) in mixture of THF (0.5 mL), Methanol (1 mL) and Water (0.25 mL) was added LiOH (28.8 mg, 1.201 mmol) and stirred at room temperature for 16 h. The organic solvents were evaporated under reduced pressure; aqueous solution was acidified to pH~3-4 with saturated citric acid solution, and extracted with ethyl acetate (2×10 mL). The combined organic layer was washed with water (10 mL), brine (10 mL), dried over anhydrous sodium sulfate, filtered and evaporated under reduced pressure to afford the crude material, which was purified via preparative LCMS to afford Example 28 (pale yellow solid, 2.1 mg, 4.35 µmol, 5.43% yield). LC-MS Anal. Calc'd for $C_{26}H_{36}N_4O_4$, 468.588. found [M+H] 469.2, $T_r$=1.585 min (Method O). $^1$H NMR (400 MHz, DMSO-$d_6$) δ 8.18 (s, 2H), 7.60 (s, 1H), 7.19 (d, J 8.4 Hz, 1H), 6.97 (s, 1H), 6.92 (d, J 8 Hz, 1H), 4.05 (m, 2H), 3.16 (m, 2H), 2.95 (m, 1H), 2.78-2.53 (m, 2H), 2.49 (s, 3H), 2.42 (m, 1H), 1.65 (m, 2H), 1.46 (m, 2H), 1.41 (s, 9H), 0.70 (t, J 7.6 Hz).

Example 31-32

Enantiomer 2

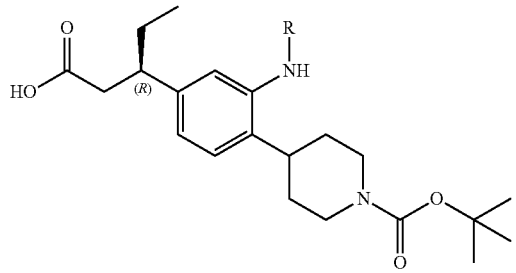

Examples 31-32 were prepared from 28B and corresponding aryl/heteroaryl halides following the procedure described for the synthesis of Example 28.

| Ex. No. | Name | R | $T_R$ (min) | [M + H]$^+$ |
|---|---|---|---|---|
| 31 | (S)-3-(4-(1-(tert-butoxycarbonyl) piperidin-4-yl)-3-((2-ethylpyrimidin-5-yl)amino)phenyl) pentanoic acid (absolute stereochemistry not determined) | 2-ethylpyrimidin-5-yl | 1.714 Method O | 483.2 |
| 32 | (S)-3-(4-(1-(tert-butoxycarbonyl) piperidin-4-yl)-3-((4-cyanophenyl)amino) phenyl)pentanoic acid (absolute stereochemistry not determined) | 4-CN-phenyl | 1.958 Method O | 378.1 (M-100); for Boc deprotected compound |

Example 33

(S)-3-(3-((4-cyanophenyl) amino)-4-(1-methyl-1H-pyrazol-4-yl) phenyl)-4-methoxybutanoic Acid (R)-3-(3-((4-cyanophenyl) amino)-4-(1-methyl-1H-pyrazol-4-yl) phenyl)-4-methoxybutanoic Acid (Absolute Stereochemistry not Determined)

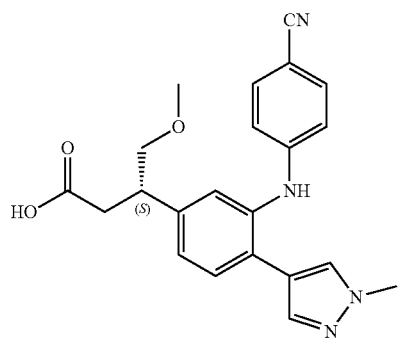

-continued

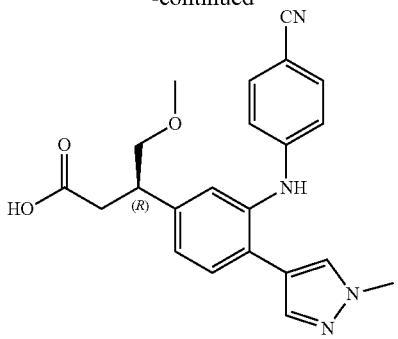

33A. (2-((4-bromo-2-nitrophenoxy)methoxy)ethyl) trimethylsilane

To a stirred solution of 4-bromo-2-nitrophenol (12 g, 55.0 mmol) and DIPEA (19.23 mL, 110 mmol) in DCM (120 mL), was added (2-(chloromethoxy)ethyl)trimethylsilane (11.01 g, 66.1 mmol) at 0° C. Then the reaction mixture was stirred at room temperature for 6 h. The reaction mixture was diluted with dichloro methane (200 mL), washed with saturated aqueous ammonium chloride solution (200 mL), dried over sodium sulphate, filtered and concentrated under reduced pressure to afford 33A (yellow oil, 16 g, 45.9 mmol, 83% yield). LC-MS Anal. Calc'd for $C_{12}H_{18}BrNO_4Si$ 347.019. found [M+NH4] 365.2, $T_r$=3.891 min (Method N).

33B. (2-((4-(5,5-dimethyl-1,3,2-dioxaborinan-2-yl)-2-nitrophenoxy)methoxy)ethyl) trimethylsilane To a stirred solution of 33A (15 g, 43.1 mmol), 5,5,5',5'-tetramethyl-2,2'-bi(1,3,2-dioxaborinane) (11.67 g, 51.7 mmol), potassium acetate (12.68 g, 129 mmol) in dioxane (120 mL), argon gas was bubbled for 5 min at room temperature. To this $PdCl_2(dppf)-CH_2Cl_2$ adduct (1.759 g, 2.154 mmol) was added and the argon gas was bubbled for another 5 min. Then the reaction mixture was heated at 90° C. for 6 h in a sealed vessel. The reaction mixture was allowed to cool to room temperature, filtered through celite pad and washed with ethyl acetate (200 mL). The organic layers were washed with water (150 mL) and the aqueous layer was separated and re-extracted with ethyl acetate (2×150 mL). The combined organic extracts were washed with brine (1×200 mL), dried over anhydrous sodium sulphate, filtered and evaporated under reduced pressure to afford 33B (brown oil, 15.2 g, 39.9 mmol, 93% yield). LC-MS Anal. Calc'd for $C_{17}H_{28}BNO_6Si$ 381.178. found [M−H] 312.2 for parent boronic acid, $T_r$=1.33 min (Method AY).

33C. ethyl 4-methoxy-3-(3-nitro-4-((2-(trimethylsilyl) ethoxy) methoxy) phenyl) butanoate (Absolute Stereochemistry not Determined)

To a stirred solution of 33B (7 g, 18.36 mmol) in Dioxane (120 mL) were added (E)-ethyl 4-methoxybut-2-enoate (3.44 g, 23.87 mmol), NaOH (16.52 mL, 16.52 mmol). Argon gas was bubbled through the mixture for 10 min. Then chloro(1,5-cyclooctadiene)rhodium(I) dimer (0.136 g, 0.275 mmol) was added at room temperature. Argon gas was bubbled through the mixture for another 5 min. Then the reaction tube was screw-capped and heated at 50° C. for 2 h. The reaction mixture was cooled to room temperature, quenched with AcOH (0.946 mL, 16.52 mmol), stirred for 5 minutes and diluted with water (50 mL). The aqueous layer was extracted with ethyl acetate (3×50 mL). The combined organic layer was washed with water (100 mL), brine (100 mL), dried over anhydrous sodium sulphate, filtered and concentrated under reduced pressure to afford a brown colored residue. The residue was purified via flash silica gel column chromatography to afford 33C (light yellow oil, 5.8 g, 14.03 mmol, 76%). LC-MS Anal. Calc'd for $C_{19}H_{31}NO_7Si$ 413.187. found [M+NH4] 431.2, $T_r$=3.518 min. (Method BB).

33D. ethyl 3-(3-amino-4-((2-(trimethylsilyl)ethoxy) methoxy)phenyl)-4-methoxybutanoate (Absolute Stereochemistry not Determined)

To a stirred solution of 33C (4.5 g, 10.88 mmol) in Ethyl acetate (50 mL) was added 10% w/w Palladium on carbon (1.158 g, 1.088 mmol) and the suspension was stirred, hydrogenated under pressure of 60 psi, at room temperature for 5 h. Then the suspension was filtered through a pad of celite and the filter cake was rinsed with ethyl acetate (200 mL). The combined filtrate was concentrated under reduced pressure to afford 33D as racemate (brown oil, 3.5 g, 9.13 mmol, 83%). LC-MS Anal. Calc'd for $C_{19}H_{33}NO_5Si$ 383.213. found [M+H] 384.5, $T_r$=1.59 min (Method AY).

Chiral SFC separation of 33D racemate gave 33D Enantiomer 1 $T_r$=8.37 min and 33D Enantiomer 2 $T_r$=9.11 min as single enantiomers (Method AS).

33D Enantiomer 1 (brown oil, 1.4 g, 3.65 mmol, 33.5% yield): LC-MS Anal. Calc'd for $C_{19}H_{33}NO_5Si$ 383.213. found [M+H] 384.9, $T_r$=3.051 min (Method CP).

33D Enantiomer 2 (brown oil, 1.4 g, 3.65 mmol, 33.5% yield): LC-MS Anal. Calc'd for $C_{19}H_{30}N_2O_4$ 383.213. found [M+H] 384.2, $T_r$=2.728 min (Method BB).

33E. ethyl 3-(3-((4-cyanophenyl)amino)-4-((2-(trimethylsilyl)ethoxy)methoxy) phenyl)-4-methoxybutanoate (Absolute Stereochemistry not Determined)

To a stirred solution 33D Enantiomer 1 (1.2 g, 3.13 mmol) in 1,4-Dioxane (15 mL) were added 4-bromobenzonitrile (0.683 g, 3.75 mmol)), Xantphos (0.217 g, 0.375 mmol), $Cs_2CO_3$ (3.06 g, 9.39 mmol). Then argon was purged for 10 min, followed by the addition of bis(dibenzylideneacetone) palladium (0.090 g, 0.156 mmol). Argon was again purged for another 5 min. The reaction mixture was heated at 110° C. for 6h. The reaction mixture was allowed to cool to room temperature and concentrated under reduced pressure to afford the crude residue, which was purified via flash chromatography to afford 33E (light yellow solid, 1.1 g, 2.270 mmol, 72.5% yield). LC-MS Anal. Calc'd for $C_{26}H_{36}N_2O_5Si$ 484.239. found [M−H] 483.2, $T_r$=3.815 min (Method BB).

33F. ethyl 3-(3-((4-cyanophenyl) amino)-4-hydroxyphenyl)-4-methoxybutanoate (Absolute Stereochemistry not Determined)

A mixture of 33E (1.1 g, 1.316 mmol) and TBAF in THF (3.95 mL, 3.95 mmol) in anhydrous THF (10 mL) was refluxed at 80° C. for 3 h. The reaction solvents were evaporated under reduced pressure to afford the residue. The residue was partitioned between ethyl acetate (20 mL) and saturated ammonium chloride solution (20 mL). The organic layer was separated and the aqueous layer was re-extracted with ethyl acetate (2×20 mL). The combined organic extracts were dried over sodium sulphate, filtered and evaporated under reduced pressure to afford the brown colored residue, which was purified via flash chromatography to afford 33F (Off white solid, 0.44 g, 1.242 mmol, 94% yield). LC-MS Anal. Calc'd for $C_{20}H_{22}N_2O_4$ 354.158. found [M+H] 355.0, $T_r$=1.16 min (Method AY).

33G. ethyl 3-(3-((4-cyanophenyl) amino)-4-(((trifluoromethyl) sulfonyl) oxy) phenyl)-4-methoxybutanoate (Absolute Stereochemistry not Determined)

To a stirred solution of 33F (0.75 g, 2.116 mmol), pyridine (0.856 mL, 10.58 mmol) in dry dichloromethane (10 mL) was purged with argon for 5 minutes. The solution was cooled to 0° C., added drop wise of trifluoromethanesulfonic anhydride (0.393 mL, 2.328 mmol). The reaction mixture was slowly warmed up to room temperature and stirred for 4 h at room temperature. Then the reaction solvents were evaporated under reduced pressure to afford brown colored residue, which was purified via flash chromatography to afford 33G (Colorless oil, 0.65 g, 1.336 mmol, 63.1% yield). LC-MS Anal. Calc'd for $C_{21}H_{21}F_3N_2O_6S$ 486.107. found [M–H]485.0, $T_r$=2.505 min (Method BB).

33H. ethyl 3-(3-((4-cyanophenyl) amino)-4-(1-methyl-1H-pyrazol-4-yl)phenyl)-4-methoxybutanoate (Absolute Stereochemistry not Determined)

To a stirred solution of 33G (100 mg, 0.206 mmol), in THF (3 mL) and water (0.5 mL) in a microwave vial added (1-methyl-1H-pyrazol-4-yl)boronic acid (78 mg, 0.617 mmol), potassium phosphate, tribasic (131 mg, 0.617 mmol), dicyclohexyl-(2',4',6'-triisopropyl-biphenyl-3-yl)-phosphane (19.60 mg, 0.041 mmol). Then the reaction mixture was purged with argon gas for 10 minutes. Chloro (2-dicyclohexylphosphino-2',4',6'-triisopropyl-1,1'-biphenyl)[2-(2'-amino-1,1'-biphenyl)]palladium(II) (16.17 mg, 0.021 mmol) was added to the reaction mixture and purged with argon gas for another 10 min. The reaction mixture was stirred and irradiated in microwave instrument at 80° C. for 1 h. Then the reaction mixture was allowed to cool to room temperature and filtered through pad of Celite. The celite pad was rinsed with excess of ethyl acetate and evaporated under reduced pressure to afford 33H (brown solid, 50 mg, 0.119 mmol, 58.1%). LC-MS Anal. Calc'd for $C_{24}H_{26}N_4O_3$ 418.200. found [M+H] 419.5, $T_r$=1.24 min (Method AY).

Example 33 Enantiomer 1. (S)-3-(3-((4-cyanophenyl) amino)-4-(1-methyl-1H-pyrazol-4-yl)phenyl)-4-methoxybutanoic Acid (Absolute Stereochemistry not Determined)

To a stirred solution of 33H (50 mg, 0.037 mmol) in MeOH (2 mL), water (2 mL) and THF (2 mL), was added LiOH (3.55 mg, 0.148 mmol) and stirred at room temperature for 4 h.

Then organic solvents were evaporated and the aqueous solution was acidified with saturated citric acid solution (pH~4), extracted with ethyl acetate (3×20 mL). The combined organic extracts were dried over sodium sulphate, filtered and concentrated to afford brown colored residue. The residue was purified by Preparative LCMS method to afford Example 33 Enantiomer 1 (Pale yellow solid, 6.0 mg, 0.015 mmol, 41.4% yield). LC-MS Anal. Calc'd for C $C_{22}H_{22}N_4O_3$ 390.169. found [M+H] 391.1, Tr=1.102 min (Method O). $^1$H NMR (400 MHz, $CD_3OD$) δ 7.74 (s, 1H), 7.64 (s, 1H), 7.49 (d, J=8.00 Hz, 1H), 7.40 (d, J=8.40 Hz, 2H), 7.22 (d, J=1.60 Hz, 1H), 7.17 (dd, J=1.60, 8.00 Hz, 1H), 6.74 (d, J=8.80 Hz, 2H), 3.84 (s, 3H), 3.51-3.58 (m, 2H), 3.30-3.39 (m, 4H), 2.78-2.83 (m, 1H), 2.55-2.61 (m, 1H).

Example 33 Enantiomer 2: (R)-3-(3-((4-cyanophenyl)amino)-4-(1-methyl-1H-pyrazol-4-yl)phenyl)-4-methoxybutanoic Acid (Absolute Stereochemistry not Determined)

Example 33 Enantiomer 2 was prepared from 33D Enantiomer 2 and (1-methyl-1H-pyrazol-4-yl) boronic acid, following the procedures described for the synthesis of Example 33 Enantiomer 1. LC-MS Anal. Calc'd for $C_{22}H_{22}N_4O_3$ 390.169. found [M+H] 391.1, Tr=1.076 min (Method O). $^1$H NMR (400 MHz, CD3OD): δ 7.76 (s, 1H), 7.66 (s, 1H), 7.51 (d, J=8.00 Hz, 1H), 7.41-7.43 (m, 2H), 7.18-7.23 (m, 2H), 6.75-6.77 (m, 2H), 3.86 (s, 3H), 3.54-3.59 (m, 2H), 3.33-3.38 (m, 4H), 2.79-2.83 (m, 1H), 2.57-2.61 (m, 1H).

Example 34-37

Absolute Stereochemistry not Determined

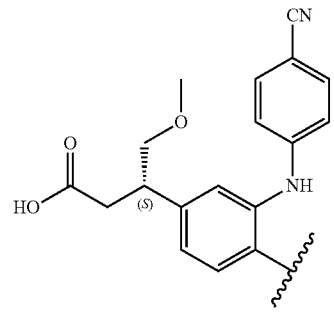

Example 34-37 Enantiomer 1 were prepared from 33D Enantiomer 1 and corresponding aryl boronates following the procedure described for the synthesis of Example 33 Enantiomer 1.

| Ex. No. | Name | R | $T_R$ (min) | $[M + H]^+$ |
|---|---|---|---|---|
| 34 | (S)-3-(4-(benzo[d][1,3]dioxol-5-yl)-3-((4-cyanophenyl)amino)phenyl)-4-methoxybutanoic acid (absolute stereochemistry not determined) | | 1.275 Method O | 431.2 |

| Ex. No. | Name | R | $T_R$ (min) | $[M + H]^+$ |
|---|---|---|---|---|
| 35 | (S)-3-(3-((4-cyanophenyl)amino)-4-(furan-3-yl)phenyl)-4-methoxybutanoic acid (absolute stereochemistry not determined) | furan-3-yl | 1.199 Method O | 377.2 |
| 36 | (S)-3-(3-((4-cyanophenyl)amino)-4-(1-(4-methoxybenzyl)-1H-pyrazol-4-yl)phenyl)-4-methoxybutanoic acid (absolute stereochemistry not determined) | 1-(4-methoxybenzyl)-1H-pyrazol-4-yl | 1.226 Method O | 497.3 |
| 37 | (S)-3-(2-((4-cyanophenyl)amino)- -methyl-[1,1'-biphenyl]-4-yl)-4-methoxybutanoic acid (absolute stereochemistry not determined) | 3-methylphenyl | 1.925 Method R | 401.2 |

Example 38-45

Absolute Stereochemistry not Determined

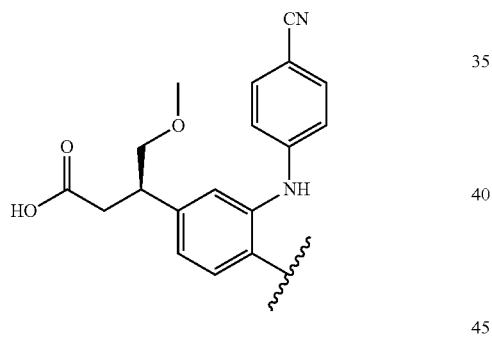

Example 38-45 Enantiomer 2 were prepared from 33D Enantiomer 2 and corresponding aryl boronates following the procedure described for the synthesis of Example 33 Enantiomer 2.

| Ex. No. | Name | R | $T_R$ (min) | $[M + H]^+$ |
|---|---|---|---|---|
| 38 | (R)-3-(4-(benzo[d][1,3]dioxol-5-yl)-3-((4-cyanophenyl)amino)phenyl)-4-methoxybutanoic acid (absolute stereochemistry not determined) | benzo[d][1,3]dioxol-5-yl | 1.729 Method O. | 431.2 |
| 39 | (R)-3-(3-((4-cyanophenyl)amino)-4-(furan-3-yl)phenyl)-4-methoxybutanoic acid (absolute stereochemistry not determined) | furan-3-yl | 1.203 Method O | 377.2 |

-continued

| Ex. No. | Name | R | $T_R$ (min) | [M + H]$^+$ |
|---|---|---|---|---|
| 40 | (R)-3-(3-((4-cyanophenyl)amino)-4-(2,3-dihydrobenzofuran-5-yl)phenyl)-4-methoxybutanoic acid (absolute stereochemistry not determined) | 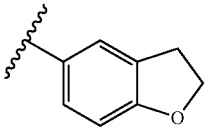 [SMILES: *c1ccc2c(c1)CCO2] | 1.312 Method O | 429.2 |
| 41 | (R)-3-(4-(benzofuran-2-yl)-3-((4-cyanophenyl)amino)phenyl)-4-methoxybutanoic acid (absolute stereochemistry not determined) | 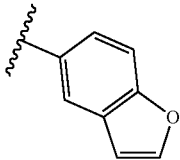 [SMILES: *c1ccc2occc2c1] | 1.489 Method O | 427.2 |
| 42 | (R)-3-(4-(benzo[b]thiophen-2-yl)-3-((4-cyanophenyl)amino)phenyl)-4-methoxybutanoic acid (absolute stereochemistry not determined) | 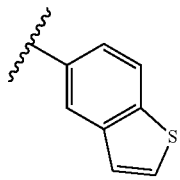 [SMILES: *c1ccc2sccc2c1] | 1.567 Method O | 443.2 |
| 43 | (R)-3-(3-((4-cyanophenyl)amino)-4-(pyrimidin-5-yl)phenyl)-4-methoxybutanoic acid | 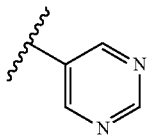 | 0.827 Method O | 389.2 |
| 44 | (R)-3-(4-(1-benzyl-1H-pyrazol-4-yl)-3-((4-cyanophenyl)amino)phenyl)-4-methoxybutanoic acid (absolute stereochemistry not determined) | 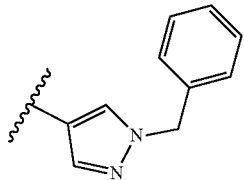 [SMILES: *c1cnn(Cc2ccccc2)c1] | 1.235 Method O | 467.2 |
| 45 | (R)-3-(3-((4-cyanophenyl)amino)-4-(1-(4-methoxybenzyl)-1H-pyrazol-4-yl)phenyl)-4-methoxybutanoic acid (absolute stereochemistry not determined) | 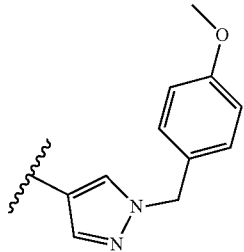 [SMILES: *c1cnn(Cc2ccc(OC)cc2)c1] | 1.233 Method O. | 497.3 |

Example 46

(R)-3-(3-((2-ethoxypyrimidin-5-yl)amino)-4-(furan-3-yl)phenyl)pentanoic Acid (Absolute Stereochemistry not Determined)

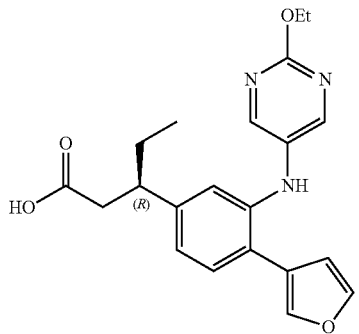

46A. methyl 3-(3-amino-4-bromophenyl)pentanoate (Absolute Stereochemistry not Determined)

To a stirred solution of 2B (3.5 g, 11.07 mmol) in MeOH (30 mL), iron (4.95 g, 89 mmol), ammonium chloride (4.74 g, 89 mmol) in water (10 mL) was added. The reaction suspension was heated at 70° C. for 5 h. The reaction mixture was allowed to cool to room temperature and filtered through a pad of celite. The celite pad was washed with excess of methanol and evaporated under reduced pressure to afford brown colored oil. The oily compound was reconstituted in ethyl acetate (200 mL) and washed with water, brine, dried over sodium sulphate, filtered and evaporated under reduced pressure to afford the 46A (brown oil, 1.4 g, 4.50 mmol, 40.7%). LC-MS Anal. Calc'd for $C_{12}H_{16}BrNO_2$ 285.036. found [M+3] 288.0, $T_r$=1.823 min (Method BB)

Chiral separation of 46A shown enantiomeric excess of 87%, resolved to provide 46A Enantiomer 1 ($T_r$=7.06 min) and 46A Enantiomer 2 ($T_r$=8.52 min) as single enantiomers (Method BS).

46A Enantiomer 1 (550 mg, 1.768 mmol, 15.97% yield), $T_r$=7.06 min (Method BS). LC-MS Anal. Calc'd for $C_{12}H_{16}BrNO_2$ 285.036. found [M+3] 288.0, $T_r$=2.111 min (Method BB).

46A Enantiomer 2, $T_r$=8.52 min (Method BS). LC-MS Anal. Calc'd for $C_{12}H_{16}BrNO_2$ 285.036. found [M+3] 288.0, $T_r$=2.111 min (Method BB).

46B. methyl 3-(4-bromo-3-((2-ethoxypyrimidin-5-yl) amino) phenyl) pentanoate (Absolute Stereochemistry not Determined)

To a stirred solution of 46A Enantiomer 1 (2 g, 6.98 mmol), 5-bromo-2-ethoxypyrimidine (1.844 g, 9.08 mmol), Xantphos (0.606 mg, 1.048 mmol) and $Cs_2CO_3$ (6.84 g, 20.96 mmol) in 1,4-Dioxane (30 mL), argon gas was bubbled for 5 min. Then Bis(dibenzylideneacetone)palladium (0.200 g, 0.35 mmol) was added and argon gas was bubbled for another 5 min. The reaction mixture was heated at 110° C. for 16 h in a sealed tube. Then the reaction mixture was cooled to room temperature and evaporated under reduced pressure to afford a residue. The residue was reconstituted in a mixture of ethyl acetate (100 mL) and water (50 mL). The organic layer was separated and aqueous layer was extracted with ethyl acetate (2×100 mL). The combined organic layer was washed with water (50 mL), brine (50 mL), dried over anhydrous sodium sulfate, filtered and evaporated under reduced pressure to give the crude material, which was purified via flash silica gel column chromatography to afford 46B (yellow oil, 2 g, 4.60 mmol, 65.9% yield). LC-MS Anal. Calc'd for $C_{18}H_{22}BrN_3O_3$, 407.084. found [M+3]410.2, $T_r$=2.240 min (Method BB).

46C. 1.methyl3-(3-((2-ethoxypyrimidin-5-yl) amino)-4-(furan-3-yl)phenyl)pentanoate (Absolute Stereochemistry not Determined)

To a stirred solution of 46B (40 mg, 0.098 mmol) in dry Tetrahydrofuran (1.5 mL), furan-3-boronic acid (21.92 mg, 0.196 mmol), potassium phosphate tribasic (62.4 mg, 0.294 mmol) in Water (0.5 mL) were added at room temperature and argon was purged for 10 minutes. Then Dicyclohexyl-(2',4',6'-triisopropyl-biphenyl-3-yl)-phosphane (9.34 mg, 0.020 mmol) and chloro(2-dicyclohexylphosphino-2',4',6'-triisopropyl-1,1'-biphenyl)[2-(2'-amino-1,1'-biphenyl)]palladium(ii) (11.56 mg, 0.015 mmol) were added and argon gas was purged for 5 minutes. The reaction mixture was heated at 80° C. and stirred for 12 h in a sealed tube. To the reaction mixture water (10 mL) was added and it was extracted with ethyl acetate (3×15 mL). The combined organic extracts were dried over sodium sulphate, filtered and evaporated under reduced pressure to give the crude material, which was purified via flash silica gel column chromatography to afford 46C (brown mass, 35 mg, 0.089 mmol, 90% yield). LC-MS Anal. Calc'd for $C_{22}H_{25}N_3O_4$, 395.185. found [M+H] 396.2, $T_r$=3.191 min (Method U).

Example 46. (R)-3-(3-((2-ethoxypyrimidin-5-yl) amino)-4-(furan-3-yl)phenyl)pentanoic Acid (Absolute Stereochemistry not Determined)

To a stirred solution of 46C (40 mg, 0.101 mmol) in mixture of THF (0.5 mL), Methanol (1 mL) and Water (0.25 mL) was added $LiOH.H_2O$ (13.89 mg, 0.580 mmol) and stirred at room temperature for 3 h. The organic solvents were evaporated under reduced pressure; aqueous solution was acidified to pH~3-4 with saturated citric acid solution, and extracted with ethyl acetate (2×10 mL). The combined organic layer was washed with water (10 mL), brine (10 mL), dried over anhydrous sodium sulfate, filtered and evaporated under reduced pressure to afford the crude material, which was purified via preparative LCMS to afford Example 46 (pale yellow solid, 0.6 mg, 1.463 µmol, 93% yield). LC-MS Anal. Calc'd for $C_{21}H_{23}N_3O_4$, 381.169. found [M+H] 382.1, $T_r$=1.504 min (Method O). $^1$HNMR (400 MHz, CD3OD) δ 8.13 (s, 2H), 7.76 (s, 1H), 7.52 (t, J=3.60 Hz, 1H), 7.37-7.39 (m, 1H), 6.97-6.99 (m, 2H), 6.69-6.69 (m, 1H), 4.35 (q, J=6.80 Hz, 2H), 2.89-3.01 (m, 1H), 2.65-2.63 (m, 1H), 2.55-2.57 (m, 1H), 1.58-1.80 (m, 2H), 1.40 (t, J=7.20 Hz, 3H), 0.84 (t, J=7.60 Hz, 3H).

Example 47-56

Homochiral

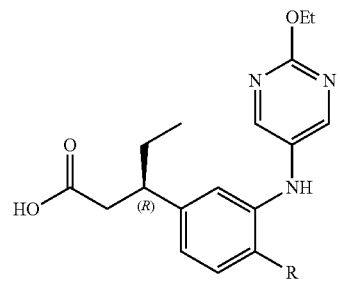

Examples 47-56 were prepared using the 46A Enantiomer 1 and corresponding aryl/heteroaryl boronates following the procedure described for the synthesis of Example 46.

| Ex. No. | Name | R | $T_R$ (min) | $[M + H]^+$ |
| --- | --- | --- | --- | --- |
| 47 | (R)-3-(3-((2-ethoxypyrimidin-5-yl)amino)-4-(1-(4-methoxybenzyl)-1H-pyrazol-4-yl)phenyl)pentanoic acid (absolute stereochemistry not determined) | ![pyrazole-CH2-C6H4-OMe] | 1.580 (Method O) | 502.3 |

-continued

| Ex. No. | Name | R | T$_R$ (min) | [M + H]$^+$ |
|---|---|---|---|---|
| 48 | (R)-3-(3-((2-ethoxypyrimidin-5-yl)amino)-4-(1-(4-fluorophenyl)-1H-pyrazol-4-yl)phenyl)pentanoic acid (absolute stereochemistry not determined) | | 1.984 (Method R) | 476.2 |
| 49 | (R)-3-(2-((2-ethoxypyrimidin-5-yl)amino)-3'-fluoro-4'-methoxy-[1,1'-biphenyl]1-4-yl)pentanoic acid (absolute stereochemistry not determined) | | 1.930 (Method R) | 440.2 |
| 50 | (R)-3-(3-((2-ethoxypyrimidin-5-yl)amino)-4-(1H-indazol-4-yl)phenyl)pentanoic acid (absolute stereochemistry not determined) | | 1.578 (Method R) | 432.2 |
| 51 | (R)-3-(3-((2-ethoxypyrimidin-5-yl)amino)-4-(1-methyl-1H-indazol-5-yl)phenyl)pentanoic acid (absolute stereochemistry not determined) | | 1.736 (Method R) | 446.3 |
| 52 | (R)-3-(3-((2-ethoxypyrimidin-5-yl)amino)-4-(3-fluoropyridin-4-yl)phenyl)pentanoic acid (absolute stereochemistry not determined) | | 1.382 (Method R) | 411.2 |
| 53 | (R)-3-(2-((2-ethoxypyrimidin-5-yl)amino)-2'-fluoro-4'-methoxy-[1,1'-biphenyl]-4-yl)pentanoic acid (absolute stereochemistry not determined) | | 1.932 (Method R) | 440.2 |
| 54 | (R)-3-(4-(3,5-dimethylisoxazol-4-yl)-3-((2-ethoxypyrimidin-5-yl)amino)phenyl)pentanoic acid (absolute stereochemistry not determined) | | 1.660 (Method R) | 411.2 |
| 55 | (R)-3-(3-((2-ethoxypyrimidin-5-yl)amino)-4-(1-(2-morpholinoethyl)-1H-pyrazol-4-yl)phenyl)pentanoic acid (absolute stereochemistry not determined) | | 1.120 (Method R) | 495.3 |
| 56 | (R)-3-(4-(8-(tert-butoxycarbonyl)-8-azabicyclo[3.2.1]oct-2-en-3-yl)-3-((2-ethoxypyrimidin-5-yl)amino)phenyl)pentanoic acid (absolute stereochemistry not determined) | | 2.123 (Method R) | 523.3 |

Example 57 and Example 58

(R)-3-(4-(2,4-dimethylthiazol-5-yl)-3-((2-ethylpyrimidin-5-yl)amino)phenyl) pentanoic Acid (Absolute Stereochemistry not Determined)

(S)-3-(4-(2,4-dimethylthiazol-5-yl)-3-((2-ethylpyrimidin-5-yl)amino)phenyl) pentanoic Acid (Absolute Stereochemistry not Determined)

(En-1)

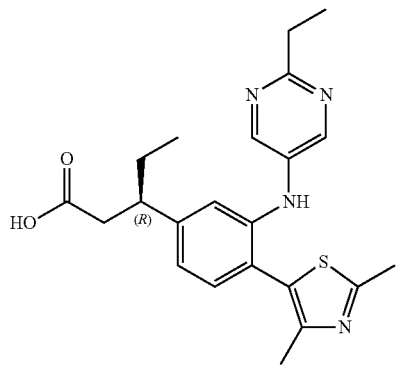

(En-2)

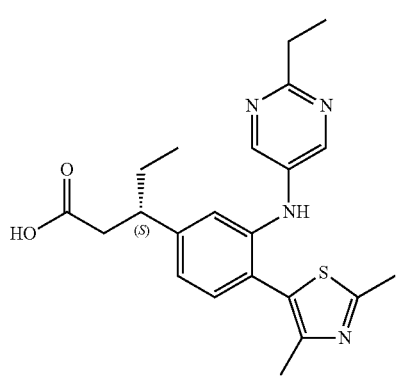

57A. methyl 3-(4-bromo-3-((2-ethylpyrimidin-5-yl)amino) phenyl) pentanoate (Absolute Stereochemistry not Determined)

To a stirred solution of 46A Enantiomer 1 (550 mg, 1.826 mmol), 5-bromo-2-ethylpyrimidine (410 mg, 2.191 mmol), Xantphos (106 mg, 0.183 mmol), $Cs_2CO_3$ (1785 mg, 5.48 mmol) in Dioxane (8 mL), argon gas was bubbled for 5 min. Then added Bis(dibenzylideneacetone)palladium (52.5 mg, 0.091 mmol) and argon gas was bubbled for 5 min. The reaction mixture was heated at 110° C. for 6 h in a pressure tube. The reaction mixture was cooled to room temperature and evaporated under reduced pressure to afford a residue. The residue was reconstituted in a mixture of ethyl acetate (20 mL) and water (20 mL). The organic layer was separated and aqueous layer was extracted with ethyl acetate (2×20 mL). The combined organic layer was washed with water (25 mL), brine (25 mL), dried over anhydrous sodium sulphate, filtered and evaporated under reduced pressure to give the crude material, which was purified via flash silica gel column chromatography to afford 57A (brown oil, 600 mg, 1.529 mmol, 84% yield). LC-MS Anal. Calc'd for $C_{18}H_{22}BrN_3O_2$ 391.090. found [M+3]394.1, $T_r$=2.995 min (Method BB).

57B. methyl 3-(4-(5,5-dimethyl-1,3,2-dioxaborinan-2-yl)-3-((2-ethylpyrimidin-5-yl) amino)phenyl)pentanoate (Absolute Stereochemistry not Determined)

57B was prepared using the 57A following the procedure described for the synthesis of 19A. LC-MS Anal. Calc'd for $C_{23}H_{32}BN_3O_4$ 425.249. found MS (ES): m/z=358.1 [M−H] for parent boronic acid. $T_r$=1.097 min (Method BB).

57C. methyl 3-(4-(2,4-dimethylthiazol-5-yl)-3-((2-ethylpyrimidin-5-yl)amino)phenyl)pentanoate (Absolute Stereochemistry not Determined)

57C were prepared using the 57B and 5-bromo-2,4-dimethylthiazole following the procedure described for the synthesis 19B. LC-MS Anal. Calc'd for $C_{23}H_{28}N_4O_2S$ 424.193. found [M+H] 425.4, $T_r$=1.29 min (Method AY).

Example 57 Enantiomer 1. (R)-3-(4-(2,4-dimethylthiazol-5-yl)-3-((2-ethylpyrimidin-5-yl)amino)phenyl)pentanoic Acid (Absolute Stereochemistry not Determined)

Example 57 Enantiomer 1 were prepared using the 57C following the hydrolysis procedure described for the synthesis of Example 19. LC-MS Anal. Calc'd for $C_{22}H_{26}N_4O_2S$ 410.178. found [M+H] 411.1, $T_r$=1.252 min (Method O). 1H NMR (400 MHz, $CD_3OD$) δ 8.28 (s, 2H), 7.35 (d, J=8.00 Hz, 1H), 7.23 (d, J=1.60 Hz, 1H), 7.13 (dd, J=1.60, 8.00 Hz, 1H), 3.00-3.04 (m, 1H), 2.82-2.88 (m, 2H), 2.67-2.74 (m, 4H), 2.56-2.62 (m, 1H), 2.29 (s, 3H), 1.75-1.80 (m, 1H), 1.66-1.71 (m, 1H), 1.31 (t, J=7.60 Hz, 3H), 0.88 (t, J=7.20 Hz, 3H).

Example 58

Homochiral (S)-3-(4-(2,4-dimethylthiazol-5-yl)-3-((2-ethylpyrimidin-5-yl)amino)phenyl)pentanoic Acid (Absolute Stereochemistry not Determined)

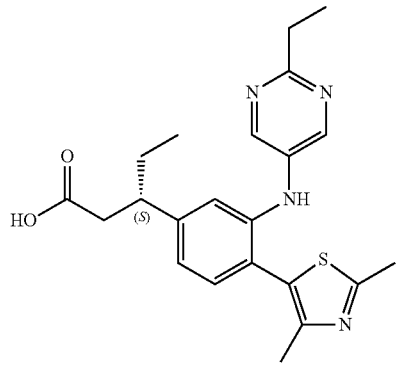

58A. methyl 3-(4-bromophenyl) pentanoate (Absolute Stereochemistry not Determined)

To a stirred solution of 2-(4-bromophenyl)-4,4,5,5-tetramethyl-1,3,2-dioxaborolane (6 g, 21.20 mmol) in 1,4-Dioxane (60 ml) were added sodium hydroxide (19.08 mL, 19.08 mmol), argon gas was purged for 15 mins. Then added (E)-methyl pent-2-enoate (2.420 g, 21.20 mmol), chlorobis(ethylene)rhodium(I) dimer (0.124 g, 0.318 mmol) and (R)-(+)-2,2'-bis(diphenyl phosphino)-1,1'-binaphthyl (0.290 g, 0.466 mmol) at room temperature. Argon gas was purged for 5 min. The reaction tube was screw-capped and stirred at room temperature for 12 h. The reaction mixture was quenched with acetic acid (1.214 mL, 21.20 mmol), stirred for 5 mins and diluted with water (100 mL). The aqueous layer was extracted with ethyl acetate (3×100 mL). The combined organic layer was washed with water (50 mL), brine (50 mL), dried over anhydrous sodium sulphate, filtered and evaporated under reduced pressure to afford the crude material, which was purified by flash silica gel column chromatography to afford 58A (brown oil, 4.5 g, 16.6 mmol, 48.6%). LC-MS Anal. Calc'd for $C_{12}H_{16}BrNO_2$ 270.0. found [M+3] 273.0, $T_r$=2.170 min (Method BB).

58B. methyl 3-(4-bromo-3-nitrophenyl)pentanoate (Absolute Stereochemistry not Determined)

To a stirred solution of 58A (4 g, 14.75 mmol) in $H_2SO_4$ (40 mL, 750 mmol) at 0° C., potassium nitrate (1.491 g, 14.75 mmol) was added portion wise and stirred at 0° C. for 30 mins. The reaction mixture was added to cold water (200 mL) and extracted with ethyl acetate (2×200 mL). The combined organic layers were washed with saturated aqueous $NaHCO_3$ solution (100 mL), brine (100 mL), dried over anhydrous sodium sulphate, filtered and evaporated under reduced pressure to afford 58B (4 g, 12.65 mmol, 86% yield). $^1H$ NMR (400 MHz, $CD_3OD$) δ 7.74-7.77 (m, 2H), 7.44-7.42 (m, 1H), 3.58 (s, 3H), 3.00-3.12 (m, 1H), 2.62-2.80 (m, 2H), 1.64-1.80 (m, 2H), 0.80 (t, J=7.20 Hz, 3H).

58C. methyl 3-(3-amino-4-bromophenyl)pentanoate (Absolute Stereochemistry not Determined)

To a stirred solution of 58B (3.5 g, 11.07 mmol) in MeOH (30 mL), was added iron (4.95 g, 89 mmol), and ammonium chloride (4.74 g, 89 mmol) in Water (10 mL). The reaction suspension was heated and stirred at 70° C. for 5 h. The reaction mixture was allowed to cool to room temperature and filtered through a pad of celite. The celite pad was washed with excess of methanol and concentrated under reduced pressure to afford brown colored oil. The oily compound was reconstituted in ethyl acetate (200 mL) and aqueous saturated sodium bicarbonate solution (200 mL). The organic layer was separated and the aqueous layer was re-extracted with ethyl acetate (2×200 mL). The combined organic extracts was washed with water (50 mL), brine (50 mL), dried over sodium sulphate, filtered and evaporated under reduced pressure to afford the 58C (brown oil, 2 g, 6.92 mmol, 48.6%). LC-MS Anal. Calc'd for $C_{12}H_{16}BrNO_2$ 285.036. found [M+3] 288.0, $T_r$=1.826 min (Method BB)

Chiral separation of 58C shown enantiomeric excess of 87%, resolved to gave 58C Enantiomer 1 ($T_r$=7.16 min) and 58C Enantiomer 2 ($T_r$=8.28 min) as single enantiomers (Method BS).

58C Enantiomer 2 (1.2 g, 4.15 mmol, 29.2% yield), $T_r$=7.16 min (Method BS). LC-MS Anal. Calc'd for $C_{12}H_{16}BrNO_2$ 285.036. found [M+3] 288.0, $T_r$=1.876 min (Method BB).

58D. methyl 3-(4-bromo-3-((2-ethylpyrimidin-5-yl)amino)phenyl)pentanoate (Absolute Stereochemistry not Determined)

58D was prepared using 58C Enantiomer 2 and 5-bromo-2-ethylpyrimidine following the procedure described for the synthesis of 57A (brown oil, 325 mg, 0.828 mmol, 71.3% yield). LC-MS Anal. Calc'd for $C_{18}H_{22}BrN_3O_2$ 391.090. found [M+3] 394.0, $T_r$=2.908 min (Method N).

58E. 5-(5,5-dimethyl-1,3,2-dioxaborinan-2-yl)-2,4-dimethylthiazole (Absolute Stereochemistry not Determined)

58E was prepared using the 5-bromo-2,4-dimethylthiazole following the procedure described for the synthesis of 2D. LC-MS Anal. Calc'd for $C_{10}H_{16}BNO_2S$ 225.099. found MS (ES): m/z=158.0 [M+H] for parent boronic acid. $T_r$=0.43 min (Method AA).

58F. methyl 3-(4-(2,4-dimethylthiazol-5-yl)-3-((2-ethylpyrimidin-5-yl)amino)phenyl)pentanoate (Absolute Stereochemistry not Determined)

58F were prepared using the 58D and 58E following the procedure described for the synthesis of Example 2. LC-MS Anal. Calc'd for $C_{23}H_{28}N_4O_2S$ 424.193. found [M+H] 425.0, $T_r$=1.29 min (Method AY).

Example 58. (S)-3-(4-(2,4-dimethylthiazol-5-yl)-3-((2-ethylpyrimidin-5-yl)amino)phenyl)pentanoic Acid (Absolute Stereochemistry not Determined)

Example 58 Enantiomer 2 were prepared using the 58F and following the hydrolysis procedure described for the synthesis of Example 46. LC-MS Anal. Calc'd for $C_{22}H_{26}N_4O_2S$ 410.178. found [M+H] 411.1, $T_r$=1.249 min (Method O). $^1H$ NMR (400 MHz, $CD_3OD$) δ 8.28 (s, 2H), 7.35 (d, J=7.60 Hz, 1H), 7.23 (d, J=2.40 Hz, 1H), 7.12 (dd, J=1.60, 8.00 Hz, 1H), 2.99-3.05 (m, 1H), 2.82-2.88 (m, 2H), 2.67-2.74 (m, 4H), 2.56-2.62 (m, 1H), 2.29 (s, 3H), 1.75-1.80 (m, 1H), 1.66-1.71 (m, 1H), 1.31 (t, J=7.60 Hz, 3H), 0.88 (t, J=7.20 Hz, 3H).

Example 59

(S)-3-(4-(2,4-dimethylthiazol-5-yl)-3-((2-ethylpyrimidin-5-yl)amino)phenyl)pentanoic Acid (Absolute Stereochemistry not Determined)

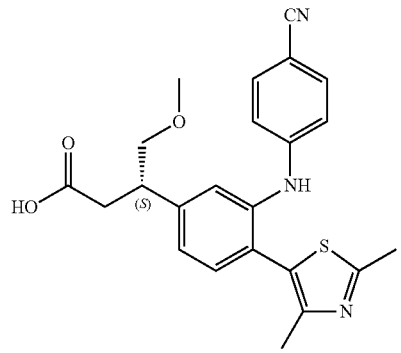

59A Enantiomer 2. methyl 3-(4-bromophenyl)-4-methoxybutanoate (Absolute Stereochemistry not Determined)

To a stirred solution of 2-(4-bromophenyl)-4,4,5,5-tetramethyl-1,3,2-dioxaborolane (5 g, 17.67 mmol) in 1,4-

Dioxane (60 mL) were added sodium hydroxide (15.90 mL, 15.90 mmol). Argon gas was passed through the mixture for 15 mins. Then added (E)-methyl 4-methoxybut-2-enoate (4.60 g, 35.3 mmol), chlorobis(ethylene)rhodium(I) dimer (0.103 g, 0.265 mmol) and (R)-(+)-2,2'-bis(diphenylphosphino)-1,1'-binaphthyl (0.242 g, 0.389 mmol) at room temperature. Argon gas was passed through it for another 5 mins. The reaction mixture was screw-capped and stirred at room temperature for 12 h. The reaction suspension was quenched with acetic acid (1.012 mL, 17.67 mmol), stirred for 5 min and diluted with water (100 mL). The aqueous layer was extracted with ethyl acetate (3×100 mL). The combined organic layer was washed with water (50 mL), brine (50 mL), dried over anhydrous sodium sulphate, filtered and concentrated under reduced pressure to afford the crude material, which was purified by flash silica gel column chromatography to afford 59A (yellow oil, 3.6 g, 10.03 mmol, 80% yield). $^1$H NMR (400 MHz, CD3OD) δ 7.42-7.46 (m, 2H), 7.18-7.21 (m, 2H), 3.75 (s, 3H), 3.48-3.53 (m, 3H), 3.34 (s, 3H), 2.79-2.87 (m, 1H), 2.57-2.65 (m, 1H).

59B: methyl 3-(4-bromo-3-nitrophenyl)pentanoate (Absolute Stereochemistry not Determined)

To a stirred solution of 59A (3.6 g, 10.03 mmol) in $H_2SO_4$ (40 mL, 750 mmol) potassium nitrate (1.014 g, 10.03 mmol) was added portion wise at 0° C. and stirred for 30 min. The reaction mixture was added to cold water (200 mL) and extracted with ethyl acetate (2×200 mL). The organic layers were washed with saturated aqueous $NaHCO_3$ solution (100 mL), brine (100 mL), dried over sodium sulphate, filtered and evaporated under reduced pressure to afford 59B (3 g, 9.03 mmol, 90% yield). $^1$H NMR (400 MHz, DMSO-d6) δ 7.71-7.72 (m, 1H), 7.63-7.66 (m, 1H), 7.35-7.39 (m, 1H), 3.75 (s, 3H), 3.48-3.53 (m, 3H), 3.34 (s, 3H), 2.79-2.87 (m, 1H), 2.57-2.65 (m, 1H).

59C. methyl 3-(3-amino-4-bromophenyl)-4-methoxybutanoate (Absolute Stereochemistry not Determined)

To a stirred solution of 59B (2 g, 6.02 mmol) in MeOH (15 mL), iron (5.38 g, 96 mmol), ammonium chloride 5.15 g, 96 mmol) in Water (10 mL) was added. The reaction suspension was heated at 70° C. for 5 h. The reaction mixture was allowed to cool to room temperature and filtered through a pad of celite. The celite pad was washed with excess of methanol and concentrated under reduced pressure to afford brown colored oil. The oily compound was reconstituted in ethyl acetate (200 mL) and aqueous saturated sodium bicarbonate solution (200 mL). The organic layer was separated and the aqueous layer was re-extracted with ethyl acetate (2×200 mL). The combined organic extracts were washed with water (50 mL), brine (50 mL), dried over sodium sulphate, filtered and evaporated under reduced pressure to afford the 59C (brown oil, 1.8 g, 5.18 mmol, 86%). LC-MS Anal. Calc'd for $C_{12}H_{16}BrNO_3$ 301.031. found [M+2] 303.0, $T_r$=2.164 min (Method BB).

Chiral separation of 59C shown enantiomeric excess of 86.2%, resolved to gave 59C Enantiomer 1, $T_r$=6.35 min and 59C Enantiomer 2, $T_r$=7.34 min (Method BS).

59C Enantiomer 2 (1.5 g, 4.32 mmol, 71.7% yield), $T_r$=7.27 min (Method BS). LC-MS Anal. Calc'd for $C_{12}H_{16}BrNO_3$ 301.031. found [M+3] 304.0, $T_r$=1.673 min (Method BB).

59D. methyl 3-(4-bromo-3-((4-cyanophenyl)amino) phenyl)-4-methoxybutanoate (Absolute Stereochemistry not Determined)

59D was prepared using the 59C Enantiomer 2 and 4-bromo benzonitrile following the procedure described for the synthesis of 46B. LC-MS Anal. Calc'd for $C_{19}H_{19}BrN_2O_3$ 402.058. found [M+2] 404.3, $T_r$=3.069 min (Method BB).

59E. methyl 3-(3-((4-cyanophenyl)amino)-4-(5,5-dimethyl-1,3,2-dioxaborinan-2-yl)phenyl)-4-methoxybutanoate (Absolute Stereochemistry not Determined)

59E was prepared using the 59D following the procedure described for the synthesis of 19A. LC-MS Anal. Calc'd for $C_{24}H_{29}BN_2O_5$ 436.217. found MS (ES): m/z=369.2 [M+H] for parent boronic acid. $T_r$=1.212 min (Method BB).

59F. methyl 3-(3-((4-cyanophenyl)amino)-4-(2,4-dimethylthiazol-5-yl)phenyl)-4-methoxybutanoate (Absolute Stereochemistry not Determined)

59F were prepared using the 59E and 5-bromo-2, 4-dimethylthiazole following the procedure described for the synthesis of 19B. LC-MS Anal. Calc'd for $C_{24}H_{25}N_3O_3S$ 435.162. found [M+H] 436.2, $T_r$=1.05 min (Method AA).

Example 59. (S)-3-(3-((4-cyanophenyl)amino)-4-(2, 4-dimethylthiazol-5-yl)phenyl)-4-methoxybutanoic Acid (Absolute Stereochemistry not Determined)

Example 59 Enantiomer 2 was prepared using the 59F following the hydrolysis procedure described for the synthesis of Example 46. LC-MS Anal. Calc'd for $C_{23}H_{23}N_3O_3S$ 421.146. found [M+H] 422.1, $T_r$=1.238 min (Method O). $^1$H NMR (400 MHz, $CD_3OD$) δ 7.32-7.34 (m, 2H), 7.23-7.27 (m, 2H), 7.08-7.11 (m, 1H), 6.72-6.74 (m, 2H), 3.46-3.51 (m, 2H), 3.20-3.25 (m, 4H), 2.69-2.75 (m, 1H), 2.56 (s, 3H), 2.49-2.55 (m, 1H), 2.15 (s, 3H).

Example 60

(R)-3-(4-(2,4-dimethylthiazol-5-yl)-3-((2-ethylpyrimidin-5-yl) amino)phenyl)pentanoic Acid (Absolute Stereochemistry not Determined)

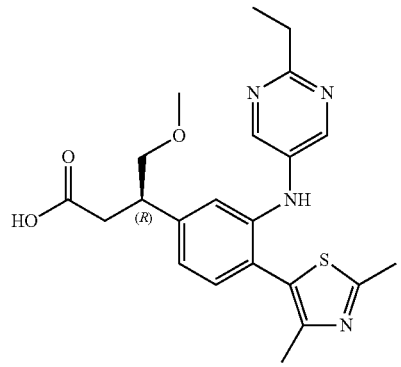

60A Enantiomer 1: methyl 3-(4-bromophenyl)-4-methoxybutanoate (Absolute Stereochemistry not Determined)

To a stirred solution of 2-(4-bromophenyl)-4,4,5,5-tetramethyl-1,3,2-dioxaborolane (5 g, 17.67 mmol) in 1,4-Dioxane (60 ml) were added sodium hydroxide (15.90 mL, 15.90 mmol). Argon gas was passed through the mixture for 15 min. Then added (E)-methyl 4-methoxybut-2-enoate (4.60 g, 35.3 mmol), chlorobis(ethylene)rhodium(I) dimer (0.103 g, 0.265 mmol) and (S)-(−)-2,2'-bis(diphenylphosphino)-1,1'-binaphthyl (0.242 g, 0.265 mmol) at room temperature. Argon gas was passed through the mixture for another 5 min. The reaction mixture was screw-capped and stirred at room temperature for 12 h. The reaction mixture was quenched with acetic acid (1.012 mL, 17.67 mmol), stirred for 5 min and diluted with water (100 mL). The aqueous layer was extracted with ethyl acetate (3×100 mL). The combined organic layers were washed with water (50 mL), brine (50 mL), dried over anhydrous sodium sulphate, filtered and evaporated under reduced pressure to afford the crude material, which was purified by flash silica gel column chromatography to afford 60A (yellow oil, 4.5 g, 15.67 mmol, 89% yield). $^1$H NMR (400 MHz, CD3OD) δ 7.21-7.46 (m, 2H), 7.18-7.20 (m, 2H), 3.75 (s, 3H), 3.48-3.53 (m, 3H), 3.34 (s, 3H), 2.80-2.86 (m, 1H), 2.58-2.64 (m, 1H).

60B: methyl 3-(4-bromo-3-nitrophenyl) pentanoate (Absolute Stereochemistry not Determined)

To a stirred solution of 60A (4.5 g, 12.54 mmol) in $H_2SO_4$ (40 mL, 750 mmol) potassium nitrate (1.268 g, 12.54 mmol) was added portion wise at 0° C., and stirred for 30 min. The reaction mixture was added to cold water (200 mL), and extracted with ethyl acetate (2×200 mL). The organic layers were washed with saturated aqueous $NaHCO_3$ solution (100 mL), brine (100 mL), dried over sodium sulphate, filtered and evaporated under reduced pressure to afford 60B (3.6 g, 11.39 mmol, 86% yield). $^1$H (NMR, 400 MHz, $CD_3OD$) δ 7.82 (s, 1H), 7.49-7.76 (m, 1H), 7.47-7.49 (m, 1H), 3.75 (s, 3H), 3.48-3.53 (m, 3H), 3.34 (s, 3H), 2.74-2.90 (m, 1H), 2.68-2.74 (m, 1H).

60C: methyl 3-(3-amino-4-bromophenyl)-4-methoxybutanoate (Absolute Stereochemistry not Determined)

To a stirred solution of 60B (4 g, 12.04 mmol) in MeOH (40 mL), iron (5.38 g, 96 mmol), ammonium chloride 5.15 g, 96 mmol) in Water (10 mL) was added. The reaction suspension was heated at 70° C. for 5 h. The reaction mixture was allowed to cool to room temperature and filtered through a pad of celite. The celite pad was washed with excess of methanol and concentrated under reduced pressure to afford brown colored oil. The oily compound was reconstituted in ethyl acetate (200 mL) and aqueous saturated sodium bicarbonate solution (200 mL). The organic layer was separated and the aqueous layer was re-extracted with ethyl acetate (2×200 mL). The combined organic extracts were washed with water (50 mL), brine (50 mL), dried over sodium sulphate, filtered and evaporated under reduced pressure to afford the 60C (brown oil, 1.4 g, 4.50 mmol, 40.7% yield). LC-MS Anal. Calc'd for 301.03. found [M+2] 303.2, $T_r$=1.570 min $C_{12}H_{16}BrNO_3$ (Method BB).

Chiral separation of 60C shown enantiomeric excess of 85%, resolved to gave 60C Enantiomer 1, $T_r$=6.21 min and 60C Enantiomer 2, $T_r$=7.28 min (Method BS).

60C Enantiomer 1 (1.1 g, 3.64 mmol, 30.2% yield), $T_r$=6.21 min (Method BS). LC-MS Anal. Calc'd for $C_{12}H_{16}BrNO_3$ 301.031. found [M+3] 304.0, $T_r$=2.157 min (Method U).

60D. methyl 3-(4-bromo-3-((2-ethylpyrimidin-5-yl)amino)phenyl)-4-methoxybutanoate (Absolute Stereochemistry not Determined)

60D was prepared using the 60C Enantiomer 1 and 5-bromo-2-ethyl pyrimidine following the procedure described for the synthesis of 46B. LC-MS Anal. Calc'd for $C_{19}H_{19}BrN_2O_3$ 402.058. found [M+3] 405.1, $T_r$=1.33 min (Method AA).

60E. methyl 3-(4-(2,4-dimethylthiazol-5-yl)-3-((2-ethylpyrimidin-5-yl)amino) phenyl)-4-methoxybutanoate (Absolute Stereochemistry not Determined)

60E was prepared using the 60D and 58E following the procedure described for the synthesis of 156H. LC-MS Anal. Calc'd for $C_{24}H_{25}N_3O_3S$ 435.162. found [M+H] 436.2, $T_r$=1.04 min (Method AA).

Example 60. (R)-3-(4-(2,4-dimethylthiazol-5-yl)-3-((2-ethylpyrimidin-5-yl)amino) Phenyl) pentanoic Acid (Absolute Stereochemistry not Determined)

Example 60 was prepared using the 60E and following the hydrolysis procedure described for the synthesis of Example 46. LC-MS Anal. Calc'd for $C_{23}H_{23}N_3O_3S$ 421.146. found [M+H] 422.2, $T_r$=1.024 min (Method O). $^1$H NMR (400 MHz, CD3OD) δ 7.31 (d, J=8.80 Hz, 2H), 7.22 (d, J=8.00 Hz, 2H), 7.07 (d, J=7.60 Hz, 1H), 6.71-6.73 (m, 2H), 3.44-3.50 (m, 2H), 3.24-3.33 (m, 4H), 2.67-2.71 (m, 1H), 2.49-2.53 (m, 4H), 2.11 (s, 3H).

Example 61

(R)-3-(4-(2,4-dimethylthiazol-5-yl)-3-((2-ethoxypyrimidin-5-yl)amino) phenyl)pentanoic Acid (Absolute Stereochemistry not Determined)

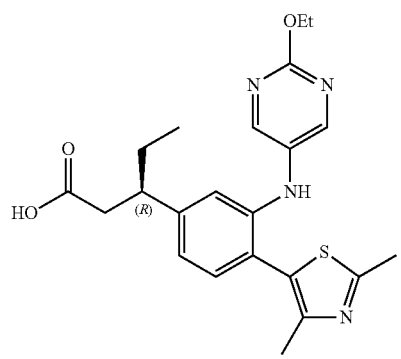

61A. methyl 3-(4-(5,5-dimethyl-1,3,2-dioxaborinan-2-yl)-3-((2-ethoxypyrimidin-5-yl)amino) phenyl) pentanoate (A0CAC1-347) (Absolute Stereochemistry not Determined)

A 100 mL three-neck round-bottomed flask equipped with a magnetic stirrer, reflux condenser and nitrogen inlet was charged with 46B (1.2 g, 2.94 mmol), 5,5,5',5'-tetramethyl-2,2'-bi(1,3,2-dioxaborinane) (1.992 g, 8.82 mmol), potassium acetate (0.865 g, 8.82 mmol) in 1,4-dioxane (15 mL). After bubbling nitrogen through the resulting suspension for 10 min, $PdCl_2$(dppf)-$CH_2Cl_2$ Adduct (0.120 g, 0.147 mmol) was added and again bubbled with nitrogen for another 5 min. The reaction mixture was heated at 110° C. for 12 h. The reaction mixture was cooled to room temperature and diluted with ethyl acetate (150 mL) and water (50 mL). Celite (2 g) was added, and the mixture was stirred for 5 min. The mixture was filtered through a pad of Celite, and the filtrate was washed with saturated aqueous sodium bicarbonate (30 mL), brine (30 mL), dried over sodium sulfate, filtered and concentrated under reduced pressure to afford 61A (brown solid, 1.18 g, 2.67 mmol, 91% yield). LC-MS Anal. Calc'd for $C_{23}H_{32}BN_3O_5$ 441.244. found 374.8, for parent boronic acid, $T_r$=1.608 min (Method BB).

Example 61. (R)-3-(4-(2,4-dimethylthiazol-5-yl)-3-((2-ethoxy pyrimidin-5-yl)amino)phenyl)pentanoic Acid (Absolute Stereochemistry not Determined)

To a stirred solution of 61A (20 mg, 0.045 mmol), potassium phosphate tribasic (19.24 mg, 0.091 mmol) and 5-bromo-2,4-dimethylthiazole (9.57 mg; 0.050 mmol) in Tetrahydrofuran (0.9 mL) and Water (0.1 mL), were purged with nitrogen for 15 min in a microwave vial. Then added 2-(dicyclohexylphosphino)-2',4',6'-triisopropylbiphenyl (4.32 mg, 9.06 μmol) and chloro (2-dicyclohexylphosphino-2',4',6'-triisopropyl-1,1'-biphenyl)[2-(2'-amino-1,1'-biphenyl)] palladium(II) (3.57 mg, 4.53 μmol), purged with nitrogen gas for another 5 min. The reaction mixture was irradiated with microwave radiation at 85° C. for 45 minutes in a microwave instrument. LCMS monitoring showed desired product mass (M+H)=441.3, $T_r$=2.73 min (Method O).

The solvent was evaporated under reduced pressure to afford the crude material, which was dissolved in mixture of THF (0.5 mL), Methanol (1 mL) and Water (0.25 mL), added $LiOH.H_2O$ (8.68 mg, 0.363 mmol) and the mixture was stirred at 50° C. for 2 h.

The organic solvents were evaporated under reduced pressure; aqueous solution was acidified to pH~3-4 with saturated citric acid solution, and extracted with ethyl acetate (2×10 mL). The combined organic layer was washed with water (10 mL), brine (10 mL), dried over anhydrous sodium sulfate, filtered and evaporated under reduced pressure to afford the crude material, which was purified via preparative reverse phase prep HPLC to afford Example 61 (off white solid, 3.8 mg, 0.089 mmol, 21%). LC-MS Anal. Calc'd for $C_{23}H_{32}BN_3O_5$ 426.17. found [M+H] 427.2, $T_r$=1.208 min (Method BB). $^1$H NMR (400 MHz, DMSO-d6) δ 8.23 (s, 2H), 7.30 (s, 1H), 7.14-7.20 (m, 1H), 6.94-6.95 (m, 1H), 6.82-6.84 (m, 1H), 4.26-4.27 (m, 2H), 2.79-2.82 (m, 1H), 2.59 (s, 3H), 2.49-2.55 (m, 2H), 2.16 (s, 3H), 1.29-1.32 (m, 2H), 1.30 (t, J=6.80 Hz, 3H), 0.75 (t, J=7.60 Hz, 3H).

Examples 62-89

Homochiral

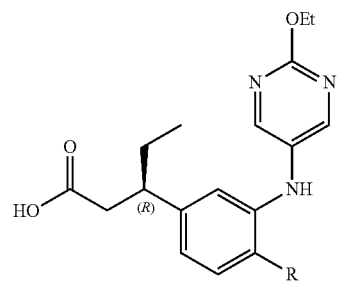

Examples 62-89 were prepared using the 59A and corresponding aryl/hetero aryl halides following the procedure described for the synthesis of Example 59.

| Ex. No. | Name | R | $T_R$ (min) | [M + H]$^+$ |
|---|---|---|---|---|
| 62 | (R)-3-(4-(5-cyanopyridin-2-yl)-3-((2-ethoxypyrimidin-5-yl)amino)phenyl) pentanoic acid (absolute stereochemistry not determined) | pyridine with CN | 1.403 Method O | 418.2 |
| 63 | (R)-3-(3-((2-ethoxypyrimidin-5-yl)amino)-4-(5-fluoropyrimidin-2-yl)phenyl) pentanoic acid (absolute stereochemistry not determined) | pyrimidine with F | 1.392 Method O | 412.2 |
| 64 | (R)-3-(4-(2-ethoxypyrimidin-5-yl)-3-((2-ethoxypyrimidin-5-yl)amino)phenyl) pentanoic acid (absolute stereochemistry not determined) | pyrimidine with OEt | 1.167 Method O | 438.3 |

-continued

| Ex. No. | Name | R | $T_R$ (min) | [M + H]⁺ |
|---|---|---|---|---|
| 65 | (R)-3-(3-((2-ethoxypyrimidin-5-yl)amino)-4-(2-methylbenzo[d]oxazol-6-yl)phenyl)pentanoic acid (absolute stereochemistry not determined) | 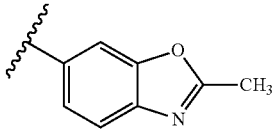 [SMILES: *c1ccc2nc(C)oc2c1] | 1.265 Method O | 447.2 |
| 66 | (R)-3-(4-(6-(difluoromethyl)pyridin-2-yl)-3-((2-ethoxypyrimidin-5-yl)amino)phenyl)pentanoic acid (absolute stereochemistry not determined) | 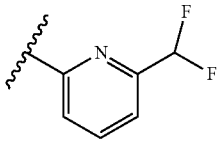 [SMILES: *c1cccc(C(F)F)n1] | 1.514 Method O | 443.2 |
| 67 | (R)-3-(3-((2-ethoxypyrimidin-5-yl)amino)-4-(1H-pyrrolo[2,3-c]pyridin-3-yl)phenyl)pentanoic acid (absolute stereochemistry not determined) | 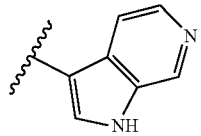 [SMILES: *c1c[nH]c2cnccc12] | 0.891 Method O | 432.2 |
| 68 | (R)-3-(3-((2-ethoxypyrimidin-5-yl)amino)-4-(2-methylbenzo[d]thiazol-6-yl)phenyl)pentanoic acid (absolute stereochemistry not determined) | 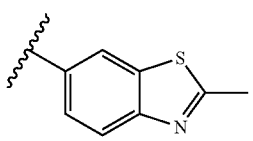 [SMILES: *c1ccc2nc(C)sc2c1] | 1.375 Method O | 463.2 |
| 69 | (R)-3-(3-((2-ethoxypyrimidin-5-yl)amino)-4-(5-methylpyrimidin-2-yl)phenyl)pentanoic acid (absolute stereochemistry not determined) | 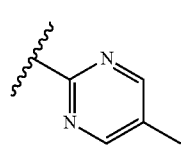 [SMILES: *c1ncc(C)cn1] | 1.375 Method O | 408.2 |
| 70 | (R)-3-(4'-chloro-2-((2-ethoxypyrimidin-5-yl)amino)-2'-fluoro-[1,1'-biphenyl]-4-yl)pentanoic acid (absolute stereochemistry not determined) | 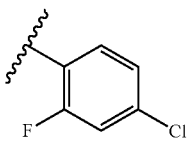 | 1.717 Method O | 444.2 |
| 71 | (R)-3-(4'-chloro-2-((2-ethoxypyrimidin-5-yl)amino)-[1,1'-biphenyl]-4-yl)pentanoic acid (absolute stereochemistry not determined) | 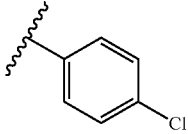 [SMILES: *c1ccc(Cl)cc1] | | |
| 72 | (R)-3-(4'-chloro-2-((2-ethoxypyrimidin-5-yl)amino)-3'-fluoro-[1,1'-biphenyl]-4-yl)pentanoic acid (absolute stereochemistry not determined) | 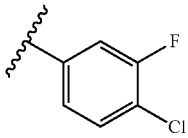 [SMILES: *c1ccc(Cl)c(F)c1] | 1.661 Method O | 444.2 |
| 73 | (R)-3-(4-(2,4-dimethylthiazol-5-yl)-3-((2-ethoxypyrimidin-5-yl)amino)phenyl)pentanoic acid (absolute stereochemistry not determined) | 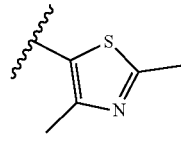 [SMILES: *c1sc(C)nc1C] | 1.208 Method O | 427.2 |
| 74 | (R)-3-(4-(5-ethoxypyrazin-2-yl)-3-((2-ethoxypyrimidin-5-yl)amino)phenyl)pentanoic acid (absolute stereochemistry not determined) | 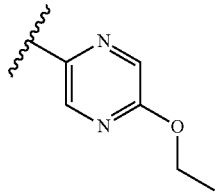 [SMILES: *c1cnc(OCC)cn1] | 1.535 Method O | 438.3 |

| Ex. No. | Name | R | T_R (min) | [M + H]+ |
|---|---|---|---|---|
| 75 | (R)-3-(4-(3,5-dimethyl-1H-pyrazol-4-yl)-3-((2-ethoxypyrimidin-5-yl)amino)phenyl)pentanoic acid (absolute stereochemistry not determined) | | 0.993 Method O | 410.3 |
| 76 | (R)-3-(4-(benzo[d]thiazol-2-yl)-3-((2-ethoxypyrimidin-5-yl)amino)phenyl)pentanoic acid (absolute stereochemistry not determined) | | 1.994 Method O | 449.2 |
| 77 | (R)-3-(3-((2-ethoxypyrimidin-5-yl)amino)-4-(imidazo[1,2-a]pyridin-2-yl)phenyl)pentanoic acid (absolute stereochemistry not determined) | | 1.006 Method O | 432.2 |
| 78 | (R)-3-(4-(benzo[c][1,2,5]oxadiazol-5-yl)-3-((2-ethoxypyrimidin-5-yl)amino)phenyl)pentanoic acid (absolute stereochemistry not determined) | | 1.392 Method O | 434.2 |
| 79 | (R)-3-(3-((2-ethoxypyrimidin-5-yl)amino)-4-(pyrazolo[1,5-a]pyrimidin-5-yl)phenyl)pentanoic acid (absolute stereochemistry not determined) | | 1.254 Method O | 433.2 |
| 80 | (R)-3-(4'-cyano-2-((2-ethoxypyrimidin-5-yl)amino)-3'-methoxy-[1,1'-biphenyl]-4-yl)pentanoic acid (absolute stereochemistry not determined) | | 1.845 Method O | 447.2 |
| 81 | (R)-3-(3-((2-ethoxypyrimidin-5-yl)amino)-4-(1,3,5-trimethyl-1H-pyrazol-4-yl)phenyl)pentanoic acid (absolute stereochemistry not determined) | | 1.099 Method O | 424.3 |
| 82 | (R)-3-(3-((2-ethoxypyrimidin-5-yl)amino)-4-(2-phenylthiazol-4-yl)phenyl)pentanoic acid (absolute stereochemistry not determined) | | 2.023 Method O | 475.2 |
| 83 | (R)-3-(4-(2,2-difluorobenzo[d][1,3]dioxol-5-yl)-3-((2-ethoxypyrimidin-5-yl)amino)phenyl)pentanoic acid (absolute stereochemistry not determined) | | 1.779 Method O | 472.2 |

| Ex. No. | Name | R | $T_R$ (min) | $[M + H]^+$ |
|---|---|---|---|---|
| 84 | (R)-3-(3-((2-ethoxypyrimidin-5-yl)amino)-4-(2-morpholinopyrimidin-4-yl)phenyl)pentanoic acid (absolute stereochemistry not determined) | | 1.471 Method O | 479.3 |
| 85 | (R)-3-(3-((2-ethoxypyrimidin-5-yl)amino)-4-(imidazo[1,5-a]pyridin-6-yl)phenyl)pentanoic acid (absolute stereochemistry not determined) | | 1.100 Method O | 432.3 |
| 86 | (R)-3-(3-((2-ethoxypyrimidin-5-yl)amino)-4-(imidazo[1,2-a]pyridin-7-yl)phenyl)pentanoic acid (absolute stereochemistry not determined) | | 0.992 Method O | 432.2 |
| 87 | (R)-3-(3-((2-ethoxypyrimidin-5-yl)amino)-4-(4-phenylthiazol-2-yl)phenyl)pentanoic acid (absolute stereochemistry not determined) | | 1.981 Method O | 475.2 |
| 88 | (R)-3-(3-((2-ethoxypyrimidin-5-yl)amino)-4-(4-methylthiazol-2-yl)phenyl)pentanoic acid (absolute stereochemistry not determined) | | 1.625 Method O | 413.2 |
| 89 | (R)-3-(3-((2-ethoxypyrimidin-5-yl)amino)-4-(5-methyl-1,3,4-thiadiazol-2-yl)phenyl)pentanoic acid (absolute stereochemistry not determined) | | 1.278 Method O | 414.2 |

Exemplary compounds were tested for inhibition of IDO activity. Experimental procedures and results are provided below.

Assessment of Inhibitor Activity in HeLa Cell-Based Indoleamine 2,3-Dioxygenase (IDO) Assay.

HeLa (ATCCR CCL-2) cells were obtained from the ATCC® and cultured in Dulbecco's Modified Eagle Medium supplemented with 4.5 g/L glucose, 4.5 g/L L-glutamine and 4.5 g/L sodium pyruvate (#10-013-CV, Corning), 2 mM L-alanyl-L-glutamine dipeptide (#35050-061, Gibco), 100U/mL penicillin, 100 g/mL streptomycin (#SV30010, HyClone) and 10% fetal bovine serum (#SH30071.03 HyClone). Cells were maintained in a humidified incubator at 37° C. in 5% $CO_2$.

IDO activity was assessed as a function of kynurenine production as follows: HeLa cells were seeded in a 96-well culture plate at a density of 5,000 cells/well and allowed to equilibrate overnight. After 24 hours, the media was aspirated and replaced with media containing IFNγ (#285-IF/CF, R&D Systems) at a final concentration of 25 ng/mL. A serial dilution of each test compound was added to the cells in a total volume of 200 μL of culture medium. After a further 48 hour incubation, 170 μL of supernatant was transferred from each well to a fresh 96-well plate. 12.1 μL of 6. IN trichloroacetic acid (#T0699, Sigma-Aldrich) was added to each well and mixed, followed by incubation at 65° C. for 20 minutes to hydrolyze N-formylkynurenine, the product of indoleamine 2,3-dioxygenase, to kynurenine. The reaction mixture was then centrifuged for 10 mins at 500×g to sediment the precipitate. 100 μL of the supernatant was transferred from each well to a fresh 96-well plate. 100 μl of 2% (w/v) p-dimethylaminobenzaldehyde (#15647-7, Sigma-Aldrich) in acetic acid (#A6283, Sigma-Aldrich) was added to each well mixed and incubated at room temperature for 20 mins. Kynurenine concentrations were determined by measuring absorbance at 480 nm and calibrating against an L-kynurenine (#K8625, Sigma-Aldrich) standard curve using a SPECTRAMAX® M2e microplate reader (Molecular Devices). The percentage activity at each inhibitor concentration was determined and $IC_{50}$ values assessed using nonlinear regression.

Activity for compounds described herein is provided in FIG. 1, wherein potency levels are provided as follows: (Potency: IDO $IC_{50}$: A<0.01 μM; B<0.1 μM; C<10 μM)

Assessment of Inhibitor Activity in HEK293 Cell-Based Indoleamine 2,3-Dioxygenase (IDO) Assay.

HEK293 cells were transfected with a pCDNA-based mammalian expression vector harboring human IDO1 cDNA (NM 002164.2) by electroporation. They were cultured in medium (DMEM with 10% FBS) containing 1 mg/ml G418 for two weeks. Clones of HEK293 cells that stably expressed human IDO1 protein were selected and expanded for IDO inhibition assay.

The human IDO1/HEK293 cells were seeded at 10,000 cells per 50 μL per well with RPMI/phenol red free media contains 10% FBS in a 384-well black wall clear bottom tissue culture plate (Matrix Technologies LLC) 100 nL of certain concentration of compound was then added to each well using ECHO liquid handling systems. The cells were incubated for 20 hours in 37° C. incubator with 5% $CO_2$.

The compound treatments were stopped by adding trichloroacetic acid (Sigma-Aldrich) to a final concentration at 0.2%. The cell plate was further incubated at 50° C. for 30 minute. The equal volume supernatant (20 μL) and 0.2% (w/v) Ehrlich reagent (4-dimethylaminobenzaldehyde, Sigma-Aldrich) in glacial acetic acid were mixed in a new clear bottom 384-well plate. This plate was then incubated at room temperature for 30 minute. The absorbance at 490 nm was measured on Envision plate reader.

Compound $IC_{50}$ values were calculated using the counts of 500 nM of a reference standard treatment as one hundred percent inhibition, and counts of no compound but DMSO treatment as zero percent inhibition.

Activity for compounds described herein is provided in FIG. 1, wherein potency levels are provided as follows: (Potency: IDO $IC_{50}$: A<0.01 μM; B<0.1 μM; C<10 μM).

| example # | IDO1 HEK Human IC50 (uM) | A < 50, B < 250, C < 2000 | IDO Hela IC50 (uM) | A < 50, B < 250, C < 2000 |
|---|---|---|---|---|
| 1-1 | 0.499 | C | | |
| 1-2 | 1.596 | C | | |
| 2-3 | 0.001 | A | 0.00 | A |
| 1-4 | 0.003 | A | 0.00 | A |
| 2 | | | 0.01 | A |
| 3 | | | 0.04 | A |
| 4 | | | 0.01 | A |
| 5 | | | 0.11 | B |
| 6 | | | 0.47 | C |
| 7 | | | 1.00 | C |
| 8 | | | 0.38 | C |
| 9 | | | 0.02 | A |
| 10 | | | 0.04 | A |
| 11 | | | 1.00 | C |
| 12 | | | 1.00 | C |
| 13 | | | 1.00 | C |
| 14 | | | 0.04 | A |
| 15 | | | 1.00 | C |
| 16 | | | 1.00 | C |
| 17 | | | 0.01 | A |
| 18 | | | 0.07 | B |
| 19 | | | 1.00 | C |
| 20 | | | 0.03 | A |
| 21 | | | 1.00 | C |
| 22 | | | 0.03 | A |
| 23 | | | 1.00 | C |
| 24 | | | 1.00 | C |
| 25 | | | 0.02 | A |
| 26 | | | 0.02 | A |
| 27 | | | 0.82 | C |
| 28 | | | 0.76 | C |
| 29 | | | 0.13 | B |
| 30 | | | 0.00 | A |
| 31 | | | 0.02 | A |
| 32 | | | 0.00 | A |
| 33 | | | 1.00 | C |
| 34 | | | 0.32 | C |
| 35 | | | 0.01 | A |
| 36 | | | 0.03 | A |
| 37 | | | 1.00 | C |
| 38 | | | 0.05 | B |
| 39 | | | 0.02 | A |
| 40 | | | 0.09 | B |
| 41 | | | 0.43 | C |
| 43 | | | 1.00 | C |
| 44 | | | 0.45 | C |
| 45 | | | 0.05 | B |
| 46 | | | 0.04 | A |
| 47 | | | 0.01 | A |
| 48 | | | 0.34 | C |
| 49 | | | 0.03 | A |
| 50 | | | 1.00 | C |
| 51 | | | 0.15 | B |
| 52 | | | 1.00 | C |
| 53 | | | 0.03 | A |
| 54 | | | 0.09 | B |
| 55 | | | 1.00 | C |
| 56 | | | 0.39 | C |
| 57 | | | 0.11 | B |
| 58 | | | 0.39 | C |
| 59 | | | 0.22 | B |
| 60 | | | 0.02 | A |
| 61 | | | 0.01 | A |
| 62 | | | 0.89 | C |
| 63 | | | 0.70 | C |
| 64 | | | 1.00 | C |
| 65 | | | 1.00 | C |
| 66 | | | 0.75 | C |
| 67 | | | 1.00 | C |
| 68 | | | 0.50 | C |
| 69 | | | 0.11 | B |
| 70 | | | 0.23 | B |
| 71 | | | 0.11 | B |
| 72 | | | 0.21 | B |
| 74 | | | 0.45 | C |
| 75 | | | 1.00 | C |
| 76 | | | 0.95 | C |
| 77 | | | 1.00 | C |
| 78 | | | 1.00 | C |
| 79 | | | 0.40 | C |
| 80 | | | 1.00 | C |
| 81 | | | 0.60 | C |
| 82 | | | 0.11 | B |
| 83 | | | 0.17 | B |
| 84 | | | 0.76 | C |
| 85 | | | 1.00 | C |
| 86 | | | 1.00 | C |
| 87 | | | 1.00 | C |
| 89 | | | 0.40 | C |

What is claimed:

1. A compound of formula I or II

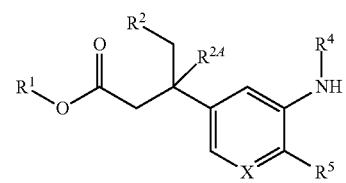

I

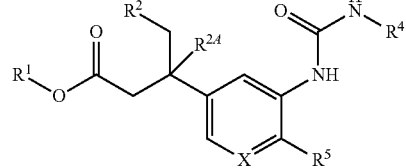

II wherein
X is CH or N;
$R^1$ is H or $C_{1-6}$alkyl;

$R^2$ is H, $C_{1-6}$alkyl, or $C_{0-6}$alk-$OC_{1-6}$alkyl;
$R^{2A}$ is H or $C_{1-6}$alkyl;
$R^5$ is
  phenyl optionally substituted with one, two or three substituents independently selected from halogen, $C_{0-6}$alk-O—$C_{1-6}$alkyl, or —CN;
  heteroaryl optionally substituted with one, two or three substituents independently selected from halogen, optionally substituted phenyl, optionally substituted benzyl, optionally substituted $C_{1-6}$alkyl, $C_{1-6}$haloalkyl, $C_{0-6}$alk-O—$C_{1-6}$alkyl, heterocyclyl, or CN;

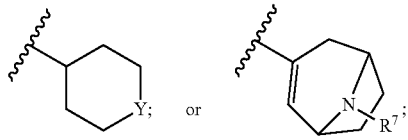

Y is O, $CHR^6$, or $NR^7$;
$R^6$ is H or phenyl;
$R^7$ is H, pyridyl, pyrazinyl, pyridazinyl, pyrimidyl, —COOH, —COO$C_{1-6}$alkyl, or COR$^{7A}$
  wherein $R^{7A}$ is H, $C_{1-6}$alkyl, pyridyl optionally substituted with O$C_{1-6}$alkyl, pyrazinyl optionally substituted with O$C_{1-6}$alkyl, pyridazinyl optionally substituted with O$C_{1-6}$alkyl, or pyrimidyl optionally substituted with O$C_{1-6}$alkyl; and
$R^4$ is phenyl, pyridyl, pyrazinyl, pyridazinyl, pyrimidyl, or benzothiazolyl, optionally substituted with one, two or three substituents independently selected from halogen, $C_{1-6}$alkyl, $C_{1-6}$haloalkyl, O$C_{1-6}$haloalkyl, $C_{0-6}$alk-O—$C_{1-6}$alkyl, —CN, —COOH, and —COO$C_{1-6}$alkyl, or a pharmaceutically acceptable salt thereof or solvate thereof.

2. The compound of claim 1, wherein X is CH.
3. The compound of claim 1, wherein X is N.
4. The compound of claim 1, wherein $R^1$ is H.
5. The compound of claim 1, wherein $R^1$ is $C_{1-6}$alkyl.
6. The compound of claim 1, wherein $R^1$ is H.
7. The compound of claim 1, wherein $R^1$ is $C_{1-6}$alkyl.
8. The compound of claim 1, wherein $R^1$ is $C_{0-6}$alk-O$C_{1-6}$alkyl.
9. The compound of claim 1, wherein $R^{2A}$ is H.
10. The compound of claim 1, wherein $R^{2A}$ is $C_{1-6}$alkyl.
11. The compound of claim 1, wherein $R^5$ is phenyl optionally substituted with one, two or three substituents independently selected from halogen, $C_0$-balk-O—$C_{1-6}$alkyl, or —CN.
12. The compound of claim 11, wherein $R^5$ is 4-chlorophenyl, 4-chloro-2-fluorophenyl, 4-chloro-3-fluorophenyl, 3-fluoro-4-methoxyphenyl, 2-fluoro-4-methoxyphenyl, or 4-cyano-3-methoxyphenyl.
13. The compound of claim 1, wherein $R^5$ is heteroaryl optionally substituted with one, two or three substituents independently selected from halogen, optionally substituted phenyl, optionally substituted benzyl, optionally substituted $C_{1-6}$alkyl, $C_{1-6}$haloalkyl, $C_0$-6alk-O—$C_{1-6}$alkyl, heterocyclyl, and —CN.
14. The compound of claim 13, wherein $R^5$ is 1H-pyrazol-4-yl, thiazol-2-yl, furan-3-yl, benzo[d][1,3]dioxol-5-yl, 2,3-dihydrobenzofuran-5-yl, benzofuran-5-yl, benzo[b]thiophen-5-yl, pyrimidin-5-yl, 1H-indazol-4-yl, 1H-pyrrolo[2,3-c]pyridin-3-yl, benzo[d]thiazol-2-yl, imidazo[1,2-a]pyridin-2-yl, benzo[c][1,2,5]oxadiazol-5-yl, pyrazolo[1,5-a]pyrimidin-5-yl, imidazo[1,5-a]pyridin-6-yl, imidazo[1,2-a]pyridin-7-yl, 3-fluoropyridin-4-yl, 5-fluoropyrimidin-2-yl, 2,2-difluorobenzo[d][1,3]dioxol-5-yl, 4-phenylthiazol-2-yl, 1-(4-fluorophenyl)-1H-pyrazol-4-yl, 2-phenylthiazol-4-yl, 4-phenylthiazol-2-yl, 1-benzyl-1H-pyrazol-4-yl, 1-(4-methoxybenzyl)-1H-pyrazol-4-yl, 1-methyl-1H-pyrazol-4-yl, 3,5-dimethylisoxazol-4-yl, 4-methylthiazol-2-yl, 5-methyl-1,3,4-thiadiazol-2-yl, 1-isopropyl-1H-pyrazol-4-yl, 1-methyl-1H-indazol-5-yl, 3,5-dimethylisoxazol-4-yl, 2,4-dimethylthiazol-5-yl, 2-methylbenzo[d]oxazol-6-yl, 2-methylbenzo[d]thiazol-6-yl, 5-methylpyrimidin-2-yl, 3,5-dimethyl-1H-pyrazol-4-yl, 1,3,5-trimethyl-1H-pyrazol-4-yl, 4-methylthiazol-2-yl, 5-methyl-1,3,4-thiadiazol-2-yl, 1-(2-morpholinoethyl)-1H-pyrazol-4-yl, 6-(difluoromethyl)pyridin-2-yl, 2-ethoxypyrimidin-5-yl, 5-ethoxypyrazin-2-yl, 2-morpholinopyrimidin-4-yl, or 5-cyanopyridin-2-yl.

15. The compound of claim 1, wherein $R^5$ is

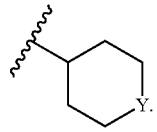

16. The compound of claim 15, wherein Y is O.
17. The compound of claim 15, wherein Y is $CHR^6$.
18. The compound of claim 17, wherein $R^6$ is phenyl.
19. The compound of claim 15, wherein Y is $NR^7$.
20. The compound of claim 19, wherein $R^7$ is tert-butoxycarbonyl.
21. The compound of claim 1, wherein $R^5$ is

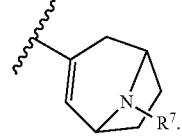

22. The compound of claim 21, wherein $R^7$ is tert-butoxycarbonyl.
23. The compound of claim 1, wherein $R^4$ is phenyl optionally substituted with one, two or three substituents independently selected from halogen, $C_{1-6}$alkyl, $C_{1-6}$haloalkyl, O$C_{1-6}$haloalkyl, $C_{0-6}$alk-O—$C_{1-6}$alkyl, —CN, —COOH, and —COO$C_{1-6}$alkyl.
24. The compound of claim 23, wherein the $R^4$ is 4-fluorophenyl, 4-chlorophenyl, 3-chlorophenyl, 3-fluorophenyl, 4-chloro-3-fluorophenyl, 4-chloro-2-fluorophenyl, 4-(trifluoromethyl)phenyl, or 4-cyanophenyl.
25. The compound of claim 1, wherein $R^4$ is pyridyl optionally substituted with one, two or three substituents independently selected from halogen, $C_{1-6}$alkyl, $C_{1-6}$haloalkyl, O$C_{1-6}$haloalkyl, $C_0$-balk-O—$C_{1-6}$alkyl, —CN, —COOH, and —COO$C_{1-6}$alkyl.
26. The compound of claim 25, wherein $R^4$ is pyridin-3-yl, pyridin-2-yl, 5-chloropyridin-2-yl, or 5-cyanopyridin-2-yl.
27. The compound of claim 1, wherein $R^4$ is pyrazinyl optionally substituted with one, two or three substituents independently selected from halogen, $C_{1-6}$alkyl, $C_{1-6}$haloalkyl, O$C_{1-6}$haloalkyl, $C_0$-balk-O—$C_{1-6}$alkyl, —CN, —COOH, and —COO$C_{1-6}$alkyl.
28. The compound of claim 1, wherein $R^4$ is pyridazinyl optionally substituted with one, two or three substituents independently selected from halogen, $C_{1-6}$alkyl, $C_{1-6}$haloalkyl, $OC_{1-6}$haloalkyl, $Co$-balk-$O$—$C_{1-6}$alkyl, —CN, —COOH, and —COOC$_{1-6}$alkyl.

29. The compound of claim 1, wherein $R^4$ is pyrimidyl optionally substituted with one, two or three substituents independently selected from halogen, $C_{1-6}$alkyl, $C_{1-6}$haloalkyl, $OC_{1-6}$haloalkyl, $Co$-balk-$O$—$C_{1-6}$alkyl, —CN, —COOH, and —COOC$_{1-6}$alkyl.

30. The compound according to claim 29, wherein $R^4$ is 2-methylpyrimidin-5-yl, 2-ethylpyrimidin-5-yl, or 2-ethoxypyrimidin-5-yl.

31. The compound of claim 1, wherein $R^4$ is benzothiazolyl optionally substituted with one, two or three substituents independently selected from halogen, $C_{1-6}$alkyl, $C_{1-6}$haloalkyl, $OC_{1-6}$haloalkyl, $Co$-balk-$O$—$C_{1-6}$alkyl, —CN, —COOH, and —COOC$_{1-6}$alkyl.

32. The compound of claim 1 that is
(S)-3-(4-((1s,4R)-4-phenylcyclohexyl)-3-(3-(p-tolyl)ureido)phenyl)pentanoic acid;
(S)-3-(4-((1r,4S)-4-phenylcyclohexyl)-3-(3-(p-tolyl)ureido)phenyl)pentanoic acid;
(R)-3-(4-((1s,4S)-4-phenylcyclohexyl)-3-(3-(p-tolyl)ureido)phenyl)pentanoic acid;
(R)-3-(4-((1r,4R)-4-phenylcyclohexyl)-3-(3-(p-tolyl)ureido)phenyl)pentanoic acid;
3-(4-(4-phenylcyclohexyl)-3-(3-(p-tolyl)ureido)phenyl)pentanoic acid;
(R)-3-(3-((4-chloro-2-fluorophenyl)amino)-4-(1-methyl-1H-pyrazol-4-yl)phenyl)pentanoic acid;
(R)-3-(3-((4-chloro-2-fluorophenyl)amino)-4-(1-methyl-1H-pyrazol-4-yl)phenyl)pentanoic acid;
(R)-3-(3-((4-fluorophenyl)amino)-4-(1-methyl-1H-pyrazol-4-yl)phenyl)pentanoic acid;
(R)-3-(3-((4-chlorophenyl)amino)-4-(1-methyl-1H-pyrazol-4-yl)phenyl)pentanoic acid;
(R)-3-(3-((4-cyanophenyl)amino)-4-(1-methyl-1H-pyrazol-4-yl)phenyl)pentanoic acid;
(R)-3-(3-((5-chloropyridin-2-yl)amino)-4-(1-methyl-1H-pyrazol-4-yl)phenyl)pentanoic acid;
(R)-3-(3-((3-chlorophenyl)amino)-4-(1-methyl-1H-pyrazol-4-yl)phenyl)pentanoic acid;
(R)-3-(3-((3-fluorophenyl)amino)-4-(1-methyl-1H-pyrazol-4-yl)phenyl)pentanoic acid;
(R)-3-(3-((4-chloro-3-fluorophenyl)amino)-4-(1-methyl-1H-pyrazol-4-yl)phenyl)pentanoic acid;
(R)-3-(4-(1-methyl-1H-pyrazol-4-yl)-3-(p-tolylamino)phenyl)pentanoic acid;
(R)-3-(4-(1-methyl-1H-pyrazol-4-yl)-3-(pyridin-3-ylamino)phenyl)pentanoic acid;
(R)-3-(4-(1-methyl-1H-pyrazol-4-yl)-3-((2-methylpyrimidin-5-yl)amino)phenyl)pentanoic acid;
(R)-3-(3-((2-ethylpyrimidin-5-yl)amino)-4-(1-methyl-1H-pyrazol-4-yl)phenyl)pentanoic acid;
(R)-3-(4-(1-methyl-1H-pyrazol-4-yl)-3-((4-(trifluoromethyl)phenyl)amino)phenyl)pentanoic acid;
(R)-3-(4-(1-methyl-1H-pyrazol-4-yl)-3-(pyridin-2-ylamino)phenyl)pentanoic acid;
(R)-3-(3-((5-cyanopyridin-2-yl)amino)-4-(1-methyl-1H-pyrazol-4-yl)phenyl)pentanoic acid;
(R)-3-(3-((4-chlorophenyl)amino)-4-(3,5-dimethylisoxazol-4-yl)phenyl)pentanoic acid;
(R)-3-(3-((4-chlorophenyl)amino)-4-(3,5-dimethylisoxazol-4-yl)phenyl)pentanoic acid;
(R)-3-(3-((4-chlorophenyl)amino)-4-(1H-pyrazol-4-yl)phenyl)pentanoic acid;
(R)-3-(3-((4-chlorophenyl)amino)-4-(4-methylthiazol-2-yl)phenyl)pentanoic acid;
(R)-3-(3-((4-chlorophenyl)amino)-4-(4-phenylthiazol-2-yl)phenyl)pentanoic acid;
(R)-3-(3-((4-chlorophenyl)amino)-4-(thiazol-2-yl)phenyl)pentanoic acid;
(R)-3-(3-((4-chlorophenyl)amino)-4-(5-methyl-1,3,4-thiadiazol-2-yl)phenyl)pentanoic acid;
(R)-3-(3-(3-(4-chloro-2-fluorophenyl)ureido)-4-(1-methyl-1H-pyrazol-4-yl)phenyl)pentanoic acid;
(R)-3-(3-(3-(4-chloro-2-fluorophenyl)ureido)-4-(1-methyl-1H-pyrazol-4-yl)phenyl)pentanoic acid;
(R)-3-(3-(3-(4-chloro-2-fluorophenyl)ureido)-4-(1-isopropyl-1H-pyrazol-4-yl)phenyl)pentanoic acid;
(R)-3-(3-(3-(4-chloro-2-fluorophenyl)ureido)-4-(1-isopropyl-1H-pyrazol-4-yl)phenyl)pentanoic acid;
(R)-3-(4-(1-(tert-butoxycarbonyl)piperidin-4-yl)-3-((2-ethoxypyrimidin-5-yl)amino)phenyl) pentanoic acid;
(S)-3-(4-(1-(tert-butoxycarbonyl)piperidin-4-yl)-3-((2-ethoxypyrimidin-5-yl)amino)phenyl) pentanoic acid;
(S)-3-(4-(1-(tert-butoxycarbonyl)piperidin-4-yl)-3-((2-ethoxypyrimidin-5-yl)amino)phenyl) pentanoic acid;
(S)-3-(4-(1-(tert-butoxycarbonyl)piperidin-4-yl)-3-((2-ethoxypyrimidin-5-yl)amino)phenyl) pentanoic acid;
(R)-3-(4-(1-(tert-butoxycarbonyl)piperidin-4-yl)-3-((2-methylpyrimidin-5-yl)amino)phenyl) pentanoic acid;
(S)-3-(4-(1-(tert-butoxycarbonyl)piperidin-4-yl)-3-((2-methylpyrimidin-5-yl)amino)phenyl) pentanoic acid;
(R)-3-(4-(1-(tert-butoxycarbonyl)piperidin-4-yl)-3-((2-methylpyrimidin-5-yl)amino)phenyl) pentanoic acid;
(R)-3-(4-(1-(tert-butoxycarbonyl)piperidin-4-yl)-3-((2-ethylpyrimidin-5-yl)amino)phenyl) pentanoic acid;
(R)-3-(4-(1-(tert-butoxycarbonyl)piperidin-4-yl)-3-((4-cyanophenyl)amino)phenyl)pentanoic acid;
(S)-3-(4-(1-(tert-butoxycarbonyl)piperidin-4-yl)-3-((2-methylpyrimidin-5-yl)amino)phenyl) pentanoic acid;
(S)-3-(4-(1-(tert-butoxycarbonyl)piperidin-4-yl)-3-((2-methylpyrimidin-5-yl)amino)phenyl) pentanoic acid;
(S)-3-(4-(1-(tert-butoxycarbonyl)piperidin-4-yl)-3-((2-ethylpyrimidin-5-yl)amino)phenyl) pentanoic acid;
(S)-3-(4-(1-(tert-butoxycarbonyl)piperidin-4-yl)-3-((4-cyanophenyl)amino)phenyl)pentanoic acid;
(S)-3-(3-((4-cyanophenyl) amino)-4-(1-methyl-1H-pyrazol-4-yl) phenyl)-4-methoxybutanoic acid;
(R)-3-(3-((4-cyanophenyl) amino)-4-(1-methyl-1H-pyrazol-4-yl) phenyl)-4-methoxybutanoic acid;
(S)-3-(3-((4-cyanophenyl) amino)-4-(1-methyl-1H-pyrazol-4-yl)phenyl)-4-methoxybutanoic acid;
(R)-3-(3-((4-cyanophenyl)amino)-4-(1-methyl-1H-pyrazol-4-yl)phenyl)-4-methoxybutanoic acid;
(S)-3-(4-(benzo[d][1,3]dioxol-5-yl)-3-((4-cyanophenyl)amino)phenyl)-4-methoxybutanoic acid;
(S)-3-(3-((4-cyanophenyl)amino)-4-(furan-3-yl)phenyl)-4-methoxybutanoic acid;
(S)-3-(3-((4-cyanophenyl)amino)-4-(1-(4-methoxybenzyl)-1H-pyrazol-4-yl)phenyl)-4-methoxybutanoic acid;
(S)-3-(2-((4-cyanophenyl)amino)-methyl-[1,1'-biphenyl]-4-yl)-4-methoxybutanoic acid;
(R)-3-(4-(benzo[d][1,3]dioxol-5-yl)-3-((4-cyanophenyl)amino)phenyl)-4-methoxybutanoic acid;
(R)-3-(3-((4-cyanophenyl)amino)-4-(furan-3-yl)phenyl)-4-methoxybutanoic acid;
(R)-3-(3-((4-cyanophenyl)amino)-4-(2,3-dihydrobenzofuran-5-yl)phenyl)-4-methoxybutanoic acid;
(R)-3-(4-(benzofuran-2-yl)-3-((4-cyanophenyl)amino) phenyl)-4-methoxybutanoic acid;
(R)-3-(4-(benzo[b]thiophen-2-yl)-3-((4-cyanophenyl)amino)phenyl)-4-methoxybutanoic acid;

(R)-3-(3-((4-cyanophenyl)amino)-4-(pyrimidin-5-yl)phenyl)-4-methoxybutanoic acid
(R)-3-(4-(1-benzyl-1H-pyrazol-4-yl)-3-((4-cyanophenyl)amino)phenyl)-4-methoxybutanoic acid;
(R)-3-(3-((4-cyanophenyl)amino)-4-(1-(4-methoxybenzyl)-1H-pyrazol-4-yl)phenyl)-4-methoxybutanoic acid;
(R)-3-(3-((2-ethoxypyrimidin-5-yl)amino)-4-(furan-3-yl)phenyl)pentanoic acid;
(R)-3-(3-((2-ethoxypyrimidin-5-yl)amino)-4-(1-(4-methoxybenzyl)-1H-pyrazol-4-yl)phenyl) pentanoic acid;
(R)-3-(3-((2-ethoxypyrimidin-5-yl)amino)-4-(1-(4-fluorophenyl)-1H-pyrazol-4-yl)phenyl) pentanoic acid;
(R)-3-(2-((2-ethoxypyrimidin-5-yl)amino)-3'-fluoro-4'-methoxy-[1,1'-biphenyl]-4-yl)pentanoic acid;
(R)-3-(3-((2-ethoxypyrimidin-5-yl)amino)-4-(1H-indazol-4-yl)phenyl)pentanoic acid;
(R)-3-(3-((2-ethoxypyrimidin-5-yl)amino)-4-(1-methyl-1H-indazol-5-yl)phenyl)pentanoic acid;
(R)-3-(3-((2-ethoxypyrimidin-5-yl)amino)-4-(3-fluoropyridin-4-yl)phenyl)pentanoic acid;
(R)-3-(2-((2-ethoxypyrimidin-5-yl)amino)-2'-fluoro-4'-methoxy-[1,1'-biphenyl]-4-yl)pentanoic acid;
(R)-3-(4-(3,5-dimethylisoxazol-4-yl)-3-((2-ethoxypyrimidin-5-yl)amino)phenyl)pentanoic acid;
(R)-3-(3-((2-ethoxypyrimidin-5-yl)amino)-4-(1-(2-morpholinoethyl)-1H-pyrazol-4-yl)phenyl) pentanoic acid;
(R)-3-(4-(8-(tert-butoxycarbonyl)-8-azabicyclo[3.2.1]oct-2-en-3-yl)-3-((2-ethoxypyrimidin-5-yl)amino)phenyl)pentanoic acid;
(R)-3-(4-(2,4-dimethylthiazol-5-yl)-3-((2-ethylpyrimidin-5-yl)amino)phenyl)pentanoic acid;
(S)-3-(4-(2,4-dimethylthiazol-5-yl)-3-((2-ethylpyrimidin-5-yl)amino)phenyl)pentanoic acid;
(S)-3-(4-(2,4-dimethylthiazol-5-yl)-3-((2-ethylpyrimidin-5-yl)amino)phenyl)pentanoic acid;
(S)-3-(4-(2,4-dimethylthiazol-5-yl)-3-((2-ethylpyrimidin-5-yl)amino)phenyl)pentanoic acid;
(S)-3-(4-(2,4-dimethylthiazol-5-yl)-3-((2-ethylpyrimidin-5-yl)amino)phenyl)pentanoic acid;
(S)-3-(3-((4-cyanophenyl)amino)-4-(2,4-dimethylthiazol-5-yl)phenyl)-4-methoxybutanoic acid;
(R)-3-(4-(2,4-dimethylthiazol-5-yl)-3-((2-ethylpyrimidin-5-yl)amino)phenyl)pentanoic acid;
(R)-3-(4-(2,4-dimethylthiazol-5-yl)-3-((2-ethylpyrimidin-5-yl)amino) Phenyl) pentanoic acid;
(R)-3-(4-(2,4-dimethylthiazol-5-yl)-3-((2-ethoxypyrimidin-5-yl)amino)phenyl)pentanoic acid;
(R)-3-(4-(2,4-dimethylthiazol-5-yl)-3-((2-ethoxypyrimidin-5-yl)amino)phenyl)pentanoic acid;
(R)-3-(4-(5-cyanopyridin-2-yl)-3-((2-ethoxypyrimidin-5-yl)amino)phenyl)pentanoic acid;
(R)-3-(3-((2-ethoxypyrimidin-5-yl)amino)-4-(5-fluoropyrimidin-2-yl)phenyl)pentanoic acid;
(R)-3-(4-(2-ethoxypyrimidin-5-yl)-3-((2-ethoxypyrimidin-5-yl)amino)phenyl)pentanoic acid;
(R)-3-(3-((2-ethoxypyrimidin-5-yl)amino)-4-(2-methylbenzo[d]oxazol-6-yl)phenyl)pentanoic acid;
(R)-3-(4-(6-(difluoromethyl)pyridin-2-yl)-3-((2-ethoxypyrimidin-5-yl)amino)phenyl)pentanoic acid;
(R)-3-(3-((2-ethoxypyrimidin-5-yl)amino)-4-(1H-pyrrolo[2,3-c]pyridin-3-yl)phenyl)pentanoic acid;
(R)-3-(3-((2-ethoxypyrimidin-5-yl)amino)-4-(2-methylbenzo[d]thiazol-6-yl)phenyl)pentanoic acid;
(R)-3-(3-((2-ethoxypyrimidin-5-yl)amino)-4-(5-methylpyrimidin-2-yl)phenyl)pentanoic acid;

(R)-3-(4'-chloro-2-((2-ethoxypyrimidin-5-yl)amino)-2'-fluoro-[1,1'-biphenyl]-4-yl)pentanoic acid;
(R)-3-(4'-chloro-2-((2-ethoxypyrimidin-5-yl)amino)-[1,1'-biphenyl]-4-yl)pentanoic acid;
(R)-3-(4'-chloro-2-((2-ethoxypyrimidin-5-yl)amino)-3'-fluoro-[1,1'-biphenyl]-4-yl)pentanoic acid;
(R)-3-(4-(2,4-dimethylthiazol-5-yl)-3-((2-ethoxypyrimidin-5-yl)amino)phenyl)pentanoic acid;
(R)-3-(4-(5-ethoxypyrazin-2-yl)-3-((2-ethoxypyrimidin-5-yl)amino)phenyl)pentanoic acid;
(R)-3-(4-(3,5-dimethyl-1H-pyrazol-4-yl)-3-((2-ethoxypyrimidin-5-yl)amino)phenyl)pentanoic acid;
(R)-3-(4-(benzo[d]thiazol-2-yl)-3-((2-ethoxypyrimidin-5-yl)amino)phenyl)pentanoic acid;
(R)-3-(3-((2-ethoxypyrimidin-5-yl)amino)-4-(imidazo[1,2-a]pyridin-2-yl)phenyl)pentanoic acid;
(R)-3-(4-(benzo[c][1,2,5]oxadiazol-5-yl)-3-((2-ethoxypyrimidin-5-yl)amino)phenyl)pentanoic acid;
(R)-3-(3-((2-ethoxypyrimidin-5-yl)amino)-4-(pyrazolo[1,5-a]pyrimidin-5-yl)phenyl)pentanoic acid;
(R)-3-(4'-cyano-2-((2-ethoxypyrimidin-5-yl)amino)-3'-methoxy-[1,1'-biphenyl]-4-yl)pentanoic acid;
(R)-3-(3-((2-ethoxypyrimidin-5-yl)amino)-4-(1,3,5-trimethyl-1H-pyrazol-4-yl)phenyl)pentanoic acid;
(R)-3-(3-((2-ethoxypyrimidin-5-yl)amino)-4-(2-phenylthiazol-4-yl)phenyl)pentanoic acid;
(R)-3-(4-(2,2-difluorobenzo[d][1,3]dioxol-5-yl)-3-((2-ethoxypyrimidin-5-yl)amino)phenyl) pentanoic acid;
(R)-3-(3-((2-ethoxypyrimidin-5-yl)amino)-4-(2-morpholinopyrimidin-4-yl)phenyl)pentanoic acid;
(R)-3-(3-((2-ethoxypyrimidin-5-yl)amino)-4-(imidazo[1,5-a]pyridin-6-yl)phenyl)pentanoic acid;
(R)-3-(3-((2-ethoxypyrimidin-5-yl)amino)-4-(imidazo[1,2-a]pyridin-7-yl)phenyl)pentanoic acid;
(R)-3-(3-((2-ethoxypyrimidin-5-yl)amino)-4-(4-phenylthiazol-2-yl)phenyl)pentanoic acid;
(R)-3-(3-((2-ethoxypyrimidin-5-yl)amino)-4-(4-methylthiazol-2-yl)phenyl)pentanoic acid;
(R)-3-(3-((2-ethoxypyrimidin-5-yl)amino)-4-(5-methyl-1,3,4-thiadiazol-2-yl)phenyl)pentanoic acid;
or a pharmaceutically acceptable salt or solvate thereof.

33. A compound that is an enantiomer or a diastereomer of a compound of claim 32, or a pharmaceutically acceptable salt thereof.

34. A pharmaceutical composition comprising a compound of claim 1 and a pharmaceutically acceptable carrier.

35. The pharmaceutical composition of claim 34, further comprising at least one additional therapeutic agent.

36. The pharmaceutical composition of claim 35, wherein the additional therapeutic agent is an immuno-oncology agent.

37. The pharmaceutical composition of claim 36, wherein the immune-oncology agent is ipilimumab (YERVOY), nivolumab (OPDIVO), or pembrolizumab (KEYTRUDA), or a combination thereof.

38. A method of treating cancer in a patient in need of such treatment comprising administering to the patient a therapeutically effective amount of a compound according to claim 1; wherein the cancer is brain neoplasm, breast carcinoma, melanoma, pancreatic carcinoma, prostate carcinoma and solid tumors.

39. The method of claim 38, further comprising administering to the patient an additional therapeutic agent.

40. The method of claim 39, wherein the additional therapeutic agent is an immune-oncology agent.

41. The method of claim 40, wherein the immune-oncology agent is ipilimumab (YERVOY), nivolumab (OPDIVO), or pembrolizumab (KEYTRUDA), or a combination thereof.

42. The method of claim 38, wherein the patient is human.

\* \* \* \* \*

UNITED STATES PATENT AND TRADEMARK OFFICE
CERTIFICATE OF CORRECTION

| | | |
|---|---|---|
| PATENT NO. | : 10,959,986 B2 | Page 1 of 2 |
| APPLICATION NO. | : 16/555634 | |
| DATED | : March 30, 2021 | |
| INVENTOR(S) | : Balog et al. | |

It is certified that error appears in the above-identified patent and that said Letters Patent is hereby corrected as shown below:

In the Claims

At Column 103, Line 11 (Claim 1), delete "CN" and insert -- CN; -- therefor

At Column 103, Line 41 (Claim 6), delete "$R^1$" and insert -- $R^2$ -- therefor At Column 103, Line 42 (Claim 7), delete "$R^1$" and insert -- $R^2$ -- therefor At Column 103, Line 43 (Claim 8), delete "$R^1$" and insert -- $R^2$ -- therefor At Column 103, Line 49 (Claim 11), delete "Co-balk-O" and insert -- $C_{1-6}$alk-O -- therefor At Column 104, Line 56 (Claim 25), delete "Co-balk-O" and insert -- $C_{1-6}$alk-O -- therefor At Column 104, Line 64 (Claim 27), delete "Co-balk-O" and insert -- $C_{1-6}$alk-O -- therefor At Column 105, Line 2 (Claim 28), delete "Co-balk-O" and insert -- $C_{1-6}$alk-O -- therefor At Column 105, Line 7 (Claim 29), delete "Co-balk-O" and insert -- $C_{1-6}$alk-O -- therefor At Column 105, Line 15 (Claim 31), delete "Co-balk-O" and insert -- $C_{1-6}$alk-O -- therefor At Column 105, Line 62-63 (Claim 32), delete "(R)-3-(3-((4-chlorophenyl)amino)-4-(3,5-dimethylisoxazol-4-yl)phenyl)pentanoic acid;"

At Column 106, Lines 9-10 (Claim 32), delete "(R)-3-(3-(3-(4-chloro-2-fluorophenyl)ureido)-4-(1-methyl-1H-pyrazol-4-yl)phenyl)pentanoic acid;"

At Column 106, Lines 13-14 (Claim 32), delete "(R)-3-(3-(3-(4-chloro-2-fluorophenyl)ureido)-4-(1-isopropyl-1H-pyrazol-4-yl)phenyl)pentanoic acid;"

Signed and Sealed this
Thirtieth Day of November, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 10,959,986 B2

At Column 106, Lines 19-22 (Claim 32), delete both occurrences of "(S)-3-(4-(1-(tert-butoxycarbonyl)piperidin-4-yl)-3-((2-ethoxypyrimidin-5-yl)amino)phenyl) pentanoic acid;"

At Column 106, Lines 35-36 (Claim 32), delete "(S)-3-(4-(1-(tert-butoxycarbonyl)piperidin-4-yl)-3-((2-methylpyrimidin-5-yl)amino)phenyl) pentanoic acid;"

At Column 107, Line 2 (Claim 32), delete "acid" and insert -- acid; -- therefor

At Column 107, Lines 36-39 (Claim 32), delete both occurrences of "(S)-3-(4-(2,4-dimethylthiazol-5-yl)-3-((2-ethylpyrimidin-5-yl)amino)phenyl)pentanoic acid;"

At Column 107, Lines 46-47 (Claim 32), delete "(R)-3-(4-(2,4-dimethylthiazol-5-yl)-3-((2-ethylpyrimidin-5-yl)amino)phenyl)pentanoic acid;"

At Column 107, Lines 50-51 (Claim 32), delete "(R)-3-(4-(2,4-dimethylthiazol-5-yl)-3-((2-ethoxypyrimidin-5-yl)amino)phenyl)pentanoic acid;"